United States Patent
Ward et al.

(10) Patent No.: US 10,190,118 B2
(45) Date of Patent: Jan. 29, 2019

(54) METHODS AND COMPOSITIONS FOR TREATING INSECTS

(71) Applicant: ALNYLAM PHARMACEUTICALS, INC., Cambridge, MA (US)

(72) Inventors: Donna T. Ward, Cambridge, MA (US); Jason Rhodes, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 15/330,843

(22) Filed: Nov. 7, 2016

(65) Prior Publication Data

US 2017/0204411 A1    Jul. 20, 2017

Related U.S. Application Data

(63) Continuation of application No. 14/496,955, filed on Sep. 25, 2014, now abandoned, which is a continuation of application No. 13/364,477, filed on Feb. 2, 2012, now abandoned, which is a continuation of application No. PCT/US2010/043458, filed on Jul. 28, 2010.

(60) Provisional application No. 61/230,911, filed on Aug. 3, 2009.

(51) Int. Cl.

| | |
|---|---|
| *C07H 21/02* | (2006.01) |
| *C07H 21/04* | (2006.01) |
| *A61K 48/00* | (2006.01) |
| *C12N 15/113* | (2010.01) |
| *A01K 67/033* | (2006.01) |
| *C12N 15/85* | (2006.01) |
| *A01N 25/00* | (2006.01) |
| *A01N 57/16* | (2006.01) |
| *C12N 15/86* | (2006.01) |

(52) U.S. Cl.
CPC ........ *C12N 15/113* (2013.01); *A01K 67/0333* (2013.01); *A01N 25/002* (2013.01); *A01N 57/16* (2013.01); *C12N 15/1131* (2013.01); *C12N 15/85* (2013.01); *C12N 15/86* (2013.01); *A61K 48/00* (2013.01); *C12N 2310/14* (2013.01); *C12N 2320/00* (2013.01); *C12N 2320/30* (2013.01); *C12N 2320/32* (2013.01); *C12N 2710/14043* (2013.01)

(58) Field of Classification Search
CPC ............................. C12N 15/113; A61K 31/713
See application file for complete search history.

(56) References Cited

U.S. PATENT DOCUMENTS

| | | |
|---|---|---|
| 6,326,193 B1 | 12/2001 | Liu et al. |
| 2003/0055020 A1 | 3/2003 | Fire et al. |
| 2003/0203868 A1 | 10/2003 | Bushman et al. |
| 2003/0224041 A1 | 12/2003 | Huang et al. |
| 2007/0219131 A1 | 9/2007 | Ben-Sasson |
| 2008/0249046 A1 | 10/2008 | MacLachlan et al. |
| 2009/0118214 A1 | 5/2009 | Paldi et al. |
| 2011/0313017 A1 * | 12/2011 | Heyes ............... A61K 9/1271 514/44 A |
| 2012/0108497 A1 | 5/2012 | Paldi et al. |

FOREIGN PATENT DOCUMENTS

| | | |
|---|---|---|
| WO | 2006129204 A2 | 12/2006 |
| WO | 2009060429 A2 | 5/2009 |

OTHER PUBLICATIONS

Hagedorn et al. (Nucleic Acids Research, 2017, 45, 5, 2262-2282).*
Allerson et al., "Fully 2'-Modified Oligonucleotide Duplexes with Improved in Vitro Potency and Stability Compared to Unmodified Small Interfering RNA", J. Med. Chem. 48:901-904 (2005).
Mutinelli, "Practical Application of Antibacterial Drugs for the Control of Honey Bee Diseases", APIACTA 38:149-155 (2003).
Zimmermann et al., "The role of ARK in stress-induced apoptosis in *Drosophila* cells", J. Cell Biol. 156(6):1077-1087 (2002).

* cited by examiner

*Primary Examiner* — Amy H Bowman
(74) *Attorney, Agent, or Firm* — Nixon Peabody LLP; David S. Resnick; Mark J. FitzGerald

(57) ABSTRACT

Provided herein are methods and compositions for modulating gene expression in insects by administering a composition comprising an RNA effector molecule and a delivery agent. Methods are provided for controlling pest populations by inhibiting insect growth, development, survival, reproduction and/or viability. Also provided herein are methods for treating or preventing disease in an insect caused by a pathogen or by external factors (e.g., pollution, environment, stress, weather, etc.).

16 Claims, No Drawings
Specification includes a Sequence Listing.

SEQUENCE LISTING

```
<160> NUMBER OF SEQ ID NOS: 36

<210> SEQ ID NO 1

<400> SEQUENCE: 1

000

<210> SEQ ID NO 2
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ala Leu Glu Ala Leu Ala Glu Ala Leu Glu Ala Leu Ala Glu Ala
1               5                   10                  15

Leu Glu Ala Leu Ala Glu Ala Ala Ala Gly Gly Cys
            20                  25

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Gly Gly Cys
            20                  25                  30

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Leu Glu Ala Leu Ala Glu Ala Leu Glu Ala Leu Ala Glu Ala
1               5                   10                  15

<210> SEQ ID NO 5
<211> LENGTH: 22
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 5

```
Gly Leu Phe Glu Ala Ile Glu Gly Phe Ile Glu Asn Gly Trp Glu Gly
1               5                   10                  15

Met Ile Trp Asp Tyr Gly
            20
```

<210> SEQ ID NO 6
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Gly Leu Phe Gly Ala Ile Ala Gly Phe Ile Glu Asn Gly Trp Glu Gly
1               5                   10                  15

Met Ile Asp Gly Trp Tyr Gly
            20
```

<210> SEQ ID NO 7
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Gly Leu Phe Glu Ala Ile Glu Gly Phe Ile Glu Asn Gly Trp Glu Gly
1               5                   10                  15

Met Ile Asp Gly Trp Tyr Gly Cys Gly Leu Phe Glu Ala Ile Glu Gly
            20                  25                  30

Phe Ile Glu Asn Gly Trp Glu Gly Met Ile Asp Gly Trp Tyr Gly Cys
        35                  40                  45
```

<210> SEQ ID NO 8
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Gly Leu Phe Glu Ala Ile Glu Gly Phe Ile Glu Asn Gly Trp Glu Gly
1               5                   10                  15

Met Ile Asp Gly Gly Cys Gly Leu Phe Glu Ala Ile Glu Gly Phe Ile
            20                  25                  30

Glu Asn Gly Trp Glu Gly Met Ile Asp Gly Gly Cys
        35                  40
```

<210> SEQ ID NO 9
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 9

Gly Leu Phe Gly Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Gly
            20                  25                  30

Gly Ser Cys
        35

<210> SEQ ID NO 10
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Leu Phe Glu Ala Ile Glu Gly Phe Ile Glu Asn Gly Trp Glu Gly
1               5                   10                  15

Leu Ala Glu Ala Leu Ala Glu Ala Leu Glu Ala Leu Ala Ala Gly Gly
            20                  25                  30

Ser Cys

<210> SEQ ID NO 11
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Norleucine
<220> FEATURE:
<221> NAME/KEY: MOD_RES
<222> LOCATION: (38)..(38)
<223> OTHER INFORMATION: Norleucine

<400> SEQUENCE: 11

Gly Leu Phe Glu Ala Ile Glu Gly Phe Ile Glu Asn Gly Trp Glu Gly
1               5                   10                  15

Xaa Ile Asp Gly Lys Gly Leu Phe Glu Ala Ile Glu Gly Phe Ile Glu
            20                  25                  30

Asn Gly Trp Glu Gly Xaa Ile Asp Gly
        35                  40

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Leu Phe Glu Ala Leu Leu Glu Leu Leu Glu Ser Leu Trp Glu Leu
1               5                   10                  15

Leu Leu Glu Ala
            20

<210> SEQ ID NO 13
<211> LENGTH: 20
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 13

Gly Leu Phe Lys Ala Leu Leu Lys Leu Leu Lys Ser Leu Trp Lys Leu
1               5                   10                  15

Leu Leu Lys Ala
            20

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Leu Phe Arg Ala Leu Leu Arg Leu Leu Arg Ser Leu Trp Arg Leu
1               5                   10                  15

Leu Leu Arg Ala
            20

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 16
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Leu Phe Phe Glu Ala Ile Ala Glu Phe Ile Glu Gly Gly Trp Glu
1               5                   10                  15

Gly Leu Ile Glu Gly Cys
            20

<210> SEQ ID NO 17
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Ile Gly Ala Val Leu Lys Val Leu Thr Thr Gly Leu Pro Ala Leu
1               5                   10                  15

Ile Ser Trp Ile Lys Arg Lys Arg Gln Gln
```

```
                    20                  25

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

His His His His His Trp Tyr Gly
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys His Lys Lys Lys Lys Lys Lys His Cys
1               5                   10

<210> SEQ ID NO 20
<211> LENGTH: 16
<212> TYPE: PRT
<213> ORGANISM: Unknown
<220> FEATURE:
<223> OTHER INFORMATION: Description of Unknown: Penetratin
      peptide

<400> SEQUENCE: 20

Arg Gln Ile Lys Ile Trp Phe Gln Asn Arg Arg Met Lys Trp Lys Lys
1               5                   10                  15

<210> SEQ ID NO 21
<211> LENGTH: 27
<212> TYPE: PRT
<213> ORGANISM: Human immunodeficiency virus type 1

<400> SEQUENCE: 21

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
                20                  25

<210> SEQ ID NO 22
<211> LENGTH: 27
<212> TYPE: PRT
<213> ORGANISM: Unknown
<220> FEATURE:
<223> OTHER INFORMATION: Description of Unknown: Signal sequence
      based peptide

<400> SEQUENCE: 22

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
                20                  25

<210> SEQ ID NO 23
<211> LENGTH: 18
<212> TYPE: PRT
```

```
<213> ORGANISM: Unknown
<220> FEATURE:
<223> OTHER INFORMATION: Description of Unknown: PVEC peptide

<400> SEQUENCE: 23

Leu Leu Ile Ile Leu Arg Arg Arg Ile Arg Lys Gln Ala His Ala His
1               5                   10                  15

Ser Lys

<210> SEQ ID NO 24
<211> LENGTH: 26
<212> TYPE: PRT
<213> ORGANISM: Unknown
<220> FEATURE:
<223> OTHER INFORMATION: Description of Unknown: Transportan
      peptide

<400> SEQUENCE: 24

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 25
<211> LENGTH: 18
<212> TYPE: PRT
<213> ORGANISM: Unknown
<220> FEATURE:
<223> OTHER INFORMATION: Description of Unknown: Amphiphilic model
      peptide

<400> SEQUENCE: 25

Lys Leu Ala Leu Lys Leu Ala Leu Lys Ala Leu Lys Ala Ala Leu Lys
1               5                   10                  15

Leu Ala

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Arg Arg Arg Arg Arg Arg Arg Arg
1               5

<210> SEQ ID NO 27
<211> LENGTH: 10
<212> TYPE: PRT
<213> ORGANISM: Unknown
<220> FEATURE:
<223> OTHER INFORMATION: Description of Unknown: Bacterial cell wall
      permeating peptide

<400> SEQUENCE: 27

Lys Phe Phe Lys Phe Phe Lys Phe Phe Lys
1               5                   10

<210> SEQ ID NO 28
<211> LENGTH: 37
<212> TYPE: PRT
<213> ORGANISM: Unknown
<220> FEATURE:
<223> OTHER INFORMATION: Description of Unknown: LL-37
``` polypeptide

<400> SEQUENCE: 28

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 29
<211> LENGTH: 31
<212> TYPE: PRT
<213> ORGANISM: Unknown
<220> FEATURE:
<223> OTHER INFORMATION: Description of Unknown: Cecropin P1
      polypeptide

<400> SEQUENCE: 29

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 30
<211> LENGTH: 30
<212> TYPE: PRT
<213> ORGANISM: Unknown
<220> FEATURE:
<223> OTHER INFORMATION: Description of Unknown: Alpha-defensin
      polypeptide

<400> SEQUENCE: 30

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 31
<211> LENGTH: 36
<212> TYPE: PRT
<213> ORGANISM: Unknown
<220> FEATURE:
<223> OTHER INFORMATION: Description of Unknown: Beta-defensin
      polypeptide

<400> SEQUENCE: 31

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
        35

<210> SEQ ID NO 32
<211> LENGTH: 42
<212> TYPE: PRT
<213> ORGANISM: Unknown
<220> FEATURE:
<223> OTHER INFORMATION: Description of Unknown: PR-39
      polypeptide

<400> SEQUENCE: 32

Arg Arg Arg Pro Arg Pro Pro Tyr Leu Pro Arg Pro Arg Pro Pro Pro

```
                1               5                   10                  15
Phe Phe Pro Pro Arg Leu Pro Pro Arg Ile Pro Pro Gly Phe Pro Pro
                    20                  25                  30

Arg Phe Pro Pro Arg Phe Pro Gly Lys Arg
        35                  40

<210> SEQ ID NO 33
<211> LENGTH: 13
<212> TYPE: PRT
<213> ORGANISM: Unknown
<220> FEATURE:
<223> OTHER INFORMATION: Description of Unknown: Indolicidin
      peptide

<400> SEQUENCE: 33

Ile Leu Pro Trp Lys Trp Pro Trp Trp Pro Trp Arg Arg
1               5                   10

<210> SEQ ID NO 34
<211> LENGTH: 16
<212> TYPE: PRT
<213> ORGANISM: Unknown
<220> FEATURE:
<223> OTHER INFORMATION: Description of Unknown: RFGF peptide

<400> SEQUENCE: 34

Ala Ala Val Ala Leu Leu Pro Ala Val Leu Leu Ala Leu Leu Ala Pro
1               5                   10                  15

<210> SEQ ID NO 35
<211> LENGTH: 11
<212> TYPE: PRT
<213> ORGANISM: Unknown
<220> FEATURE:
<223> OTHER INFORMATION: Description of Unknown: RFGF analogue
      peptide

<400> SEQUENCE: 35

Ala Ala Leu Leu Pro Val Leu Leu Ala Ala Pro
1               5                   10

<210> SEQ ID NO 36
<211> LENGTH: 12
<212> TYPE: PRT
<213> ORGANISM: Unknown
<220> FEATURE:
<223> OTHER INFORMATION: Description of Unknown: Bactenecin
      peptide

<400> SEQUENCE: 36

Arg Lys Cys Arg Ile Val Val Ile Arg Val Cys Arg
1               5                   10
```

METHODS AND COMPOSITIONS FOR TREATING INSECTS

CROSS-REFERENCE TO RELATED APPLICATIONS

This application is a Continuation application under 35 U.S.C. § 120 of U.S. application Ser. No. 14/496,955, filed on Sep. 25, 2014, which is a Continuation application of U.S. application Ser. No. 13/364,477, filed on Feb. 2, 2012, which is a Continuation application of International Application No. PCT/US2010/043458, filed on Jul. 28, 2010, which designates the U.S. and which claims benefit under 35 U.S.C. § 119(e) of U.S. Provisional Application No. 61/230,911, filed on Aug. 3, 2009, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Nov. 7, 2016, is named 051058-053101-C3_SL.txt and is 12,682 bytes in size.

FIELD OF THE INVENTION

The field of the invention relates to the treatment of insects with a composition comprising an RNA effector molecule.

BACKGROUND

Pests including insects, arachnids, crustaceans, fungi, bacteria, viruses, nematodes, flatworms, roundworms, pinworms, hookworms, tapeworms, trypanosomes, schistosomes, botflies, fleas, ticks, mites, lice and the like are pervasive in the human environment, and a multitude of means have been utilized for attempting to control infestations by these pests. Compositions for controlling infestations by microscopic pests such as bacteria, fungi, and viruses have been provided in the form of antibiotic compositions, antiviral compositions, and antifungal compositions. Compositions for controlling infestations by larger pests such as nematodes, flatworm, roundworms, pinworms, heartworms, tapeworms, trypanosomes, schistosomes, and the like have typically been in the form of chemical compositions which can either be applied to the surfaces of substrates on which pests are known to infest, or to be ingested by an infested animal in the form of pellets, powders, tablets, pastes, or capsules and the like.

SUMMARY OF THE INVENTION

Described herein are compositions comprising an RNA effector molecule and methods for administering such compositions to an insect or group of insects, wherein the RNA effector molecule modulates gene expression. The compositions are useful for controlling insect pest populations by inhibiting survival, viability, reproductions, growth and/or development of a pest population. Alternatively, the compositions are useful for treating or preventing a disease, including, but not limited to, pathogen-borne disease or disease caused by environmental factors (e.g., pollution, agricultural chemicals), in insects having a beneficial function by modulating gene expression of the pathogen or of the insect.

One aspect described herein relates to a method for modulating gene expression in an insect, the method comprising: administering to the insect a composition comprising an RNA effector molecule or a vector encoding an RNA effector molecule, and a delivery agent, wherein the RNA effector molecule modulates gene expression in the insect.

Another aspect described herein relates to a method for treating or preventing disease in an insect, the method comprising administering to the insect a composition comprising an RNA effector molecule or a vector encoding an RNA effector molecule, and a delivery agent, wherein the RNA effector molecule modulates gene expression of an insect or insect pathogen.

As used herein, an "RNA effector molecule" refers to a molecule that modulates the expression of a gene. In certain embodiments, the RNA effector molecule is an oligonucleotide. As used herein, the oligonucleotide can comprise an RNA interference agent, an RNA activator, an miRNA, an shRNA, a ribozyme, an antisense RNA, a decoy oligonucleotide, an antimir, or a supermir.

As used herein, the terms "RNA interference agent," "RNAi" or "iRNA" refer to an oligonucleotide as that term is defined herein, and which mediates the targeted cleavage of an RNA transcript via an RNA-induced silencing complex (RISC) pathway.

The iRNAs included in the compositions featured herein encompass a dsRNA having an RNA strand (the antisense strand) having a region that is typically 9-36 nucleotides in length, e.g., 30 nucleotides or less, generally 19-24 nucleotides in length, that is substantially complementary to at least part of an mRNA transcript of an insect pest or an insect pathogen.

In one embodiment, an iRNA for modulating expression of an insect or insect pathogen gene includes at least two sequences that are complementary to each other. The iRNA includes a sense strand having a first sequence and an antisense strand having a second sequence. The antisense strand includes a nucleotide sequence that is substantially complementary to at least part of an mRNA of a target gene, and the region of complementarity is 30 nucleotides or less, and at least 15 nucleotides in length. Generally, the iRNA is 19 to 24, e.g., 19 to 21 nucleotides in length. In some embodiments the iRNA is from about 15 to about 25 nucleotides in length, and in other embodiments the iRNA is from about 25 to about 30 nucleotides in length. In another embodiment of this aspect, the oligonucleotide comprises 9-36 base pairs.

The iRNA, upon contacting with an insect or insect pathogen, inhibits the expression of a target gene by at least 10%, at least 20%, at least 25%, at least 30%, at least 35% or at least 40% or more. In one embodiment, the iRNA is formulated in a stable nucleic acid lipid particle (SNALP).

In another embodiment of this aspect, the oligonucleotide is a single stranded or double stranded oligonucleotide.

In another embodiment of this aspect, the oligonucleotide is modified. The oligonucleotide molecules featured herein can include naturally occurring nucleotides or can include at least one modified nucleotide, including, but not limited to a 2'-O-methyl modified nucleotide, a nucleotide having a 5'-phosphorothioate group, and a terminal nucleotide linked to a cholesteryl derivative. Alternatively, the modified nucleotide can be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

In one aspect, the invention provides a vector for inhibiting the expression of a insect or insect pathogen gene. In one embodiment, the vector includes at least one regulatory sequence operably linked to a nucleotide sequence that encodes at least one strand of an iRNA featured in the invention.

In one embodiment of these aspects, the disease is caused by an insect pathogen selected from the group consisting of a virus, mite, nematode, bacteria, fungus, or parasite. Alternatively, the disease can be caused by external factors including, but not limited to, pollution, exposure to electromagnetic radiation, exposure to pesticides, environment, or stress.

In one embodiment of this aspect, the insect is a pest. Alternatively, the insect comprises a beneficial insect such as e.g., a bee, wasp, butterfly, ant or ladybug.

In another embodiment of the aspects described herein, the RNA effector molecule inhibits or activates gene expression.

In another embodiment of the aspects described herein, the modulation of gene expression inhibits viability, survival, growth, development, and/or reproduction of the insect. In another embodiment of the aspects described herein modulation of gene expression increases insect susceptibility to a pathogen.

In another embodiment of the aspects described herein, administering comprises providing a food source for the insect, wherein the food source comprises the composition. A food source can be provided as a liquid, solid, gel, semi-solid composition, sugar composition, or lipid composition. Alternatively, the food source comprises a bacterium, a virus, a fungus, a plant or a yeast cell expressing the oligonucleotide.

In another embodiment of the aspects described herein, the insect is a hive-dwelling insect and modulation of gene expression in the insect is delayed until the insect returns to the hive.

In another embodiment of the aspects described herein, the hive-dwelling insect spreads the composition to other insects in the hive.

In another embodiment of the aspects described herein, the insect is a bee such as e.g., a forager bee, a hive bee, a queen bee, a drone bee, a worker bee etc. In some embodiments the pathogen is a bee pathogen selected from the group consisting of IAPV, Acute Bee Paralysis Virus and Kashmir Bee Paralysis Virus.

In another embodiment of the aspects described herein, administering comprises contacting the insect with a solution comprising the composition. The composition can be administered topically, or alternatively the insect, its habitat or a field is sprayed or soaked with the solution.

In another embodiment of the aspects described herein, the delivery agent is a lipid, a liposome, a food source, a solution, an emulsion, a micelle or other membranous formulation, a lipid particle, a bacteria, a fungi, a plant, a yeast cell, or a yeast cell particle.

In another embodiment, the vector is a viral vector (e.g., a baculoviral vector), an expression vector or a plasmid.

In another embodiment of the aspects described herein, the lipid particle comprises about 15-25% triacylglycerol, about 0.5-2% phospholipids, about 1-3% glycerol, and at least one lipid-binding protein.

In another embodiment of this aspect, the composition is provided in a spray, solution, gel, bait, a food source, or powder form. The composition can further comprise an attractant, such as e.g., an insect pheromone or hormone.

In another embodiment of the aspects described herein, the composition is specific to the pest and does not affect other insects.

In another embodiment of the aspects described herein, the composition is administered to adult insects.

In another embodiment of the aspects described herein, the composition is administered to a breeding or feeding locus.

In another embodiment of the aspects described herein, the composition further comprises an additional agent, including but not limited to antivirals, antifungals, antibacterials, pesticides, antihelminthics, nutrients, pollen, sucrose and/or agents that stun or slow insect movement.

In another embodiment of the aspects described herein, the insect pathogen is a virus, mite, nematode, bacteria, fungus, or parasite.

In another embodiment of the aspects described herein, modulating gene expression inhibits pathogen infectivity, virulence, reproduction, viability, growth, translation, protein production, viral uptake or transmission of the insect pathogen.

In another embodiment of the aspects described herein, modulating gene expression decreases insect susceptibility to a pathogen.

Another aspect described herein relates to a composition comprising an RNA effector molecule or a vector encoding an RNA molecule, and a delivery agent, wherein the RNA effector molecule modulates gene expression of an insect or an insect pathogen. The composition can further comprise an insect attractant.

In one embodiment of this aspect, the oligonucleotide comprises an siRNA, an miRNA, an shRNA, a ribozyme, an antisense RNA, a decoy oligonucleotide, an antimir, a supermir, or an RNA activator. The oligonucleotide can be a single stranded or double stranded oligonucleotide. In some embodiments, the oligonucleotide comprises 9-36 base pairs. The oligonucleotide can be modified in any manner as known in the art and/or described herein.

In another embodiment of this aspect, the delivery agent is a viral vector, a plasmid, a lipid, a liposome, a food source, an expression vector, a solution, an emulsion, a micelle or other membranous formulation, a lipid particle (e.g., INTRALIPID™), a bacteria, a fungi, a plant, a yeast cell, or a yeast cell particle.

In another embodiment of this aspect, the food source is a bacteria, fungus, plant, or yeast expressing the oligonucleotide.

In another embodiment of this aspect, the composition inhibits viability, survival, growth, development, and/or reproduction of the insect.

In another embodiment of this aspect, the composition inhibits pathogen infectivity, virulence, reproduction, viability, growth, translation, protein production, viral uptake or transmission of the insect pathogen.

The composition can be provided in a spray, solution, gel, topical formulation, or powder form. In addition, the composition can further comprise an antibiotic, antiviral, antifungal pesticides, antihelminthics, nutrients, pollen, sucrose and/or agents that stun or slow insect movement. In another embodiment of this aspect, the attractant comprises an insect pheromone or hormone.

Definitions

As used herein the term "administering" encompasses any method by which an insect can come-into contact with an oligonucleotide as that term is used herein. In one embodiment, the oligonucleotide is a dsRNA comprising annealed complementary strands, one of which has a nucleotide sequence which is complementary to at least part of the nucleotide sequence of an insect target gene to be modulated. An insect can be exposed to a composition (e.g., an oligonucleotide and a delivery agent) by direct uptake (e.g. by feeding), which does not require expression of the oligonucleotide within the insect. Alternatively, an insect can come into direct contact with a composition comprising the oligonucleotide. For example, an insect can come into contact with a surface or material treated with a composition comprising an oligonucleotide. An oligonucleotide can be expressed by a prokaryotic (for instance, but not limited to, a bacterial) or eukaryotic (for instance, but not limited to, a yeast) host cell or host organism. (also virally encoded source)

As used herein the term "additional agent" refers to a small molecule, chemical, organic, or inorganic molecule that can be used to treat insects. In one embodiment, the "additional agent" is a pesticide. As used herein, the term "pesticide" refers to any substance or mixture of substances intended for preventing, destroying, repelling, or mitigating any pest. A pesticide can be a chemical substance or biological agent used against pests including insects, pathogens, weeds, nematodes, and microbes that compete with humans for food, destroy property, spread disease, or are a nuisance. The term "additional agent" further encompasses other bioactive molecules such as antibiotics, antivirals pesticides, antifungals, antihelminthics, nutrients, pollen, sucrose and/or agents that stun or slow insect movement.

As used herein the term "plant" is used to refer to any of various photosynthetic, eukaryotic, multicellular organisms of the kingdom Plantae characteristically producing embryos, containing chloroplasts, and having cellulose cell walls. A part of a plant, i.e., a "plant tissue" can be treated according to the methods described herein to prevent pest infestation on the plant or on part of the plant. Alternatively, a plant can be treated to improve the health of a beneficial insect population by modulating gene expression of an insect pathogen. In addition, a plant can be engineered to express an oligonucleotide useful with the methods described herein. Many suitable plant tissues can be treated according to the present invention and include, but are not limited to, somatic embryos, pollen, leaves, stems, calli, stolons, microtubers, and shoots. Thus, the present invention envisions the treatment of angiosperm and gymnosperm plants such as acacia, alfalfa, apple, apricot, artichoke, ash tree, asparagus, avocado, banana, barley, beans, beet, birch, beech, blackberry, blueberry, broccoli, brussels sprouts, cabbage, canola, cantaloupe, carrot, cassava, cauliflower, cedar, a cereal, celery, chestnut, cherry, Chinese cabbage, citrus, clementine, clover, coffee, corn, cotton, cowpea, cucumber, cypress, eggplant, elm, endive, eucalyptus, fennel, figs, fir, geranium, grape, grapefruit, groundnuts, ground cherry, gum hemlock, hickory, kale, kiwifruit, kohlrabi, larch, lettuce, leek, lemon, lime, locust, pine, maidenhair, maize, mango, maple, melon, millet, mushroom, mustard, nuts, oak, oats, okra, onion, orange, an ornamental plant or flower or tree, papaya, palm, parsley, parsnip, pea, peach, peanut, pear, peat, pepper, persimmon, pigeon pea, pine, pineapple, plantain, plum, pomegranate, potato, pumpkin, radicchio, radish, rapeseed, raspberry, rice, rye, sorghum, sallow, soybean, spinach, spruce, squash, strawberry, sugarbeet, sugarcane, sunflower, sweet potato, sweet corn, tangerine, tea, tobacco, tomato, trees, triticale, turf grasses, turnips, a vine, walnut, watercress, watermelon, wheat, yams, yew, and zucchini.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

The details of one or more embodiments of the invention are set forth in the description below. Other features, objects, and advantages of the invention will be apparent from the description and the drawings, and from the claims.

DETAILED DESCRIPTION

The methods and compositions described herein provide for modulation of gene expression in insects by administering a composition comprising an RNA effector molecule and a delivery agent. Methods are provided for controlling pest populations by inhibiting insect growth, development, survival, reproduction and/or viability. Also provided herein are methods for treating or preventing disease in an insect caused by a pathogen or by external factors (e.g., pollution, environment, stress, weather, etc.).

Insect Pests

The present invention provides methods and compositions for controlling pest infestations by administering, or otherwise exposing, to a pest a composition comprising an oligonucleotide that post-transcriptionally modulates (e.g., represses, inhibits, or activates) a requisite biological function in the pest.

As used herein, the term "pest" refers to insects that cause damage to plants, other organisms or otherwise causes a nuisance. A pest can ingest or contact one or more cells, tissues, or products produced by an organism transformed with an oligonucleotide composition as described herein, as well as a surface or material treated with such an oligonucleotide composition.

As used herein the term "insect" describes any insect, meaning any organism belonging to the Kingdom Animals, more specific to the Phylum Arthropoda, and to the Class Insecta or the Class Arachnida.

In one embodiment of the invention, the insect can belong to the following orders: Acari, Araneae, Anoplura, Coleoptera, Collembola, Dermaptera, Dictyoptera, Diplura, Diptera, Embioptera, Ephemeroptera, Grylloblatodea, Hemiptera, Homoptera, Hymenoptera, Isoptera, Lepidoptera, Mallophaga, Mecoptera, Neuroptera, Odonata, Orthoptera, Phasmida, Plecoptera, Protura, Psocoptera, Siphonaptera, Siphunculata, Thysanura, Strepsiptera, Thysanoptera, Trichoptera, and Zoraptera.

As used herein, the terms "pest" or "insect pests" include but are not limited to the following examples: from the order Lepidoptera, for example, *Acleris* spp., *Adoxophyes* spp., *Aegeria* spp., *Agrotis* spp., *Alabama argillaceae, Amylois* spp., *Anticarsia gemmatalis, Archips* spp, *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia Nubilalis, Pammene* spp., *Pandemis* spp., *Panolis flammea, Pectinophora gossypiella, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.; from the order Coleoptera, for example, *Agriotes* spp., *Anthonomus* spp., *Atomaria linearis, Chaetocnema tibialis, Cosmopolites* spp., *Curculio* spp., *Dermestes* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.; from the order Orthoptera, for example, *Blatta* spp., *Blattella* spp., *Gryllotalpa* spp., *Leucophaea maderae, Locusta* spp., *Periplaneta* ssp., and *Schistocerca* spp.; from the order Isoptera, for spp; from the order Psocoptera, for spp.; from the order Anoplura, for example *jfaematopinus* spp., *Linognathus* spp., *Pediculus* spp., *Pemphigus* spp. and *Phylloxera* spp.; from the order Mallophaga, for example₍[Hat]₎*Dalphamalpha/mealpha* spp. and *Trichodectes* spp.; from the order Thysanoptera, for spp., *Hercinothrips* spp., *Taeniothrips* spp., *Thrips palmi, Thrips tabaci* and *Scirtothrips aurantii*; from the order Heteroptera, for example, *Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp., *Triatoma* spp., Miridae family spp. such as *Lygus hesperus* and *Lygus lineoloris*, LygaeidaQ family spp. such as *Blissus leucopterus*, and Pentatomidae family spp.; from the order Homoptera, for example, *Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lacanium corni, Lepidosaphes* spp., *Macrosiphus* spp., *Myzus* spp., *Nehotettix* spp., *Nilaparvata* spp., *Paratoria* spp., *Pemphigus* spp., *Planococcus* spp., *Pseudaulacaspis* spp., *Pseudococcus* spp., *Psylla* ssp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri*; from the order Hymenoptera, for example, *Acromyrmex, Atta* spp., *Cephus* spp., *Diprion* spp., *Diprionidae, Gilpinia polytoma, Hoplocampa* spp., *Lasius* sppp., *Monomorium pharaonis, Neodiprion* spp, *Solenopsis* spp. and *Vespa* ssp.; from the order Diptera, for example, *Aedes* spp., *Antherigona soccata, Bibio hortulanus, CalHphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomysa* spp., *Lucilia* spp., *Melanagromyza* spp., *Musca* ssp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp., from the order Siphonaptera, for example, *Ceratophyllus* spp. and *Xenopsylla cheopis* and from the order Thysanura, for example *Lepisma saccharina*.

In one embodiment the insect is chosen from the group consisting of: an insect which is a plant pest, such as but not limited to *Nilaparvata* spp. (e.g. *N. lugens* (brown planthopper)); *Laodelphax* spp. (e.g. *L. striatellus* (small brown planthopper)); *Nephotettix* spp. (e.g. *N. virescens* or *N. cincticeps* (green leafhopper), or *N. nigropictus* (rice leafhopper)); *Sogatella* spp. (e.g. *S. furcifera* (white-backed planthopper)); *Blissus* spp. (e.g. *B. leucopterus leucopterus* (chinch bug)); *Scotinophora* spp. (e.g. *S. vermidulate* (rice blackbug)); *Acrosternum* spp. (e.g. *A. Mare* (green stink bug)); *Parnara* spp. (e.g. *P. guttata* (rice skipper)); *Chilo* spp. (e.g. *C. suppressalis* (rice striped stem borer), *C. auricilius* (gold-fringed stem borer), or *C. polychrysus* (dark-headed stem borer)); *Chilotraea* spp. (e.g. *C. polychrysa* (rice stalk borer)); *Sesamia* spp. (e.g. *S. inferens* (pink rice borer)); *Tryporyza* spp. (e.g. *T. innotata* (white rice borer), or *T. incertulas* (yellow rice borer)); *Cnaphalocrocis* spp. (e.g. *C. medinalis* (rice leafroller)); *Agromyza* spp. (e.g. *A. oryzae* (leafminer), or *A. parvicornis* (corn blot leafminer)); *Diatraea* spp. (e.g. *D. saccharalis* (sugarcane borer), or *D. grandiosella* (southwestern corn borer)); *Narnaga* spp. (e.g. *N. aenescens* (green rice caterpillar)); *Xanthodes* spp. (e.g. *X. transversa* (green caterpillar)); *Spodoptera* spp. (e.g. *S. frugiperda* (fall armyworm), *S. exigua* (beet armyworm), *S. littoralis* (climbing cutworm) or *S. praefica* (western yellowstriped armyworm)); *Mythimna* spp. (e.g. *Mythmna (Pseudaletia) seperata* (armyworm)); *Helicoverpa* spp. (e.g. *H. zea* (corn earworm)); *Colaspis* spp. (e.g. *C. brunnea* (grape colaspis)); *Lissorhoptrus* spp. (e.g. *L. oryzophilus* (rice water weevil)); *Echinocnemus* spp. (e.g. *E. squamos* (rice plant weevil)); Diclodispa spp. (e.g. *D. armigera* (rice hispa)); *Oulema* spp. (e.g. *O. oryzae* (leaf beetle); *Sitophilus* spp. (e.g. *S. oryzae* (rice weevil)); *Pachydiplosis* spp. (e.g. *P. oryzae* (rice gall midge)); *Hydrellia* spp. (e.g. *H. griseola* (small rice leafminer), or *H. sasakii* (rice stem maggot)); *Chlorops* spp. (e.g. *C. oryzae* (stem maggot)); *Ostrinia* spp. (e.g. *O. nubilalis* (European corn borer)); *Agrotis* spp. (e.g. *A. ipsilon* (black cutworm)); *Elasmopalpus* spp. (e.g. *E. lignosellus* (lesser cornstalk borer)); *Melanotus* spp. (wireworms); *Cyclocephala* spp. (e.g. *C. borealis* (northern masked chafer), or *C. immaculata* (southern masked chafer)); *Popillia* spp. (e.g. *P. japonica* (Japanese beetle)); *Chaetocnema* spp. (e.g. *C. pulicaria* (corn flea beetle)); *Sphenophorus* spp. (e.g. *S. maidis* (maize billbug)); *Rhopalosiphum* spp. (e.g. *R. maidis* (corn leaf aphid)); *Anuraphis* spp. (e.g. *A. maidiradicis* (corn root aphid)); *Melanoplus* spp. (e.g. *M. femurrubrum* (redlegged grasshopper) *M. differentialis* (differential grasshopper) or *M. sanguinipes* (migratory grasshopper)); *Hylemya* spp. (e.g. *H. platura* (seedcorn maggot)); *Anaphothrips* spp. (e.g. *A. obscrurus* (grass thrips)); *Solenopsis* spp. (e.g. *S. milesta* (thief ant)); or spp. (e.g. *T. urticae* (twospotted spider mite), *T. cinnabarinus* (carmine spider mite); *Helicoverpa* spp. (e.g. *H. zea* (cotton bollworm), or *H. armigera* (American bollworm)); *Pectinophora* spp. (e.g. *P. gossypiella* (pink bollworm)); *Earias* spp. (e.g. *E. vittella* (spotted bollworm)); *Heliothis* spp. (e.g. *H. virescens* (tobacco budworm)); *Anthonomus* spp. (e.g. *A. grandis* (boll weevil)); *Pseudatomoscelis* spp. (e.g. *P. seriatus* (cotton fleahopper)); *Trialeurodes* spp. (e.g. *T. abutiloneus* (banded-winged whitefly) *T. vaporariorum* (greenhouse whitefly)); *Bemisia* spp. (e.g. *B. argentifol* (silverleaf whitefly)); *Aphis* spp. (e.g. *A. gossypii* (cotton aphid), *A. mellifera*); *Lygus* spp. (e.g. *L. lineolaris* (tarnished plant bug) or *L. hesperus* (western tarnished plant bug)); *Euschistus* spp. (e.g. *E. conspersus* (consperse stink bug)); *Chlorochroa* spp. (e.g. *C. sayi* (Say stinkbug)); *Nezara* spp. (e.g. *N. viridula* (southern green stinkbug)); *Thrips* spp. (e.g. *T. tabaci* (onion *thrips*)); *Frankliniella* spp. (e.g. *F. fusca* (tobacco *thrips*), or *F. occidentalis* (western flower *thrips*)); *Leptinotarsa* spp. (e.g. *L. decemlineata* (Colorado potato beetle), *L. juncta* (false potato beetle), or *L. texana* (Texan false potato beetle)); *Lema* spp. (e.g. *L. trilineata* (three-lined potato beetle)); *Epitrix* spp. (e.g. *E. cucumeris* (potato flea beetle), *E. hirtipennis* (flea beetle), or *E. tuberis* (tuber flea beetle)); *Epicauta* spp. (e.g. *E. vittata* (striped blister beetle)); *Empoasca* spp. (e.g. *E. fabae* (potato leafhopper)); *Myzus* spp. (e.g. *M. persicae* (green peach aphid)); *Paratrioza* spp. (e.g. *P. cockerelli* (psyllid)); *Conoderus* spp. (e.g. *C. falli* (southern potato wireworm), or *C. vespertinus* (tobacco wireworm)); *Phthorimaea* spp. (e.g. *P. operculella* (potato tuberworm)); *Macrosiphum* spp. (e.g. *M. euphorbiae* (potato aphid)); *Thyanta* spp. (e.g. *T. pallidovirens* (redshouldered stinkbug)); *Phthorimaea* spp. (e.g. *P. operculella* (potato tuberworm)); *Helicoverpa* spp. (e.g. *H. zea* (tomato fruitworm); *Keiferia* spp. (e.g. *K. lycopersicella* (tomato pinworm)); *Limonius* spp. (wireworms); *Manduca* spp. (e.g. *M. sexta* (tobacco hornworm), or *M. quinquemaculata* (tomato hornworm)); *Liriomyza* spp. (e.g. *L. sativae*, *L. trifolli* or *L. huidobrensis* (leafminer)); *Drosophilla* spp. (e.g. *D. melanogaster, D. yakuba, D. pseudoobscura* or *D. simulans*); *Carabus* spp. (e.g. *C. granulatus*); *Chironomus* spp. (e.g. *C. tentanus*); *Ctenocephalides* spp. (e.g. *C. felis* (cat flea)); *Diaprepes* spp. (e.g. *D. abbreviatus* (root weevil)); *Ips* spp. (e.g. *Ips. pini* (pine engraver)); *Tribolium* spp. (e.g. *T. castaneum* (red floor beetle)); *Glossina* spp. (e.g. *G. morsitans* (tsetse fly)); *Anopheles* spp. (e.g. *A. gambiae* (malaria mosquito)); *Helicoverpa* spp. (e.g. *H. armigera* (African Bollworm)); *Acyrthosiphon* spp. (e.g. *A. pisum* (pea aphid)); *Apis* spp. (e.g. *A. melifera* (honey bee)); *Homalodisca* spp. (e.g. *H. coagulate* (glassy-winged sharpshooter)); *Aedes* spp. (e.g. *Ae. aegypti* (yellow fever mosquito)); *Bombyx* spp. (e.g. *B. mori* (silkworm), *B. mandarina*); *Locusta* spp. (e.g. *L. migratoa* (migratory locust)); *Boophilus* spp. (e.g. *B. microplus* (cattle tick)); *Acanthoscurria* spp. (e.g. *A. gomesiana* (red-haired chololate bird eater)); *Diploptera* spp. (e.g. *D. punctata* (pacific beetle cockroach)); *Heliconius* spp. (e.g. *H. erato* (red passion flower butterfly) or *H. melpomene* (postman butterfly)); *CurcuHo* spp. (e.g. *C. glandium* (acorn weevil)); *Plutella* spp. (e.g. *P. xylostella* (diamondback moth)); *Amblyomma* spp. (e.g. *A. variegatum* (cattle tick)); *Anteraea* spp. (e.g. *A. yamamai* (silkmoth)); *Belgica* spp. (e.g. *B. antartica*), *Bemisa* spp. (e.g. *B. tabaci*), *Bicyclus* spp., *Biphillus* spp., *Collosobruchus* spp., *Choristoneura* spp., *Cicindela* spp., *Culex* spp., *Culicoides* spp., *Diaphorina* spp., *Diaprepes* spp., *Euclidia* spp., *Glossina* spp., *Gryllus* spp., *Hydropsyche* spp., *Julodis* spp., *Lonomia* spp., *Lutzomyia* spp., *Lysiphebus* spp, *Meladema* spp, *Mycetophagus* spp., *Nasonia* spp., *Oncometopia* spp., *Papilio* spp., *Pediculus* spp., *Plodia* spp., *Rhynchosciara* spp., *Sphaerius* spp., *Toxoptera* spp., *Tchoplusa* spp., and *Armigeres* spp.

In another embodiment an insect is chosen for gene expression modulation that is capable of infesting or injuring humans and/or animals such as, but not limited to those with piercing-sucking mouthparts, as found in Hemiptera and some Hymenoptera and Diptera such as mosquitoes, bees, wasps, lice, fleas and ants, as well as members of the Arachnidae such as ticks and mites; order, class or family of Acarina (ticks and mites) e.g. representatives of the families Argasidae, Dermanyssidae, Ixodidae, Psoroptidae or Sarcoptidae and representatives of the species *Amblyomma* spp., *Anocentor* spp., *Argas* spp., *Boophilus* spp., *Cheyletiella* spp., *Chorioptes* spp., *Demodex* spp., *Dermacentor* spp., *Dermanyssus* spp., *Haemophysalis* spp., *Hyalomma* spp., *Ixodes* spp., *Lynxacarus* spp., *Mesostigmata* spp., *Notoedres* spp., *Ornithodoros* spp., *Ornithonyssus* spp., *Otobius* spp., *otodectes* spp., *Pneumonyssus* spp., *Psoroptes* spp., *Rhipicephalus* spp., *Sarcoptes* spp., or *Trombicula* spp.; Anoplura (sucking and biting lice) e.g. representatives of the species *Bovicola* spp., *Haematopinus* spp., *Linognathus* spp., *Menopon* spp., *Pediculus* spp., *Pemphigus* spp., *Phylloxera* spp., or *Solenopotes* spp.; Diptera (flies) e.g. representatives of the species *Aedes* spp., *Anopheles* spp., *Calliphora* spp., *Chrysomyia* spp., *Chrysops* spp., *Cochliomyia* spp., *Cw/ex* spp., *CuUcoides* spp., *Cuterebra* spp., *Dermatobia* spp., *Gastrophilus* spp., *Glossina* spp., *Haematobia* spp., *Haematopota* spp., *Hippobosca* spp., *Hypoderma* spp., *Lucilia* spp., *Lyperosia* spp., *Melophagus* spp., *Oestrus* spp., *Phaenicia* spp., *Phlebotomus* spp., *Phormia* spp., *Sarcophaga* spp., *Simulium* spp., *Stomoxys* spp., *Tabanus* spp., *Tannia* spp. or *Zzpu/alpha* spp.; Mallophaga (biting lice) e.g. representatives of the species *Damalina* spp., *Felicola* spp., *Heterodoxus* spp. or *Trichodectes* spp.; or Siphonaptera (wingless insects) e.g. representatives of the species *Ceratophyllus* spp., *Xenopsylla* spp; Cimicidae (true bugs) e.g. representatives of the species *Cimex* spp., *Tritominae* spp., *Rhodinius* spp., or *Triatoma* spp.

In another embodiment a target insect is treated as described herein to prevent unwanted damage to substrates or materials, such as insects that attack foodstuffs, seeds, wood, paint, plastic, clothing etc.

Target Genes

In practicing the present invention, the expression of target gene derived from any pest that causes damage to another organism can be modulated using the methods and compositions described herein. Several criteria can be employed in the selection of preferred target genes. In one embodiment, the gene is one whose protein product has a rapid turnover rate, so that inhibition of gene expression will result in a rapid decrease in protein levels. In certain embodiments it is advantageous to select a gene for which a small change (e.g., reduction) in expression level results in deleterious effects for the recipient pest. If it is desired to target a broad range of insect species, for example, a gene is selected that is highly conserved across these species. Conversely, for the purpose of conferring specificity, in certain embodiments of the invention, a gene is selected that contains regions that are poorly conserved between individual insect species, or between insects and other organisms; in certain embodiments it can be desirable to select a gene that has no known homologs in other organisms.

In one embodiment, a gene is selected that is expressed in the insect gut. Target genes for use in the present invention can include, for example, those that share substantial homologies to the nucleotide sequences of known gut-expressed genes that encode protein components of the plasma membrane proton V-ATPase. This protein complex is the sole energizer of epithelial ion transport and is responsible for alkalinization of the midgut lumen. The V-ATPase is also expressed in the Malpighian tubule, an outgrowth of the insect hindgut that functions in fluid balance and detoxification of foreign compounds in a manner analogous to a kidney organ of a mammal.

In another embodiment, a gene is selected that is essentially involved in the growth, development, and reproduction of an insect. Exemplary genes include but are not limited to the structural subunits of ribosomal proteins and a beta-coatamer gene, CHD3 gene. Ribosomal proteins such as S4 (RpS4) and S9(RpS9) are structural constituents of the ribosome involved in protein biosynthesis and which are components of the cytosolic small ribosomal subunit, the ribosomal proteins such as L9 and L19 are structural constituent of ribosome involved in protein biosynthesis which is localized to the ribosome. The beta-coatamer gene in *C. elegans* encodes a protein which is a subunit of a multimeric complex that forms a membrane vesicle coat. Similar sequences have been found in diverse organisms such as *Arabidopsis thaliana, Drosophila melanogaster*, and *Saccharomyces cerevisiae*. Related sequences are found in diverse organisms such as *Leptinotarsa decemlineata, Phaedon cochleariae, Epilachna varivetis, Anthonomus grandis, Tribolium castaneum, Myzus persicae, Nilaparvata lugens, Chilo suppressalis, Plutella xylostella* and *Acheta domesticus*. Other target genes for use with the methods described herein can include, for example, those that play important roles in viability, growth, survival, development, reproduction, and infectivity. These target genes include, for example, house keeping genes, transcription factors, and insect specific genes or lethal knockout mutations in *Caenorhabditis* or *Drosophila*. The target genes for use with the methods described herein can also be those that are from other organisms, e.g., from a nematode (e.g., *Meloidogyne* spp. or *Heterodera* spp.), other insects or arachnidae (e.g. *Leptinotarsa* spp., *Phaedon* spp., *Epilachna* spp., *Anthonomus* spp., *Tribolium* spp., *Myzus* spp., *Nilaparvata* spp., *Chilo* spp., *Plutella* spp., or *Acheta* spp.

In one embodiment, the target gene is a gene which can induces cell death (e.g., apoptosis). The gene can be directly responsible for inducing apoptosis or can be a gene that indirectly induces apoptosis, e.g., by affecting activity of other genes leading to apoptosis. As used herein, a gene directly induces apoptosis when expression of the gene leads to cell death. A gene indirectly induces apoptosis when expression of the gene modulates the expression of other genes that induce apoptosis.

Additionally, the nucleotide sequences for use as a target sequence in the methods described herein can also be derived from viral, bacterial, insect or fungal genes whose functions have been established from literature and the nucleotide sequences of which share substantial similarity with the target genes in the genome of an insect.

For many of the insects that are potential targets for control by the present invention, there may be limited information regarding the sequences of most genes or the phenotype resulting from mutation of particular genes. Therefore, genes can be selected based on available information available concerning corresponding genes in a model organism, such as *Caenorhabditis* or *Drosophila*, or in some other insect species. Genes can also be selected based on available sequence information for other species, such as nematode or fungal species, in which the genes have been characterized. In some cases it will be possible to obtain the sequence of a corresponding gene from a target insect by searching databases, such as GenBank, using either the name of the gene or the gene sequence. Once the sequence is obtained, PCR can be used to amplify an appropriately selected segment of the gene in the insect for use in the present invention.

In one embodiment, the expression of a target gene is modulated such that the insect has an increased susceptibility to a pathogen. Target genes that can be inhibited to increase pathogen susceptibility include those that confer immunity to the insect and/or are a part of the insect immune system. Alternatively, one can select a target gene in the insect to be activated by RNA activation that is involved in the uptake, reproduction, or virulence of the pathogen in the host. In such an example, the expression of a receptor necessary for uptake of a pathogen in the insect or the expression of a protein involved in viral reproduction would speed up infection and reproduction of a virus, resulting in enhanced pathogen susceptibility. One of skill in the art can determine which gene products of the immune system can be inhibited, or which gene products involved in a pathogen life cycle can be activated in the insect host. Exemplary genes involved in pathogen-borne disease in honeybees can be found in e.g., Navajas, M et al., *BMC Genomics* 2008; 9:301. Other exemplary genes can be found in e.g., Feldhaar, and Gross. *Microbes and Infection* 2008; 10(9):1082-1088. In addition, the genetic structure of the innate immune system is well-conserved in insects, which permits one of skill in the art to determine an appropriate gene target from the sequence of the *Drosophila* genome.

Beneficial Insects

The methods and compositions described herein can be formulated for treating or preventing disease in beneficial insects. As used herein, the term "beneficial insect" is used to describe an insect that provides benefit to humans, mammals, an ecosystem and/or the environment by e.g., pollinating crops, spreading seeds, reducing numbers of pest insects, providing a useable product (e.g., honey, beeswax, silk, etc.). It is contemplated that many of the insects in the list of pests can also be beneficial in particular embodiments. The term "beneficial" and "pest" are determined by one of skill in the art with reference to the occurrence of a desired outcome. For example, silkworms can be beneficial should one desire to produce silk products, however silkworms can also be a pest for those interested in growing mulberry leaves (i.e., a preferred source of food for the silkworm). Thus, for a desired outcome, one of skill in the art can determine if an insect is beneficial or a pest.

Exemplary "beneficial insects" include e.g., ladybugs, bees, wasps, ants and butterflies. As used herein, the term "bee" is defined as any of several winged, hairy-bodied, usually stinging insects of the superfamily Apoidea in the order Hymenoptera, including both solitary and social species and characterized by sucking and chewing mouthparts for gathering nectar and pollen. Exemplary bee species include, but are not limited to *Apis, Bombus, Trigona*, Osmia and the like. In one embodiment, bees include, but are not limited to bumblebees (*Bombus terrestris*) and honeybees (*Apis mellifera*).

Target Pathogens

As used herein, the term "pathogen" is defined as a nucleic acid-containing agent capable of proliferation within a beneficial insect and/or colony, the pathogen causing disease in an insect and/or colonies (e.g., a virus, a bacteria, a mite, a spore, a parasite, and a fungus). In one embodiment, the insect pathogen is a bee pathogen. A bee or bee colony pathogenic agent can be an intracellular or extracellular parasite. According to one embodiment of the invention, the pathogen is a "bee pathogen", causing or facilitating a bee or bee colony disease, such as Colony Collapse Disorder, Sacbrood virus disease, Deformed Wing Disease, Cloudy Wing Disease, Chronic Paralysis, Nosemosis, American Foul Brood and the like.

The importance of honeybees and other pollinating insects to the global world economy far surpasses their contribution in terms of honey production. The United States Department of Agriculture (USDA) estimates that every third bite we consume in our diet is dependent on a honeybee to pollinate that food. The total contribution of pollination in terms of added value to fruit crops exceeds $15 billion per annum, with indirect potential consequence of $75 billion dollars.

The health and vigor of honeybee colonies are threatened by numerous parasites and pathogens, including viruses, bacteria, protozoa, fungi, and mites, each with characteristic modes of transmission.

In general, transmission of viruses can occur via two pathways: horizontal and vertical transmission. In horizontal transmission, viruses are transmitted among individuals of the same generation, while vertical transmission occurs from adults to their offspring. Transmission can occur through multiple routes in social organisms (for a detailed review see Chen Y P, et al (2006) Appl Environ Microbiol. 72(1):606-11). Recently, horizontal transmission of honeybee viruses has been documented in bee colonies, for example, transmission of deformed wing virus (DWV) and Kashmir Bee Virus (KBV) by the parasitic mite *Varroa destructor*, as well as some evidence of virus in honeybee eggs and young larvae, life stages not parasitized by *Varroa* mites. Vertical transmission of multiple viruses from mother queens to their offspring in honeybees has also been recently demonstrated, as well as viruses in feces of queens, suggesting a role for feeding in virus transmission. Moreover, honeybee viruses have been detected in tissues of the gut, suggesting that viruses could be ingested by queens from contaminated foods and passed into the digestive tract, which then acts as a major reservoir for viral replication. Indeed, viruses might penetrate the gut wall and move into the insect hemocoel, spreading infections to other tissues.

In honeybees viruses often persist as latent infections. Thus, group living activities such as trophylaxis and nurse bee brood feeding, can potentially drive high levels of horizontal transmission or amplification of existing infections.

Colony Collapse Disorder (CCD) of honeybees is threatening to annihilate U.S. and world agriculture. Indeed, in the recent outbreak of CCD in the U. S in the winter of 2006-2007, an estimated 25% or more of the 2.4 million honeybee hives were lost because of CCD. An estimated 23% of beekeeping operations in the United States suffered from CCD over the winter of 2006-2007, affecting an average of 45% of the beekeepers operations. In the winter of 2007-2008, the CCD action group of the USDA-ARS estimated that a total of 36% of all hives from commercial operations were destroyed by CCD.

CCD is characterized by the rapid loss from a colony of its adult bee population, with dead adult bees usually found at a distance from the colony. At the final stages of collapse, a queen is attended only by a few newly emerged adult bees. Collapsed colonies often have considerable capped brood and food reserves. The phenomenon of CCD was first reported in 2006; however, beekeepers noted unique colony declines consistent with CCD as early as 2004. Various factors such as mites and infectious agents, weather patterns, electromagnetic (cellular antennas) radiation, pesticides, poor nutrition and stress have been postulated as causes. To date, control of CCD has focused on *varroa* mite control, sanitation and removal of affected hives, treating for opportunistic infections (such as *Nosema*) and improved nutrition. No effective preventative measures have been developed to date.

That CCD is due to the introduction of a previously unrecognized infectious agent is supported by preliminary evidence that CCD is transmissible through the reuse of equipment from CCD colonies and that such transmission can be broken by irradiation of the equipment before use.

Recently, Israeli acute paralysis virus of bees (IAPV, SEQ ID NO: 1), was strongly correlated with CCD. In contrast, IAPV was not only found in 83% of CCD colonies, but was almost completely absent from apparently healthy colonies. Moreover, it was recently shown that when injected or fed to the bees, IAPV causes paralysis and death in 98% of bees within days, further confirming IAPV as the infective agent in CCD.

Israeli acute paralysis virus (IAPV) has been characterized as a bee-affecting dicistrovirus. Recently, DNA versions of genomic segments of non-retro RNA viruses have been found in their respective host genomes, and the reciprocal exchange of genome sequences between host and virus has been demonstrated (Maori et al. Virology 2007; 362:342). These authors showed that the bees who harbored integrated viral sequences were found to be resistant to subsequent viral infection, and a RNAi mechanism of resistance was postulated. A metagenomic survey has indicated a close association between CCD and IAPV (Cox-Foster et al., Science, 2007; 318:283). It thus follows that prevention of IAPV infection using the methods and compositions described herein may prevent development of CCD, significantly improving the state of the beekeeping industry and world agriculture.

According to some embodiments of the invention, the virus is Israel Acute Paralysis Virus and said polypeptide of said virus is selected from the group consisting of IAPV polymerase polyprotein and IAPV structural polyprotein. In further embodiments, other IAPV polypeptides (including viral nucleic acid sequences detected in honeybee nucleic acid) can be targeted for gene modulation as described in the International PCT Publication WO2009/060429, filed Nov. 3, 2008 (Inventor: Paldi, N et al.), which is herein incorporated by reference in its entirety.

Administration to Insects

An insect (e.g., a pest insect or a beneficial insect) can be exposed to an oligonucleotide in combination with a delivery agent in any suitable manner that permits administering the composition to the insect. For example, the insect can be contacted with the composition in a pure or substantially pure form, for example a solution containing the oligonucleotide. Preferably, the composition comprises at a minimum, an oligonucleotide and a delivery agent. In one embodiment, the insect can be simply "soaked" or "sprayed" with a solution comprising the oligonucleotide.

Alternatively, the oligonucleotide can be linked to a food component of the insect, such as a food component for a mammalian pathogenic insect and/or agricultural pest for ease of delivery and/or in order to increase uptake of the oligonucleotide by the insect. Ingestion by an insect permits delivery of the insect control agents and results in modulation of a target gene in the host. Methods for oral introduction include, for example, directly mixing an oligonucleotide with the insect's food, spraying the oligonucleotide in the insect's habitat or field, as well as engineered approaches in which a species that is used as food is engineered to express an oligonucleotide, then fed to the insect to be affected. For example, a bacterium, such as *Lactobacillus*, can be transformed with a target sequence and then fed to an insect. In one embodiment, for example, the oligonucleotide composition can be incorporated into, or overlaid on the top of, the insect's diet. For example, the oligonucleotide composition can be sprayed onto a field of crops which a pest insect attacks.

The oligonucleotide can also be incorporated in the medium in which the insect grows, lives, reproduces, feeds, or infests. For example, an oligonucleotide can be incorporated into a food container or protective wrapping as a means for inhibiting pest infestation. Wood, for example, can be treated with a solution comprising an oligonucleotide to prevent pest infestation.

In other embodiments, the oligonucleotide is expressed in a bacterial or fungal cell and the bacterial or fungal cell is taken up or eaten by the insect species. Bacteria can be engineered to produce any of the oligonucleotide or oligonucleotide constructs contemplated herein. These bacteria can be eaten by the insect species, When taken up, the oligonucleotide can initiate gene expression modulation and can lead to e.g., degradation of the target mRNA and weakening, killing of a pest or decreasing pathogen susceptibility of a beneficial insect.

In some embodiments, the oligonucleotide composition is sprayed directly onto a plant e.g., crops, by e.g., backpack spraying, aerial spraying, crop spraying/dusting etc. In another embodiment, an oligonucleotide producing bacteria or yeast cells can be sprayed directly onto the crops.

Some bacteria have a very close interaction with the host plant, such as, but not limited to, symbiotic *Rhizobium* with the Legminosea (for example Soy). Such recombinant bacteria could be mixed with the seeds (for instance as a coating) and used as soil improvers.

A virus such as a baculovirus which specifically infects insects can also be used. This ensures safety for mammals, especially humans, since the virus will not infect the mammal, so no unwanted gene modulation effect will occur.

Possible applications include intensive greenhouse cultures, for instance crops that are less interesting from a GMO point of view, as well as broader field crops such as soy.

A composition can be a coating or a powder that can be applied to a substrate as a means for protecting the substrate from infestation by an insect and thereby preventing pest-induced damage to the substrate or material. Thus, in one embodiment, the composition is in the form of a coating on a suitable surface which adheres to, and is eventually ingested by an insect which comes into contact with the coating. Such a composition can be used to protect any substrate or material that is susceptible to infestation by or damage caused by a pest, for example foodstuffs and other perishable materials, and substrates such as wood.

For example, the composition can be a liquid that is brushed or sprayed onto or imprinted into the material or substrate to be treated. Thus, a human user can spray the insect or the substrate directly with the composition. For example, houses and other wood products can be destroyed by termites, powder post beetles, and carpenter ants. By treating wood or house siding with a composition comprising an oligonucleotide, it can be possible to reduce pest infestation. Likewise, a tree trunk can be treated with a composition comprising an oligonucleotide.

Flour beetles, grain weevils, meal moths, and other pests feed on stored grain, cereals, pet food, powdered chocolate, and almost everything else in the kitchen pantry that is not protected. Accordingly, the present invention provides a means for treating cereal boxes and other food storage containers and wrapping with a composition comprising an oligonucleotide composition.

Larvae of clothes moths eat clothes made from animal products, such as fur, silk and wool. Thus, it can be desirable to treat hangers, closet organizers, and garment bags with the oligonucleotide as described herein. Book lice and silverfish are pests of libraries because they eat the starchy glue in the bindings of books. Accordingly, the present invention provides compositions for treating books from pest infestation and destruction.

In one embodiment, the composition is in the form of a bait. The bait is designed to lure the insect to come into contact with the composition. In one embodiment, upon coming into contact therewith, the composition is then internalized by the insect, by ingestion for example and mediates modulation of gene expression to thus kill, or otherwise affect the insect. The bait can depend on the species being targeted. An attractant can also be used. The attractant can be a pheromone, such as a male or female pheromone. The attractant acts to lure the insect to the bait, and can be targeted for a particular insect or can attract a whole range of insects. The bait can be in any suitable form, such as a solid, paste, pellet or powdered form.

The bait can also be carried away by the insect back to the colony. The bait can then act as a food source for other members of the colony, thus providing an effective control of a large number of insects and potentially an entire insect pest colony. This is an advantage associated with use of the oligonucleotide or bacteria expressing the oligonucleotide as described herein, because the delayed action of the gene modulation effects on the pests allows the bait to be carried back to the colony, thus delivering maximal impact in terms of exposure to the insects.

The baits can be provided in a suitable "housing" or "trap". Such housings and traps are commercially available and existing traps can be adapted to include the compositions of the invention. The housing or trap can be box-shaped for example, and can be provided in preformed condition or can be formed of foldable cardboard for example. Suitable materials for a housing or trap include plastics and cardboard, particularly corrugated cardboard. The inside surfaces of the traps can be lined with a sticky substance in order to restrict movement of the insect once inside the trap. The housing or trap can contain a suitable trough inside which can hold the bait in place. A trap is distinguished from a housing because the insect can not readily leave a trap following entry, whereas a housing acts as a "feeding station" which provides the insect with a preferred environment in which they can feed and feel safe from predators.

It is clear that numerous products and substrates can be treated with the inventive compositions for reducing pest infestation. Of course, the nature of the excipients and the physical form of the composition can vary depending upon the nature of the substrate that is desired to be treated. For example, the composition can be a liquid that is brushed or sprayed onto or imprinted into the material or substrate to be treated, or a coating that is applied to the material or substrate to be treated.

The compositions described herein can further be delivered to beneficial insects (e.g., bees) as described above. The following exemplary methods and compositions provided for bees can be extended to other beneficial insects by one of skill in the art.

Bee Pathogens and Administration to Bees

As used herein, the term "bee" is defined as any of several winged, hairy-bodied, usually stinging insects of the superfamily Apoidea in the order Hymenoptera, including both solitary and social species and characterized by sucking and chewing mouthparts for gathering nectar and pollen. Exemplary bee species include, but are not limited to *Apis, Bombus, Trigona, Osmia* and the like. In one embodiment, bees include, but are not limited to bumblebees (*Bombus terrestris*) and honeybees (*Apis mellifera*).

As used herein, the term "colony" is defined as a population of dozens to typically several tens of thousand honeybees that cooperate in nest building, food collection, and brood rearing. A colony normally has a single queen, the remainder of the bees being either "workers" (females) or "drones" (males). The social structure of the colony is maintained by the queen and workers and depends on an effective system of communication. Division of labor within the worker caste primarily depends on the age of the bee but varies with the needs of the colony. Reproduction and colony strength depend on the queen, the quantity of food stores, and the size of the worker force. Honeybees can also be subdivided into the categories of "hive bees", usually for the first part of a workers lifetime, during which the "hive bee" performs tasks within the hive, and "forager bee", during the latter part of the bee's lifetime, during which the "forager" locates and collects pollen and nectar from outside the hive, and brings the nectar or pollen into the hive for consumption and storage.

As used herein, the term "tolerance" is defined as the ability of a bee or bee colony to resist infestation by and/or proliferation of a pathogen, including, but not limited to, degree of infection, severity of symptoms, infectivity to other individuals (contagion), and the like. Tolerance can be assessed, for example, by monitoring infectivity, presence of symptoms or time course of a disease in a population following a challenge with the pathogen.

As used herein, the term "pathogen" is defined as a nucleic acid-containing agent capable of proliferation within the bee and/or bee colony, the pathogen causing disease in bees or bee colonies, especially, but not exclusively, a virus, a bacteria and a fungus. A bee or bee colony pathogenic agent can be an intracellular or extra-cellular parasite. According to one embodiment of the invention, the pathogen is a "bee pathogen", causing or facilitating a bee or bee colony disease, such as Colony Collapse Disorder, Sacbrood virus disease, Deformed Wing Disease, Cloudy Wing Disease, Chronic Paralysis, Nosemosis, American Foul Brood and the like.

As used herein, the terms "bee disease" or "bee colony disease" are defined as undesirable changes in the behavior, physiology, morphology, reproductive fitness, economic value, honey production, pollination capability, resistance to infection and/or infestation of a bee, a population of bees and/or a bee colony, directly or indirectly resulting from contact with a bee or bee colony pathogenic agent.

As detailed herein, bee feeding is common practice amongst bee-keepers, for providing both nutritional and other, for example, supplemental needs. Bees typically feed on honey and pollen, but have been known to ingest non-natural feeds as well. Bees can be fed various foodstuffs including, but not limited to Wheast (a dairy yeast grown on cottage cheese), soybean flour, yeast (e.g. brewer's yeast, torula yeast) and yeast products-fed singly or in combination and soybean flour fed as a dry mix or moist cake inside the hive or as a dry mix in open feeders outside the hive. Also useful is sugar, or a sugar syrup. The addition of 10 to 12 percent pollen to a supplement fed to bees can be used improve palatability. The addition of 25 to 30 percent pollen can be used to improve the quality and quantity of essential nutrients that are required by bees for vital activity.

Cane or beet sugar, isomerized corn syrup, and type-50 sugar syrup can be substituted for honey in the natural diet of honey bees. The last two can be supplied as a liquid to bees. Liquid feed can be supplied to bees inside the hive by, for example, any of the following methods: friction-top pail, combs within the brood chamber, division board feeder, boardman feeder, etc. Dry sugar can be fed by placing a pound or two on an inverted inner cover. A supply of water can be provided to the bees. In one embodiment, pans or trays in which floating supports—such as wood chips, cork, or plastic sponge—are present are envisaged. Detailed descriptions of supplemental feeds for bees can be found in, for example, USDA publication by Standifer, et al 1977, entitled "Supplemental Feeding of Honey Bee Colonies" (USDA, Agriculture Information Bulletin No. 413).

Bees in a hive are potentially susceptible to the pathogenic diseases described above. Thus, according to some embodiments, the bees can be honeybees, forager bees, hive bees and the like.

Methods for reducing the susceptibility of a bee colony or bee-hive to bee pathogens by feeding oligonucleotides and/or polynucleotides are envisaged. Thus, in some embodiments, the present invention can be used to benefit any numbers of bees, from a few in the hive, to the entire bee population within a hive and its surrounding area. It will be appreciated, that in addition to feeding of oligonucleotides and/or polynucleotides for reduction of the bee pathogen infection and infestation, enforcement of proper sanitation (for example, refraining from reuse of infested hives) can augment the effectiveness of treatment and prevention of infections.

According to an aspect of some embodiments of the present invention there is provided a method for increasing the tolerance of a bee to a disease caused by a pathogen comprising feeding the bee an effective amount of the oligonucleotide comprising a nucleic acid sequence down-regulating expression of a gene product of a bee pathogen or a nucleic acid construct comprising the oligonucleotide, thereby increasing the tolerance of the bee to the pathogen.

According to a further aspect of some embodiments described herein there is provided a method for increasing the tolerance of a bee colony to a disease caused by a pathogen comprising feeding bees of the colony an effective amount of the oligonucleotide composition comprising a nucleic acid sequence down-regulating expression of a gene product of a bee pathogen or a nucleic acid construct comprising the oligonucleotide, thereby increasing the tolerance of the colony to the pathogen.

According to some embodiments of the invention the bee is a honeybee, including e.g., a forager, a drone bee, a hive bee or a queen bee. In some embodiments a composition comprising an oligonucleotide is administered to bees to treat and/or prevent Colony Collapse Disorder, and/or infection by Israel Acute Paralysis Virus.

According to some embodiments of the invention the feeding comprises providing a liquid bee-ingestible composition or a solid bee-ingestible composition.

The methods and compositions described herein can also be used to increase the tolerance of bees to Colony Collapse Disorder (CCD), the method comprising feeding to the honeybee hive an effective amount of an oligonucleotide (e.g., double stranded ribonucleic nucleic acid (RNA), said double stranded RNA being homologous to a contiguous sequence of at least 21 nucleotides of Israel Acute Paralysis Virus) and a delivery agent.

A non-limiting list of exemplary disease-causing pathogens, and diseases of bees and bee colonies associated with the pathogenic agents, suitable for treatment according to some embodiments of the methods and compositions of the present invention is found in Table I below. The complete genomes of several known isolates of IAPV and information on possible phylogenic relationships between strains that can be similarly targeted with the methods and compositions of the present invention are provided in Palacios et al. 2008 (published online ahead of print on 23 Apr. 2008, Journal of Virology)

According to yet another embodiment of the present invention, synthesis of RNA silencing agents suitable for use with the present invention can be effected according to bee pathogen target sequences known to integrate into the host genome, target sequences suspected associated with resistance to a bee pathogen infection, target sequences representing intergenic regions of the bee pathogen genome and pathogen-specific sequences shown to be critical for pathogen growth and/or replication. It will be appreciated that, in a further embodiment of the present invention, oligonucleotides targeted to sequences having a conserved homology between different strains of the bee pathogen, or even between diverse bee pathogens, once such sequences are

TABLE I

Bee and Bee Colony Pathogens Parasitic Organism Genes
Parasitic Organism Genes

| | |
|---|---|
| Acute bee paralysis virus | Acute bee paralysis virus, complete genome. Accession NC_002548 |
| Israel acute paralysis virus | Accession: NC_009025, israel acute paralysis virus of bees, complete genome |
| Deformed wing virus | Deformed wing virus, complete genome. Accession NC_004830 |
| Kashmir bee virus | Accession: AY275710, kashmir bee virus, complete genome |
| Black queen cell virus | Black queen cell virus strain poland-6 non-structural polyprotein and structural polyprotein genes, complete cds. Accession: EF517521 |
| Chronic paralysis virus | Chronic bee paralysis virus rna 2, complete sequence. Accession: NC_010712 |
| Cloudy wing virus | Cloudy wing virus rna polymerase (pol) gene, partial cds. Accession AF034543 |
| *Paenibacillus* larvae (American Foul Brood) | Accession: NZ_AARF01000646, whole genome (shotgun) sequenced. |
| *Melissococcus pluton* (European Foul Brood) | Accession: EF666055 *Melissococcus plutonius* superoxide dismutase (soda) gene |
| *Nosema apis*, | 1) Accession DQ996230, *Nosema apis* RNA polymerase II largest subunit 2) Accessions EU545140, EF584425, EF584423, EF584418 all are 16S ribosomal RNA gene |
| *Nosema cerana* | EF091883, EF091884, and EF091885 are accessions of 5S ribosomal RNA gene, intergenic spacer, and small subunit ribosomal RNA gene. |

For example, a suitable bee pathogen siRNA can be an IAPV-specific oligonucleotide corresponding to IAPV sequences as described in WO2009/060429, which is herein incorporated by reference in its entirety. Additional suitable bee pathogen siRNAs can be designed according to sequences from any bee pathogens, for example, the sequences detailed in Table I, including, but not limited to Acute Bee Paralysis Virus, Deformed Wing Virus, Kashmir Bee Virus, Black Queen Cell Virus, Chronic Paralysis Virus, Cloudy Wing Virus, *Paenibacillus larvae, Melissococcus pluton, Nosema apis*, and *Nosema cerana* (described in WO2009/064029, herein incorporated by reference in its entirety.

Multiple bee-pathogen sequences can be designed to include sequences suitable for producing oligonucleotides effective against more than one bee pathogen, such as the multiple bee-virus dsRNA described in detail in WO2009/064029, herein incorporated by reference in its entirety. Such multiple bee-pathogen dsRNA can be of the long or short variety, and can include sequences corresponding to homologous sequences within a class of bee pathogens (multiple bee-virus sequences, for example), or sequences corresponding to diverse classes of pathogens (e.g. viral+bacterial+fungal sequences, etc). Further, multiple sequences can be designed to include two or more oligonucleotides (e.g., dsRNA sequences) of the same bee-pathogen.

identified, can be effective against more than one strain of the bee pathogen, or even against different bee pathogens.

For example, a suitable antisense oligonucleotide targeted against the IAPV mRNA would be of the sequences as described in WO2009/064029, herein incorporated by reference in its entirety.

Transgenic Plants

In another aspect, the oligonucleotide can be administered to the insect via contact with a plant expressing the oligonucleotide. The plant can be engineered to express the oligonucleotide in all or some tissues via transformation with an appropriate construct In one embodiment, the insect can be a pest insect which ingests a part of the plant. Alternatively, the insect can have a beneficial function, and comes into contact with the oligonucleotide expressed in the plant or a portion thereof (e.g., the oligonucleotide can be expressed in the pollen).

The term "transgenic plant cell" or "transgenic plant" refers to a plant cell or a plant that expresses an oligonucleotide, as that term is used herein. The transgenic plants are also meant to comprise progeny (decedent, offspring, etc.) of any generation of such a transgenic plant or a seed of any generation of all such transgenic plants wherein said progeny or seed comprises an oligonucleotide, or fragment thereof.

A transgenic plant formed using *Agrobacterium* transformation methods typically contains a single simple recombinant DNA sequence inserted into one chromosome and is referred to as a transgenic event. Such transgenic plants can be referred to as being heterozygous for the inserted exogenous sequence. A transgenic plant homozygous with respect to a transgene can be obtained by sexually mating (selfing) an independent segregant transgenic plant that contains a single exogenous gene sequence to itself, for example an F0 plant, to produce F1 seed. One fourth of the F1 seed produced will be heterozygous with respect to the transgene. Germinating F1 seed results in plants that can be tested for heterozygosity, typically using a SNP assay or a thermal amplification assay that allows for the distinction between heterozygotes and homozygotes (i.e., a zygosity assay). Crossing a heterozygous plant with itself or another heterozygous plant results in only heterozygous progeny.

In addition to direct transformation of a plant with a recombinant DNA construct, transgenic plants can be prepared by crossing a first plant having a recombinant DNA construct with a second plant lacking the construct. For example, recombinant DNA for gene suppression can be introduced into a first plant line that is amenable to transformation to produce a transgenic plant which can be crossed with a second plant line to introgress the recombinant DNA for gene suppression into the second plant line.

Transgenic plants, that can be generated for use with the methods and compositions described herein include, but are not limited to, alfalfa, aneth, apple, apricot, artichoke, arugula, asparagus, avocado, banana, barley, beans, beet, blackberry, blueberry, broccoli, brussel sprouts, cabbage, canola, cantaloupe, carrot, cassaya, cauliflower, celery, cherry, cilantro, citrus, clementine, coffee, corn, cotton, cucumber, Douglas fir, eggplant, endive, escarole, eucalyptus, fennel, figs, gourd, grape, grapefruit, honey dew, jicama, kiwifruit, lettuce, leeks, lemon, lime, Loblolly pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, turf, a vine, watermelon, wheat, yams, and zucchini.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to *Agrobacterium*-mediated transformation, electroporation, microinjection, microprojectile bombardment calcium-phosphate-DNA co-precipitation or liposome-mediated transformation of a heterologous nucleic acid. The transformation of the plant is preferably permanent, i.e. by integration of the introduced expression constructs into the host plant genome, so that the introduced constructs are passed onto successive plant generations.

Any promoter capable of driving expression in the plant of interest may be used in the practice of the invention. The promoter may be native or analogous or foreign or heterologous to the plant host. The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to that sequence.

Promoters active in photosynthetic tissue in order to drive transcription in green tissues such as leaves and stems are of particular interest for the present invention. Most suitable are promoters that drive expression only or predominantly in such tissues. The promoter may confer expression constitutively throughout the plant, or differentially with respect to the green tissues, or differentially with respect to the developmental stage of the green tissue in which expression occurs, or in response to external stimuli.

Examples of such promoters include the ribulose-1,5-bisphosphate carboxylase (RbcS) promoters such as the RbcS promoter from eastern larch (*Larix laricina*), the pine cab6 promoter (Yamamoto et al. (1994) Plant Cell Physiol. 35:773-778), the Cab-1 gene promoter from wheat (Fejes et al. (1990) Plant Mol. Biol. 15:921-932), the CAB-1 promoter from spinach (Lubberstedt et al. (1994) Plant Physiol. 104:997-1006), the cabl R promoter from rice (Luan et al. (1992) Plant Cell 4:971-981), the pyruvate orthophosphate dikinase (PPDK) promoter from corn (Matsuoka et al. (1993) Proc Natl Acad Sci USA 90:9586-9590), the tobacco Lhcb1*2 promoter (Cerdan et al. (1997) Plant Mol. Biol. 33:245-255), the *Arabidopsis thaliana* SUC2 sucrose-H+ symporter promoter (Truernit et al. (1995) Planta 196:564-570), and thylakoid membrane protein promoters from spinach (psaD, psaF, psaE, PC, FNR, atpC, atpD, cab, rbcS. Other promoters that drive transcription in stems, leafs and green tissue are described in U.S. Patent Publication No. 2007/0006346. The TrpA promoter is a pith preferred promoter and has been described in U.S. Pat. No. 6,018,104.

A maize gene encoding phosphoenol carboxylase (PEPC) has been described by Hudspeth & Grula (Plant Molec Biol 12: 579-589 (1989)). Using standard molecular biological techniques the promoter for this gene can be used to drive the expression of any gene in a green tissue-specific manner in transgenic plants.

In some other embodiments of the present invention, inducible promoters may be desired. Inducible promoters drive transcription in response to external stimuli such as chemical agents or environmental stimuli. For example, inducible promoters can confer transcription in response to hormones such as giberellic acid or ethylene, or in response to light or drought.

Oligonucleotides

In the context of this invention, the term "oligonucleotide" refers to a polymer or oligomer of nucleotide or nucleoside monomers consisting of naturally occurring bases, sugars and intersugar (backbone) linkages. The term "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

The oligonucleotide as used herein can be single-stranded or double-stranded. A single-stranded oligonucleotide can have double-stranded regions and a double-stranded oligonucleotide can have single-stranded regions. Exemplary oligonucleotides include, but are not limited to structural genes, genes including control and termination regions, self-replicating systems such as viral or plasmid DNA, single-stranded and double-stranded siRNAs and other RNA interference reagents (RNAi agents or iRNA agents), shRNA, antisense oligonucleotides, ribozymes, microRNAs, microRNA mimics, supermirs, aptamers, antimirs, antagomirs, triplex-forming oligonucleotides, RNA activators, and decoy oligonucleotides.

Double-stranded and single-stranded oligonucleotides that are effective in inducing RNA interference are also referred to as siRNA, RNAi agent, or iRNA agent, herein. These RNA interference inducing oligonucleotides associate with a cytoplasmic multi-protein complex known as RNAi-induced silencing complex (RISC). In many embodiments, single-stranded and double-stranded RNAi agents are sufficiently long that they can be cleaved by an endogenous molecule, e.g. by Dicer, to produce smaller oligonucleotides that can enter the RISC machinery and participate in RISC mediated cleavage of a target sequence, e.g. a target mRNA.

Oligonucleotides of the present invention can be of various lengths. In particular embodiments, oligonucleotides can range from about 10 to 100 nucleotides in length. In various related embodiments, oligonucleotides, single-stranded, double-stranded, and triple-stranded, can range in length from about 10 to about 50 nucleotides, from about 20 to about 50 nucleotides, from about 15 to about 30 nucleotides, from about 20 to about 30 nucleotides in length. In certain embodiments, oligonucleotide is from about 9 to about 39 nucleotides in length. In some other embodiments, oligonucleotide is at least 30 nucleotides in length.

The oligonucleotides of the invention can comprise any oligonucleotide modification described herein and below. In certain instances, it can be desirable to modify one or both strands of a double-stranded oligonucleotide. In some cases, the two strands will include different modifications. In other instances, multiple different modifications can be included on each of the strands. The various modifications on a given strand can differ from each other, and can also differ from the various modifications on other strands. For example, one strand can have a modification, e.g., a modification described herein, and a different strand can have a different modification, e.g., a different modification described herein. In other cases, one strand can have two or more different modifications, and the another strand can include a modification that differs from the at least two modifications on the first strand.

Double-Stranded Oligonucleotides

The skilled person is well aware that double-stranded oligonucleotides comprising a duplex structure of between 20 and 23, but specifically 21, base pairs have been characterized as particularly effective in inducing RNA interference (Elbashir et al., EMBO 2001, 20:6877-6888). However, others have found that shorter or longer double-stranded oligonucleotides can be effective as well.

The double-stranded oligonucleotides comprise two oligonucleotide strands that are sufficiently complementary to hybridize to form a duplex structure. Generally, the duplex structure is between 15 and 30, more generally between 18 and 25, yet more generally between 19 and 24, and most generally between 19 and 21 base pairs in length. In certain embodiments, longer double-stranded oligonucleotides of between 25 and 30 base pairs in length are preferred. In certain embodiments, shorter double-stranded oligonucleotides of between 10 and 15 base pairs in length are preferred. In another embodiment, the double-stranded oligonucleotide is at least 21 nucleotides long.

In one embodiment, the double-stranded oligonucleotide comprises a sense strand and an antisense strand, wherein the antisense RNA strand has a region of complementarity which is complementary to at least a part of a target sequence, and the duplex region is 14-30 nucleotides in length. Similarly, the region of complementarity to the target sequence is between 14 and 30, more generally between 18 and 25, yet more generally between 19 and 24, and most generally between 19 and 21 nucleotides in length.

By "target sequence" or "target gene" is meant any nucleic acid sequence whose expression or activity is to be modulated. The target nucleic acid can be DNA or RNA, such as endogenous DNA or RNA, viral DNA or viral RNA, or other RNA encoded by a gene, virus, bacteria, fungus, insect or plant.

Suitable oligonucleotides can be designed according to the target sequence. Various methods and tools are available to one of skill in the art to design siRNAs and antisense oligonucleotides that can target a given target sequence. Exemplary insect and insect pathogen sequences to be target include, but are not limited, Acute bee paralysis virus (accession: NC_002548, Israel acute paralysis virus, (accession: NC_009025), Deformed wing virus (accession: NC_004830, Kashmir bee virus (accession: AY275710), Black queen cell virus (accession: EF517521), Chronic paralysis virus (accession: NC_010712), Cloudy wing virus (accession: AF034543), *Paenibacillus larvae* (accession: NZ_AARF01000646), *Melissococcus pluton* (European Foul Brood, accession: EF666055), *Ascosphaera apis* (Chalkbrood), *Nosema apis* (accession: DQ996230, EU545140, EF584425, EF584423 and EF584418), *Nosema cerana* (accession: EF091883, EF091884, and EF091885), *Spodoptera frugiperda* ascovirus 1a (accession: NC008361), *Triatoma* virus (accession: NC003783 and AF178440), HZ-1 insect virus late gene (accession: L8840), *Autographa californica* nuclear polyhedrosis virus helicase gene (M57687), *Spodoptera frugiperda* ascovirus 1a (accession: AM398843), *Nudaureila capensis* omega virus capid protein (accession: S43937), and *Trichoplusia ni* granulovirus (accession: AF079223).

By "complementarity" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al, 1987, CSHSymp. Quant. Biol. LII pp. 123-133; Frier et al., 1986, *Proc. Nat. Acad. Sci. USA* 83:9373-9377; Turner et al., 1987, /. *Am. Chem. Soc.* 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence.

In many embodiments, the double-stranded oligonucleotide is sufficiently large that it can be cleaved by an endogenous molecule, e.g., by Dicer, to produce smaller double-stranded oligonucleotides, e.g., RNAi agents. In one embodiment, the double-stranded oligonucleotide modulates the expression of a target gene via RISC mediated cleavage of the target sequence.

In certain embodiments, the double-stranded region of a double-stranded oligonucleotide is equal to or at least, 10, 11, 12, 13, 14, 15, 16, 17, 18, 19, 20, 21, 22, 23, 23, 24, 25, 26, 27, 28, 29, or 30 nucleotide pairs in length.

In certain embodiments, the antisense strand of a double-stranded oligonucleotide is equal to or at least 14, 15, 16, 17, 18, 19, 20, 21, 22, 23, 23, 24, 25, 26, 27, 28, 29, or 30 nucleotides in length.

In certain embodiments, the sense strand of a double-stranded oligonucleotide is equal to or at least 10, 11, 12, 13, 14, 15, 16, 17, 18, 19, 20, 21, 22, 23, 23, 24, 25, 26, 27, 28, 29, or 30 nucleotides in length.

In certain embodiments, one strand has at least one stretch of 1-5 single-stranded nucleotides in the double-stranded region. In certain other embodiments, both strands have at least one stretch of 1-5 single-stranded nucleotides in the double stranded region. When both strands have a stretch of 1-5 single-stranded nucleotides in the double stranded region, such single-stranded nucleotides can be opposite to each other or they can be located such that the second strand has no single-stranded nucleotides opposite to the single-stranded oligonucleotides of the first strand and vice versa.

In certain embodiments, each strand of the double-stranded oligonucleotide has a ZXY structure, such as is described in PCT Application No. PCT/US2004/07070 filed on Mar. 8, 2004, contents of which are hereby incorporated in their entireties.

Hairpins and Dumbbells

The present invention also includes double-stranded oligonucleotide wherein the two strands are linked together. The two strands be linked to each other at both ends, or at one end only. The two strands can be linked together by an oligonucleotide linker including, but not limited to, (N)$_n$; wherein N is independently a modified or unmodified nucleotide and n is 3-23. Some of the nucleotides in the linker can be involved in base-pair interactions with other nucleotides in the loop. The two strands can also be linked together by a non-nucleosidic linker, e.g. a linker described herein. It will be appreciated by one of skill in the art that any oligonucleotide chemical modifications or variations describe herein can be used in the oligonucleotide linker.

Hairpin and dumbbell type RNAi agents will have a duplex region equal to or at least 14, 15, 16, 17, 18, 19, 20, 21, 22, 23, 24, or 25 nucleotide pairs. The duplex region can be equal to or less than 200, 100, or 50, in length. In certain embodiments, ranges for the duplex region are 15-30, 17 to 23, 19 to 23, and 19 to 21 nucleotides pairs in length.

The hairpin RNAi agents can have a single strand overhang or terminal unpaired region, in some embodiments at the 3', and in certain embodiments on the antisense side of the hairpin. In certain embodiments, the overhangs are 1-4, more generally 2-3 nucleotides in length.

The hairpin oligonucleotides are also referred to as "shRNA" herein.

Single-Stranded Oligonucleotides

The single-stranded oligonucleotides of the present invention also comprise nucleotide sequence that is substantially complementary to a "sense" nucleic acid encoding a gene expression product, e.g., complementary to the coding strand of a double-stranded cDNA molecule or complementary to an RNA sequence, e.g., a pre-mRNA, mRNA, miRNA, or pre-miRNA. The single-stranded oligonucleotides of the invention include antisense oligonucleotides, single-stranded RNAi agents, antimirs and triplex forming oligonucleotides. The region of complementarity can be less than 30 nucleotides in length, and at least 15 nucleotides in length. Generally, the single stranded oligonucleotides are 10 to 25 nucleotides in length (e.g., 11, 12, 13, 14, 15, 16, 17, 18, 19, 20, 21, 22, 23, or 24 nucleotides in length). In one embodiment the strand is 25-30 nucleotides. In one embodiment, the single-stranded oligonucleotide is 15-29 nucleotides in length. Single strands having less than 100% complementarity to the target mRNA, RNA or DNA are also embraced by the present invention. In certain embodiments, the single-stranded oligonucleotide has a ZXY structure, such as is described in PCT Application No. PCT/US2004/07070 filed on Mar. 8, 2004.

The single-stranded oligonucleotide can hybridize to a complementary RNA, e.g., mRNA, pre-mRNA, and prevent access of the translation machinery to the target RNA transcript, thereby preventing protein synthesis. The single-stranded oligonucleotide can also hybridize to a complementary RNA and the RNA target can be subsequently cleaved by an enzyme such as RNase H and thus preventing translation of target RNA. In other embodiments, the single-stranded oligonucleotide modulates the expression of a target gene via RISC mediated cleavage of the target sequence.

A "single-stranded RNAi agent" as used herein, is an RNAi agent which is made up of a single molecule. A single-stranded RNAi agent can include a duplexed region, formed by intra-strand pairing, e.g., it can be, or include, a hairpin or pan-handle structure. Single-stranded RNAi agents can be antisense with regard to the target molecule. A single-stranded RNAi agent can be sufficiently long that it can enter the RISC and participate in RISC mediated cleavage of a target mRNA.

A single-strand RNAi agent is at least 14, and in other embodiments at least 15, at least 20, at least 25, at least 29, at least 35, at least 40, or at least 50 nucleotides in length. In certain embodiments, it is less than 200, 100, or 60 nucleotides in length. In certain embodiments single-stranded RNAi agents are 5' phosphorylated or include a phosphoryl analog at the 5' prime terminus.

In certain embodiments, single-stranded RNAi agents and/or at least one strand of the double-stranded RNAi agent, includes at least one of the following motifs:

(a) 5'-phosphorothioate or 5'-phosphorodithioate;
(b) a cationic modification of nucleotides 1 and 2 on the 5' terminal, wherein the cationic modification is at C5 position of pyrimidines and C2, C6, C8, exocyclic N2 or exocyclic N6 of purines;
(c) at least one G-clamp nucleotide in the first two terminal nucleotides at the 5' end and the other nucleotide having a cationic modification, wherein the cationic modification is at C5 position of pyrimidines or C2, C6, C8, exocyclic N2 or exocyclic N6 position of purines;
(d) at least one 2'-F modified nucleotide comprising a nucleobase base modification;
(e) at least one gem-2'-O-methyl/2'-F modified nucleotide comprising a nucleobase modification, preferably the methyl substituent is in the up configuration, e.g. in the arabinose configuration;
(f) a 5'-PuPu-3' dinucleotide at the 3' terminal wherein both nucleotides comprise a modified MOE at 2'-position as described in U.S. Provisional Application No. 61/226,017 filed Jul. 16, 2009;
(g) a 5'-PuPu-3' dinucleotide at the 5' terminal wherein both nucleotides comprise a modified MOE at 2'-position as described in U.S. Provisional Application No. 61/226,017 filed Jul. 16, 2009;
(h) nucleotide at the 5' terminal having a modified MOE at 2'-position as described in U.S. Provisional Application No. 61/226,017 filed Jul. 16, 2009;
(i) nucleotide at the 5' terminal having a 3'-F modification;

(j) 5' terminal nucleotide comprising a 4'-substituent;
(k) 5' terminal nucleotide comprising a replacement of O4' with N(alkyl), S or $CH_2$;
(l) 3' terminal nucleotide comprising a 4'-substituent; and
(m) combinations thereof.

MicroRNAs

MicroRNAs (miRNAs or mirs) are a highly conserved class of small RNA molecules that are transcribed from DNA in the genomes of plants and animals, but are not translated into protein. Pre-microRNAs are processed into miRNAs. Processed microRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

MicroRNAs have also been implicated in modulation of pathogens in hosts. For example, see Jopling, C. L., et al., Science (2005) vol. 309, pp 1577-1581. Without wishing to be bound by theory, administration of a microRNA, microRNA mimic, and/or anti microRNA oligonucleotide, leads to modulation of pathogen viability, growth, development, and/or replication.

In certain embodiments, the oligonucleotide is a microRNA, microRNA mimic, and/or anti microRNA, wherein microRNA is a host microRNA.

The number of miRNA sequences identified to date is large and growing, illustrative examples of which can be found, for example, in: "*miRBase: microRNA sequences, targets and gene nomenclature*" Griffiths-Jones S, Grocock R J, van Dongen S, Bateman A, Enright A J. NAR, 2006, 34, Database Issue, D140-D144; "*The microRNA Registry*" Griffiths-Jones S. NAR, 2004, 32, Database Issue, D109-D111; and also on the worldwide web at microrna.dot.sanger.dot.ac.dot.uk/sequences/.

Ribozymes

Ribozymes are oligonucleotides having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). At least six basic varieties of naturally-occurring enzymatic RNAs are known presently. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Methods of producing a ribozyme targeted to any target sequence are known in the art. Ribozymes can be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein.

Aptamers

Aptamers are nucleic acid or peptide molecules that bind to a particular molecule of interest with high affinity and specificity (Tuerk and Gold, Science 249:505 (1990); Ellington and Szostak, Nature 346:818 (1990)). DNA or RNA aptamers have been successfully produced which bind many different entities from large proteins to small organic molecules. See Eaton, Curr. Opin. Chem. Biol. 1:10-16 (1997), Famulok, Curr. Opin. Struct. Biol. 9:324-9(1999), and Hermann and Patel, Science 287:820-5 (2000). Aptamers can be RNA or DNA based. Generally, aptamers are engineered through repeated rounds of in vitro selection or equivalently, SELEX (systematic evolution of ligands by exponential enrichment) to bind to various molecular targets such as small molecules, proteins, nucleic acids, and even cells, tissues and organisms. The aptamer can be prepared by any known method, including synthetic, recombinant, and purification methods, and can be used alone or in combination with other aptamers specific for the same target. Further, as described more fully herein, the term "aptamer" specifically includes "secondary aptamers" containing a consensus sequence derived from comparing two or more known aptamers to a given target.

Decoy Oligonucleotides

Because transcription factors recognize their relatively short binding sequences, even in the absence of surrounding genomic DNA, short oligonucleotides bearing the consensus binding sequence of a specific transcription factor can be used as tools for manipulating gene expression in living cells. This strategy involves the intracellular delivery of such "decoy oligonucleotides", which are then recognized and bound by the target factor. Occupation of the transcription factor's DNA-binding site by the decoy renders the transcription factor incapable of subsequently binding to the promoter regions of target genes. Decoys can be used as therapeutic agents, either to inhibit the expression of genes that are activated by a transcription factor, or to upregulate genes that are suppressed by the binding of a transcription factor. Examples of the utilization of decoy oligonucleotides can be found in Mann et al., J. Clin. Invest., 2000, 106: 1071-1075, which is expressly incorporated by reference herein, in its entirety.

miRNA Mimics miRNA mimics represent a class of molecules that can be used to imitate the gene modulating activity of one or more miRNAs. Thus, the term "microRNA mimic" refers to synthetic non-coding RNAs (i.e. the miRNA is not obtained by purification from a source of the endogenous miRNA) that are capable of entering the RNAi pathway and regulating gene expression. miRNA mimics can be designed as mature molecules (e.g. single stranded) or mimic precursors (e.g., pri- or pre-miRNAs).

In one design, miRNA mimics are double stranded molecules (e.g., with a duplex region of between about 16 and about 31 nucleotides in length) and contain one or more sequences that have identity with the mature strand of a given miRNA. Double-stranded miRNA mimics have designs similar to as described above for double-stranded oligonucleotides.

In one embodiment, a miRNA mimic comprises a duplex region of between 16 and 31 nucleotides and one or more of the following chemical modification patterns: the sense strand contains 2'-O-methyl modifications of nucleotides 1 and 2 (counting from the 5' end of the sense oligonucleotide), and all of the Cs and Us; the antisense strand modifications can comprise 2' F modification of all of the Cs and Us, phosphorylation of the 5' end of the oligonucleotide, and stabilized internucleotide linkages associated with a 2 nucleotide 3' overhang.

Supermirs

A supermir refers to an oligonucleotide, e.g., single stranded, double stranded or partially double stranded, which has a nucleotide sequence that is substantially identical to an miRNA and that is antisense with respect to its target. This term includes oligonucleotides which comprise at least one non-naturally-occurring portion which functions similarly. In a preferred embodiment, the supermir does not include a sense strand, and in another preferred embodiment, the supermir does not self-hybridize to a significant extent. An supermir featured in the invention can have secondary structure, but it is substantially single-stranded under physiological conditions. A supermir that is substantially single-stranded is single-stranded to the extent that less than about 50% (e.g., less than about 40%, 30%, 20%, 10%, or 5%) of the supermir is duplexed with itself. The supermir can include a hairpin segment, e.g., sequence, preferably at the 3' end can self hybridize and form a duplex region, e.g., a duplex region of at least 1, 2, 3, or 4 and preferably less than 8, 7, 6, or 5 nucleotides, e.g., 5 nucleotides. The duplexed region can be connected by a linker, e.g., a nucleotide linker, e.g., 3, 4, 5, or 6 dTs, e.g., modified dTs. In another embodiment the supermir is duplexed with a shorter oligo, e.g., of 5, 6, 7, 8, 9, or 10 nucleotides in length, e.g., at one or both of the 3' and 5' end or at one end and in the non-terminal or middle of the supermir.

Antimirs or miRNA Inhibitors

The terms "antimir" "microRNA inhibitor" or "miR inhibitor" are synonymous and refer to oligonucleotides or modified oligonucleotides that interfere with the activity of specific miRNAs. Inhibitors can adopt a variety of configurations including single stranded, double stranded (RNA/RNA or RNA/DNA duplexes), and hairpin designs, in general, microRNA inhibitors comprise one or more sequences or portions of sequences that are complementary or partially complementary with the mature strand (or strands) of the miRNA to be targeted, in addition, the miRNA inhibitor can also comprise additional sequences located 5' and 3' to the sequence that is the reverse complement of the mature miRNA. The additional sequences can be the reverse complements of the sequences that are adjacent to the mature miRNA in the pri-miRNA from which the mature miRNA is derived, or the additional sequences can be arbitrary sequences (having a mixture of A, G, C, U, or dT). In some embodiments, one or both of the additional sequences are arbitrary sequences capable of forming hairpins. Thus, in some embodiments, the sequence that is the reverse complement of the miRNA is flanked on the 5' side and on the 3' side by hairpin structures. MicroRNA inhibitors, when double stranded, can include mismatches between nucleotides on opposite strands. Furthermore, microRNA inhibitors can be linked to conjugate moieties in order to facilitate uptake of the inhibitor into a cell.

MicroRNA inhibitors, including hairpin miRNA inhibitors, are described in detail in Vermeulen et al., "Double-Stranded Regions Are Essential Design Components Of Potent Inhibitors of RISC Function," RNA 13: 723-730 (2007) and in WO2007/095387 and WO 2008/036825 each of which is incorporated herein by reference in its entirety. A person of ordinary skill in the art can select a sequence from the database for a desired miRNA and design an inhibitor useful for the methods disclosed herein.

Antagomirs

Antagomirs are RNA-like oligonucleotides that harbor various modifications for RNAse protection and pharmacologic properties, such as enhanced tissue and cellular uptake. They differ from normal RNA by, for example, complete 2'-O-methylation of sugar, phosphorothioate backbone and, for example, a cholesterol-moiety at 3'-end. In a preferred embodiment, antagomir comprises a 2'-O-methylmodification at all nucleotides, a cholesterol moiety at 3'-end, two phosphorothioate backbone linkages at the first two positions at the 5'-end and four phosphorothioate linkages at the 3'-end of the molecule. Antagomirs can be used to efficiently silence endogenous miRNAs by forming duplexes comprising the antagomir and endogenous miRNA, thereby preventing miRNA-induced gene silencing. An example of antagomir-mediated miRNA silencing is the silencing of miR-122, described in Krutzfeldt et al, Nature, 2005, 438: 685-689, which is expressly incorporated by reference herein in its entirety.

RNA Activators

Recent studies have found that dsRNA can also activate gene expression, a mechanism that has been termed "small RNA-induced gene activation" or RNAa. See for example Li, L. C. et al. *Proc Natl Acad Sci USA*. (2006), 103(46): 17337-42 and Li L. C. (2008). "Small RNA-Mediated Gene Activation". RNA and the Regulation of Gene Expression: A Hidden Layer of Complexity. Caister Academic Press. ISBN 978-1-904455-25-7. It has been shown that dsRNAs targeting gene promoters induce potent transcriptional activation of associated genes. Endogenous miRNA that cause RNAa have also been found in humans. Check E. Nature (2007). 448 (7156): 855-858.

Another surprising observation is that gene activation by RNAa is long-lasting. Induction of gene expression has been seen to last for over ten days. The prolonged effect of RNAa could be attributed to epigenetic changes at dsRNA target sites.

In certain embodiments, the oligonucleotide is an RNA activator, wherein the oligonucleotide increases the expression of a gene. In one embodiment, increased gene expression inhibits viability, growth development, and/or reproduction of a pest insect or an insect pathogen.

Triplex Forming Oligonucleotides

Studies have shown that triplex forming oligonucleotides (TFO) can be designed which can recognize and bind to polypurine/polypyrimidine regions in double-stranded helical DNA in a sequence-specific manner. These recognition rules are outline by Maher III, L. J., et al., *Science* (1989) vol. 245, pp 725-730; Moser, H. E., et al., *Science* (1987) vol. 238, pp 645-630; Beal, P. A., et al., *Science* (1992) vol. 251, pp 1360-1363; Conney, M., et al., *Science* (1988) vol. 241, pp 456-459 and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 1 12:487-94). In general, the triplex-forming oligonucleotide has the sequence correspondence:

```
oligo   3'-A G G T duplex  5'-A G C T duplex  3'-T C G A
```

However, it has been shown that the A-AT and G-GC triplets have the greatest triple helical stability (Reither and Jeltsch, BMC Biochem, 2002 Sep. 12, Epub). The same authors have demonstrated that TFOs designed according to the A-AT and G-GC rule do not form non-specific triplexes, indicating that the triplex formation is indeed sequence specific.

Thus for any given sequence a triplex forming sequence can be devised. Triplex-forming oligonucleotides preferably are at least 15, more preferably 25, still more preferably 30 or more nucleotides in length, up to 50 or 100 nucleotides.

Formation of the triple helical structure with the target DNA induces steric and functional changes, blocking transcription initiation and elongation, allowing the introduction of desired sequence changes in the endogenous DNA and resulting in the specific down-regulation of gene expression. Examples of such suppression of gene expression in cells treated with TFOs include knockout of episomal supFGl and endogenous HPRT genes in mammalian cells (Vasquez et al., Nucl Acids Res. 1999; 27: 1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-I gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both down-regulation and up-regulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn, contents of which are herein incorporated in their entireties.

Oligonucleotide Modifications

Unmodified oligonucleotides can be less than optimal in some applications, e.g., unmodified oligonucleotides can be prone to degradation by e.g., cellular nucleases. However, chemical modifications to one or more of the subunits of oligonucleotide can confer improved properties, e.g., can render oligonucleotides more stable to nucleases. Typical oligonucleotide modifications can include one or more of: (i) alteration, e.g., replacement, of one or both of the non-linking phosphate oxygens and/or of one or more of the linking phosphate oxygens in the phosphodiester backbone linkage; (ii) alteration, e.g., replacement, of a constituent of the ribose sugar, e.g., of the 2' hydroxyl on the ribose sugar; (iii) wholesale replacement of the phosphate moiety with "dephospho" linkers; (iv) modification or replacement of a naturally occurring base with a non-natural base; (v) replacement or modification of the ribose-phosphate backbone, e.g. peptide nucleic acid (PNA); (vi) modification of the 3' end or 5' end of the oligonucleotide, e.g., removal, modification or replacement of a terminal phosphate group or conjugation of a moiety, e.g., conjugation of a ligand, to either the 3' or 5' end of oligonucleotide; and (vii) modification of the sugar, e.g., six membered rings.

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule. As described below, modifications, e.g., those described herein, can be provided as asymmetrical modifications.

A modification described herein can be the sole modification, or the sole type of modification included on multiple nucleotides, or a modification can be combined with one or more other modifications described herein. The modifications described herein can also be combined onto an oligonucleotide, e.g. different nucleotides of an oligonucleotide have different modifications described herein.

In certain embodiments, the oligonucleotide is a modified oligonucleotide in that the oligonucleotide comprises at least one modification, e.g., sugar modification, non-phosphodiester backbone linkage and/or nucleobase modification.

The Phosphate Group

The phosphate group can be modified by replacing one of the oxygens with a different substituent. One result of this modification to RNA phosphate backbones can be increased resistance of the oligonucleotide to nucleolytic breakdown. Examples of modified phosphate groups include phosphorothioate, phosphoroselenates, borano phosphates, borano phosphate esters, hydrogen phosphonates, phosphoroamidates, alkyl or aryl phosphonates and phosphotriesters. In certain embodiments, one of the non-bridging phosphate oxygen atoms in the phosphate backbone moiety can be replaced by any of the following: S, Se, $BR_3$ (R is hydrogen, alkyl, aryl), C (i.e. an alkyl group, an aryl group, etc.), H, $NR_2$ (R is hydrogen, optionally substituted alkyl, aryl), or OR (R is optionally substituted alkyl or aryl). The phosphorous atom in an unmodified phosphate group is achiral. However, replacement of one of the non-bridging oxygens with one of the above atoms or groups of atoms renders the phosphorous atom chiral; in other words a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligonucleotides diastereomers. Thus, while not wishing to be bound by theory, modifications to both non-bridging oxygens, which eliminate the chiral center, e.g. phosphorodithioate formation, can be desirable in that they cannot produce diastereomer mixtures. Thus, the non-bridging oxygens can be independently any one of O, S, Se, B, C, H, N, or OR (R is alkyl or aryl).

The phosphate linker can also be modified by replacement of bridging oxygen, (i.e. oxygen that links the phosphate to the nucleoside), with nitrogen (bridged phosphoroamidates), sulfur (bridged phosphorothioates) and carbon (bridged methylenephosphonates). The replacement can occur at the either one of the linking oxygens or at both linking oxygens. When the bridging oxygen is the 3'-oxygen of a nucleoside, replacement with carbon is preferred. When the bridging oxygen is the 5'-oxygen of a nucleoside, replacement with nitrogen is preferred.

Modified phosphate linkages where at least one of the oxygen linked to the phosphate has been replaced or the phosphate group has been replaced by a non-phosphorous group, are also referred to as "non-phosphodiester backbone linkage" or "non-phosphodiester linker."

Replacement of the Phosphate Group

The phosphate group can be replaced by non-phosphorus containing connectors, e.g. dephospho linkers. Dephospho linkers are also referred to as non-phosphodiester linkers herein. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include, but are not limited to, amides (for example amide-3 (3'-$CH_2$—C(=O)—N(H)-5') and amide-4 (3'-$CH_2$—N(H)—C(=O)-5')), hydroxylamino, siloxane (dialkylsiloxxane), carboxamide, carbonate, carboxymethyl, carbamate, carboxylate ester, thioether, ethylene oxide linker, sulfide, sulfonate, sulfonamide, sulfonate ester, thioformacetal (3'-S—$CH_2$—O-5'), formacetal (3'-O—$CH_2$—O-5'), oxime, methyleneimino, methykenecarbonylamino, methylenemethylimino (MMI, 3'-$CH_2$—N($CH_3$)—O-5'), methylenehydrazo, methylenedimethylhydrazo, methyleneoxymethylimino, ethers (C3'-O—C5'), thioethers (C3'-S—C5'), thioacetamido (C3'-N(H)—C(=O)—$CH_2$—S—C5', C3'-O—P(O)—O—SS—C5', C3'-$CH_2$—NH—NH—C5', 3'-NHP(O)(O$CH_3$)—O-5' and 3'-NHP(O)(O$CH_3$)—O-5' and nonionic linkages containing mixed N, O, S and $CH_2$ component parts. See for example, Carbohydrate Modifications in Antisense Research; Y. S. Sanghvi and P. D. Cook Eds. ACS Symposium Series 580; Chapters 3 and 4, (pp. 40-65). Preferred embodiments include methylenemethylimino (MMI), methylenecarbonylamino, amides, carbamate and ethylene oxide linker.

One skilled in the art is well aware that in certain instances replacement of a non-bridging oxygen can lead to enhanced cleavage of the backbone linkage by the neighboring 2'-OH, thus in many instances, a modification of a non-bridging oxygen can necessitate modification of 2'-OH, e.g., a modification that does not participate in cleavage of the neighboring backbone linkage, e.g. a "2'-deoxy" modification, e.g., arabinose sugar, 2'-O-alkyl, 2'-F, LNA and ENA.

Preferred non-phosphodiester backbone linkages include phosphorothioates, phosphorothioates with an at least 1%, 5%, 10%, 20%, 30%, 40%, 50%, 60%, 70%, 80%, 90% 95% or more enantiomeric excess of Sp isomer, phosphorothioates with an at least 1%, 5%, 10%, 20%, 30%, 40%, 50%, 60%, 70%, 80%, 90% 95% or more enantiomeric excess of Rp isomer, phosphorodithioates, phsophotriesters, aminoalkylphosphotrioesters, alkyl-phosphonaters (e.g., methylphosphonate), selenophosates, phosphoramidates (e.g., N-alkylphosphoramidate), and boranophosphonates.

Replacement of Ribophosphate Backbone

Oligonucleotide-mimicking scaffolds can also be constructed wherein the phosphate linker and ribose sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone. Examples include the morpholino, cyclobutyl, pyrrolidine, peptide nucleic acid (PNA), aminoethylglycyl PNA (aegPNA) and backbone-extended pyrrolidine PNA (bepPNA) nucleoside surrogates. A preferred surrogate is a PNA surrogate.

Sugar Modifications

An oligonucleotide can include modification of all or some of the sugar groups of the nucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2'-alkoxide ion. The 2'-alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), O($CH_2CH_2O$)$_n CH_2CH_2OR$, n=1-50; "locked" nucleic acids (LNA) in which the oxygen at the 2' position is connected by ($CH_2$)$_n$, wherein n=1-4, to the 4' carbon of the same ribose sugar, preferably n is 1 (LNA) or 2 (ENA); O-AMINE or O—($CH_2$)$_n$AMINE (n=1-10, AMINE=$NH_2$; alkylamino, dialkylamino, heterocyclyl, arylamino, diaryl amino, heteroaryl amino, diheteroaryl amino, ethylene diamine or polyamino); and O—$CH_2CH_2$(NCH$_2$CH$_2$NMe$_2$)$_2$.

"Deoxy" modifications include hydrogen (i.e. deoxyribose sugars, which are of particular relevance to the single-strand overhangs); halo (e.g., fluoro); amino (e.g. $NH_2$; alkylamino, dialkylamino, heterocyclyl, arylamino, diaryl amino, heteroaryl amino, diheteroaryl amino, or amino acid); NH($CH_2CH_2NH$)$_n CH_2CH_2$-AMINE (AMINE=$NH_2$; alkylamino, dialkylamino, heterocyclyl, arylamino, diaryl amino, heteroaryl amino, or diheteroaryl amino); —NHC(O)R (R=alkyl, cycloalkyl, aryl, aralkyl, heteroaryl or sugar); cyano; mercapto; alkyl-thioalkyl; thioalkoxy; thioalkyl; alkyl; cycloalkyl; aryl; alkenyl and alkynyl, which can be optionally substituted with e.g., an amino functionality.

Other suitable 2'-modifications, e.g., modified MOE, are described in U.S. Provisional Application No. 61/226,017 filed Jul. 16, 2009, contents of which are herein incorporated by reference.

A modification at the 2' position can be present in the arabinose configuration The term "arabinose configuration" refers to the placement of a substituent on the C2' of ribose in the same configuration as the 2'-OH is in the arabinose.

The sugar group can comprise two different modifications at the same carbon in the sugar, e.g., gem modification. The sugar group can also contain one or more carbons that possess the opposite stereochemical configuration than that of the corresponding carbon in ribose. Thus, an oligonucleotide can include nucleotides containing e.g., arabinose, as the sugar. The monomer can have an alpha linkage at the 1' position on the sugar, e.g., alpha-nucleosides. The monomer can also have the opposite configuration at the 4'-position, e.g., C5' and H4' or substituents replacing them are interchanged with each other. When the C5' and H4' or substituents replacing them are interchanged with each other, the sugar is said to be modified at the 4' position.

Oligonucleotides can also include "abasic" sugars, which lack a nucleobase at C-1'. These abasic sugars can also be further containing modifications at one or more of the constituent sugar atoms. Oligonucleotides can also contain one or more sugars that are the L isomer, e.g. L-nucleosides. Modification to the sugar group can also include replacement of the 4'-O with a sulfur, optionally substituted nitrogen or CH$_2$ group. In certain embodiments, linkage between C1' and nucleobase is in the α configuration.

Modifications can also include acyclic nucleotides, wherein at least one of ribose carbons (C1', C2', C3', C4' or C5') are independently or in combination absent from the nucleotide, e.g., acyclic nucleotide. In certain embodiments, acyclic nucleotide is

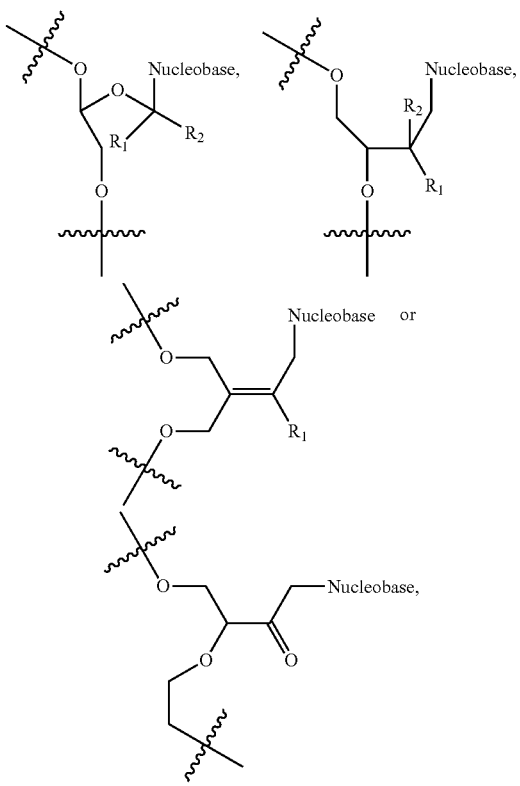

wherein R$_1$ and R$_2$ independently are H, halogen, OR$_3$, or alkyl; and R$_3$ is H, alkyl, cycloalkyl, aryl, aralkyl, heteroaryl or sugar).

Preferred sugar modifications are 2'-H, 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH$_2$-(4'-C) (LNA), 2'-O—CH$_2$CH$_2$-(4'-C) (ENA), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE) and gem 2'-OMe/2'F with 2'-O-Me in the arabinose configuration.

It is to be understood that when a particular nucleotide is linked through its 2'-position to the next nucleotide, the sugar modifications described herein can be placed at the 3% position of the sugar for that particular nucleotide, e.g., the nucleotide that is linked through its 2'-position. A modification at the 3' position can be present in the xylose configuration The term "xylose configuration" refers to the placement of a substituent on the C3' of ribose in the same configuration as the 3'-OH is in the xylose sugar.

The hydrogen attached to C4' and/or C1' can be replaced by a straight- or branched-optionally substituted alkyl, optionally substituted alkenyl, optionally substituted alkynyl, wherein backbone of the alkyl, alkenyl and alkynyl can contain one or more of O, S, S(O), SO$_2$, N(R'), C(O), N(R')C(O)O, OC(O)N(R'), CH(Z'), phosphorous containing linkage, optionally substituted aryl, optionally substituted heteroaryl, optionally substituted heterocyclic or optionally substituted cycloalkyl, where R' is hydrogen, acyl or optionally substituted aliphatic, Z' is selected from the group consisting of OR$_{11}$, COR$_{11}$, CO$_2$R$_{11}$.

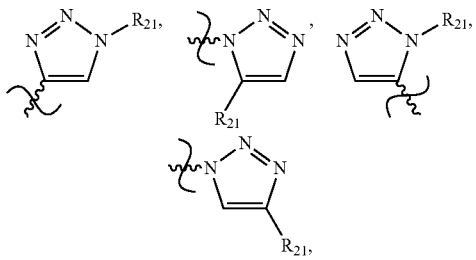

NR$_{21}$R$_{31}$, CONR$_{21}$R$_{31}$, CON(H)NR$_{21}$R$_{31}$, ONR$_{21}$R$_{31}$, CON(H)N=CR$_{41}$R$_{51}$, N(R$_{21}$)C(=NR$_{31}$)NR$_{21}$R$_{31}$, N(R$_{21}$)C(O)NR$_{21}$R$_{31}$, N(R$_{21}$)C(S)NR$_{21}$R$_{31}$, OC(O)NR$_{21}$R$_{31}$, SC(O)NR$_{21}$R$_{31}$, N(R$_{21}$)C(S)OR$_{11}$, N(R$_{21}$)C(O)OR$_{11}$, N(R$_{21}$)C(O)SR$_{11}$, N(R$_{21}$)N=CR$_{41}$R$_{51}$, ON=CR$_{41}$R$_{51}$, SO$_2$R$_{11}$, SOR$_{11}$, SR$_{11}$, and substituted or unsubstituted heterocyclic; R$_{21}$ and R$_{31}$ for each occurrence are independently hydrogen, acyl, unsubstituted or substituted aliphatic, aryl, heteroaryl, heterocyclic, OR$_{11}$, COR$_{11}$, CO$_2$R$_{11}$, or NR$_{11}$R$_{11}$'; or R$_{21}$ and R$_{31}$, taken together with the atoms to which they are attached, form a heterocyclic ring; R$_{41}$ and R$_{51}$ for each occurrence are independently hydrogen, acyl, unsubstituted or substituted aliphatic, aryl, heteroaryl, heterocyclic, OR$_{11}$, COR$_{11}$, or CO$_2$R$_{11}$, or NR$_{11}$R$_{11}$'; and R$_{11}$, and R$_{11}$' are independently hydrogen, aliphatic, substituted aliphatic, aryl, heteroaryl, or heterocyclic. In one embodiment, the hydrogen attached to the C4' of the 5' terminal nucleotide is replaced.

In certain embodiments, C4' and C5' together form an optionally substituted heterocyclic, preferably comprising at least one —PX(Y)—, wherein X is H, OH, OM, SH, optionally substituted alkyl, optionally substituted alkoxy, optionally substituted alkylthio, optionally substituted alkylamino or optionally substituted dialkylamino, where M is independently for each occurrence an alki metal or transition metal with an overall charge of +1; and Y is O, S, or NR', where R' is hydrogen, optionally substituted aliphatic. Preferably this modification is at the 5 terminal of the oligonucleotide.

Terminal Modifications

The 3' and 5' ends of an oligonucleotide can be modified. Such modifications can be at the 3' end, 5' end or both ends of the molecule. For example, the 3' and/or 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs).

When a linker/phosphate-functional molecular entity-linker/phosphate array is interposed between two strands of a dsRNA, this array can substitute for a hairpin RNA loop in a hairpin-type RNA agent.

Terminal modifications useful for modulating activity include modification of the 5' end with phosphate or phosphate analogs. For example, in certain embodiments antisense strands of dsRNAs, are 5' phosphorylated or include a phosphoryl analog at the 5' terminus. 5'-phosphate modifications include those which are compatible with RISC mediated gene silencing. In certain embodiments, the 5'-end of the oligonucleotide comprises the modification

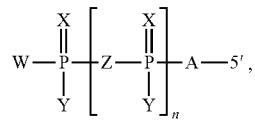

wherein W, X and Y are each independently selected from the group consisting of O, OR (R is hydrogen, alkyl, aryl), S, Se, BR$_3$ (R is hydrogen, alkyl, aryl), BH$_3^-$, C (i.e. an alkyl group, an aryl group, etc. . . . ), H, NR$_2$ (R is hydrogen, alkyl, aryl), or OR (R is hydrogen, alkyl or aryl); A and Z are each independently for each occurrence absent, O, S, CH$_2$, NR (R is hydrogen, alkyl, aryl), or optionally substituted alkylene, wherein backbone of the alkylene can comprise one or more of O, S, SS and NR (R is hydrogen, alkyl, aryl) internally and/or at the end; and n is 0-2. It is understood that A is replacing the oxygen linked to 5' carbon of sugar. When n is 0, W and Y together with the P to which they are attached can form an optionally substituted 5-8 membered heterocyclic, wherein W an Y are each independently O, S, NR' or alkylene. Preferably the heterocyclic is substituted with an aryl or heteroaryl. In certain embodiments, one or both hydrogen on C5' of the 5'-terminal nucleotides are replaced with a halogen, e.g., F.

Exemplary 5'-modifications include, but are not limited to, 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); 5'-alpha-thiotriphosphate; 5'-beta-thiotriphosphate; 5'-gamma-thiotriphosphate; 5'-phosphoramidates ((HO)$_2$(O)P—NH-5', (HO)(NH$_2$)(O)P—O-5'). Other 5'-modification include 5'-alkylphosphonates (R(OH)(O)P—O-5', R=alkyl, e.g., methyl, ethyl, isopropyl, propyl, etc. . . . ), 5'-alkyletherphosphonates (R(OH)(O)P—O-5', R=alkylether, e.g., methoxymethyl (CH$_2$OMe), ethoxymethyl, etc. . . . ). Other exemplary 5'-modifications include where Z is optionally substituted alkyl at least once, e.g., ((HO)$_2$(X)P—O[—(CH$_2$)$_a$—O—P(X)(OH)—O]$_b$-5', ((HO)2(X)P—O[—(CH$_2$)$_a$—P(X)(OH)—O]$_b$-5', ((HO)2(X)P—[—(CH$_2$)$_a$—O—P(X)(OH)—O]$_b$-5'; dialkyl terminal phosphates and phosphate mimics: HO[—(CH$_2$)$_a$—O—P(X)(OH)—O]$_b$-5', H$_2$N[—(CH$_2$)$_a$—O—P(X)(OH)—O]$_b$-5', H[(CH$_2$)$_a$—O—P(X)(OH)—O]$_b$-5', Me$_2$N[—(CH$_2$)$_a$—O—P(X)(OH)—O]$_b$-5', HO[—(CH$_2$)$_a$—P(X)(OH)—O]$_b$-5', H$_2$N[—(CH$_2$)$_a$—P(X)(OH)—O]$_b$-5', H[—(CH$_2$)$_a$—P(X)(OH)—O]$_b$-Me$_2$N[—(CH$_2$)$_a$—P(X)(OH)—O]$_b$-5', wherein a and b are each independently 1-10. Other embodiments, include replacement of oxygen and/or sulfur with BH$_3$, BH$_3^-$ and/or Se.

Terminal modifications can also be useful for monitoring distribution, and in such cases the preferred groups to be added include fluorophores, e.g., fluorescein or an Alexa dye, e.g., Alexa 488. Terminal modifications can also be useful for enhancing uptake, useful modifications for this include targeting ligands. Terminal modifications can also be useful for cross-linking an oligonucleotide to another moiety; modifications useful for this include mitomycin C, psoralen, and derivatives thereof.

Nucleobases

Adenine, cytosine, guanine, thymine and uracil are the most common bases (or nucleobases) found in nucleic acids. These bases can be modified or replaced to provide oligonucleotides having improved properties. For example, nuclease resistant oligonucleotides can be prepared with these bases or with synthetic and natural nucleobases (e.g., inosine, xanthine, hypoxanthine, nubularine, isoguanisine, or tubercidine) and any one of the above modifications. Alternatively, substituted or modified analogs of any of the above bases and "universal bases" can be employed. When a natural base is replaced by a non-natural and/or universal base, the nucleotide is said to comprise a modified nucleobase and/or a nucleobase modification herein. Modified nucleobase and/or nucleobase modifications also include natural, non-natural and universal bases, which comprise conjugated moieties, e.g. a ligand described herein. Preferred conjugate moieties for conjugation with nucleobases include cationic amino groups which can be conjugated to the nucleobase via an appropriate alkyl, alkenyl or a linker with an amide linkage. Examples of non-natural bases include, but are not limited to, 2-(halo)adenine, 2-(alkyl)adenine, 2-(propyl)adenine, 2-(amino)adenine, 2-(aminoalkyl)adenine, 2-(aminopropyl)adenine, 2-(methylthio)-N$^6$-(isopentenyl)adenine, 6-(alkyl)adenine, 6-(methyl)adenine, 7-(deaza)adenine, 8-(alkenyl)adenine, 8-(alkyl)adenine, 8-(alkynyl)adenine, 8-(amino)adenine, 8-(halo)adenine, 8-(hydroxyl)adenine, 8-(thioalkyl)adenine, 8-(thiol)adenine, N$^6$-(isopentyl)adenine, N$^6$-(methyl)adenine, N$^6$, N$^6$-(dimethyl)adenine, 2-(alkyl)guanine, 2-(propyl)guanine, 6-(alkyl)guanine, 6-(methyl)guanine, 7-(alkyl)guanine, 7-(methyl)guanine, 7-(deaza)guanine, 8-(alkyl)guanine, 8-(alkenyl)guanine, 8-(alkynyl)guanine, 8-(amino)guanine, 8-(halo)guanine, 8-(hydroxyl)guanine, 8-(thioalkyl)guanine, 8-(thiol)guanine, N-(methyl)guanine, 2-(thio)cytosine, 3-(deaza)-5-(aza)cytosine, 3-(alkyl)cytosine, 3-(methyl)cytosine, 5-(alkyl)cytosine, 5-(alkynyl)cytosine, 5-(halo)cytosine, 5-(methyl)cytosine, 5-(propynyl)cytosine, 5-(propynyl)cytosine, 5-(trifluoromethyl)cytosine, 6-(azo)cytosine, N$^4$-(acetyl)cytosine, 3-(3-amino-3-carboxypropyl)uracil, 2-(thio)uracil, 5-(methyl)-2-(thio)uracil, 5-(methylaminomethyl)-2-(thio)uracil, 4-(thio)uracil, 5-(methyl)-4-(thio)uracil, 5-(methylaminomethyl)-4-(thio)uracil, 5-(methyl)-2,4-(dithio)uracil, 5-(methylaminomethyl)-2,4-(dithio)uracil, 5-(2-aminopropyl)uracil, 5-(alkyl)uracil, 5-(alkynyl)uracil, 5-(allylamino)uracil, 5-(aminoallyl)uracil, 5-(aminoalkyl)uracil, 5-(guanidiniumalkyl)uracil, 5-(1,3-diazole-1-alkyl)uracil, 5-(cyanoalkyl)uracil, 5-(dialkylaminoalkyl)uracil, 5-(dimethylaminoalkyl)uracil, 5-(halo)uracil, 5-(methoxy)uracil, uracil-5-oxyacetic acid, 5-(methoxycarbonylmethyl)-2-(thio)uracil, 5-(methoxycarbonyl-methyl)uracil, 5-(propynyl)uracil, 5-(propynyl)uracil, 5-(trifluoromethyl)uracil, 6-(azo)uracil, dihydrouracil, N$^3$-(methyl)uracil, 5-uracil (i.e., pseudouracil), 2-(thio)pseudouracil, 4-(thio)pseudouracil, 2,4-(dithio)psuedouracil, 5-(alkyl)pseudouracil, 5-(methyl)pseudouracil, 5-(alkyl)-2-(thio)pseudouracil, 5-(methyl)-2-(thio)pseudouracil, 5-(alkyl)-4-(thio)pseudouracil, 5-(methyl)-4-(thio)pseudouracil, 5-(alkyl)-2,4-(dithio)pseudouracil, 5-(methyl)-2,4-(dithio)pseudouracil, 1-substituted pseudouracil, 1-substituted 2(thio)-pseudouracil, 1-substituted 4-(thio)pseudouracil, 1-substituted 2,4-(dithio) pseudouracil, 1-(aminocarbonylethylenyl)-pseudouracil, 1-(aminocarbonylethylenyl)-2(thio)-pseudouracil, 1-(aminocarbonylethylenyl)-4-(thio)pseudouracil, 1-(aminocarbonylethylenyl)-2,4-(dithio)pseudouracil, 1-(aminoalkylaminocarbonylethylenyl)-pseudouracil, 1-(aminoalkylaminocarbonylethylenyl)-2(thio)-pseudouracil, 1-(aminoalkylaminocarbonylethylenyl)-4-(thio)pseudouracil, 1-(aminoalkylaminocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, difluorotolyl, 4-(fluoro)-6-(methyl)benzimidazole, 4-(methyl)benzimidazole, 6-(azo) thymine, 2-pyridinone, 5-nitroindole, 3-nitropyrrole, 6-(aza) pyrimidine, 2-(amino)purine, 2,6-(diamino)purine, 5-substituted pyrimidines, $N^2$-substituted purines, $N^6$-substituted purines, $O^6$-substituted purines, substituted 1,2,4-triazoles, pyrrolo-pyrimidin-2-on-3-yl, 6-phenyl-pyrrolo-pyrimidin-2-on-3-yl, para-substituted-6-phenyl-pyrrolo-pyrimidin-2-on-3-yl, ortho-substituted-6-phenyl-pyrrolo-pyrimidin-2-on-3-yl, bis-ortho-substituted-6-phenyl-pyrrolo-pyrimidin-2-on-3-yl, para-(aminoalkylhydroxy)-6-phenyl-pyrrolo-pyrimidin-2-on-3-yl, ortho-(aminoalkylhydroxy)-6-phenyl-pyrrolo-pyrimidin-2-on-3-yl, bis-ortho-(aminoalkylhydroxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N-alkylated derivatives thereof.

As used herein, a universal nucleobase is any modified, unmodified, naturally occurring or non-naturally occurring nucleobase that can base pair with all of the four naturally occurring nucleobases without substantially affecting the melting behavior, recognition by intracellular enzymes or activity of the oligonucleotide duplex. Some exemplary universal nucleobases include, but are not limited to, 2,4-difluorotoluene, nitropyrrolyl, nitroindolyl, 8-aza-7-deazaadenine, 4-fluoro-6-methylbenzimidazle, 4-methyl-benzimidazle, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4, 5-trimethylphenyl, 4-methylinolyl, 4,6-dimethylindolyl, phenyl, napthalenyl, anthracenyl, phenanthracenyl, pyrenyl, stilbenyl, tetracenyl, pentacenyl, and structural derivatives thereof (see for example, Loakes, 2001, *Nucleic Acids Research*, 29, 2437-2447).

Further nucleobases include those disclosed in U.S. Pat. No. 3,687,808, hereby incorporated by reference, those disclosed in International Application No. PCT/US09/038425, filed Mar. 26, 2009, hereby incorporated by reference, those disclosed in the Concise Encyclopedia Of Polymer Science And Engineering, pages 858-859, Kroschwitz, J. I., ed. John Wiley & Sons, 1990, and those disclosed by English et al., Angewandte Chemie, International Edition, 1991, 30, 613.

General References

The oligonucleotides used in accordance with this invention can be synthesized with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3, 2'-O-Methyloligoribonucleotides: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chim. Acta*, 1995, 78, 486-504; Beaucage, S. L. and Iyer, R. P., *Tetrahedron*, 1992, 48, 2223-2311 and Beaucage, S. L. and Iyer, R. P., *Tetrahedron*, 1993, 49, 6123-6194, or references referred to therein. Modification described in WO 00/44895, WO01/75164, or WO02/44321 can be used herein. The disclosure of all publications, patents, and published patent applications listed herein are hereby incorporated by reference.

Phosphate Group References

The preparation of phosphinate oligonucleotides is described in U.S. Pat. No. 5,508,270. The preparation of alkyl phosphonate oligonucleotides is described in U.S. Pat. No. 4,469,863. The preparation of phosphoramidite oligonucleotides is described in U.S. Pat. No. 5,256,775 or U.S. Pat. No. 5,366,878. The preparation of phosphotriester oligonucleotides is described in U.S. Pat. No. 5,023,243. The preparation of boranophosphate oligonucleotide is described in U.S. Pat. Nos. 5,130,302 and 5,177,198. The preparation of 3'-Deoxy-3'-amino phosphoramidate oligonucleotides is described in U.S. Pat. No. 5,476,925. 3'-Deoxy-3'-methylenephosphonate oligonucleotides is described in An, H, et al. *J. Org. Chem.* 2001, 66, 2789-2801. Preparation of sulfur bridged nucleotides is described in Sproat et al. *Nucleosides Nucleotides* 1988, 7, 651 and Crosstick et al. *Tetrahedron Lett.* 1989, 30, 4693.

Sugar Group References

Modifications to the 2' modifications can be found in Verma, S. et al. *Annu. Rev. Biochem.* 1998, 67, 99-134 and all references therein. Specific modifications to the ribose can be found in the following references: 2'-fluoro (Kawasaki et. al., *J. Med. Chem.*, 1993, 36, 831-841), 2'-MOE (Martin, P. *Helv. Chim. Acta* 1996, 79, 1930-1938), "LNA" (Wengel, J. *Acc. Chem. Res.* 1999, 32, 301-310).

Replacement of the Phosphate Group References

Methylenemethylimino linked oligonucleosides, also identified herein as MMI linked oligonucleosides, methylenedimethylhydrazo linked oligonucleosides, also identified herein as MDH linked oligonucleosides, and methylenecarbonylamino linked oligonucleosides, also identified herein as amide-3 linked oligonucleosides, and methyleneaminocarbonyl linked oligonucleosides, also identified herein as amide-4 linked oligonucleosides as well as mixed backbone compounds having, as for instance, alternating MMI and PO or PS linkages can be prepared as is described in U.S. Pat. Nos. 5,378,825, 5,386,023, 5,489,677 and in published PCT applications PCT/US92/04294 and PCT/US92/04305 (published as WO 92/20822 WO and 92/20823, respectively). Formacetal and thioformacetal linked oligonucleosides can be prepared as is described in U.S. Pat. Nos. 5,264,562 and 5,264,564. Ethylene oxide linked oligonucleosides can be prepared as is described in U.S. Pat. No. 5,223,618. Siloxane replacements are described in Cormier, J. F. et al. *Nucleic Acids Res.* 1988, 16, 4583. Carbonate replacements are described in Tittensor, J. R. *J. Chem. Soc. C* 1971, 1933. Carboxymethyl replacements are described in Edge, M. D. et al. *J. Chem. Soc. Perkin Trans.* 1 1972, 1991. Carbamate replacements are described in Stirchak, E. P. Nucleic Acids Res. 1989, 17, 6129.

Replacement of the Phosphate-Ribose Backbone References

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They can also be prepared in accordance with U.S. Pat. No. 5,539,083.

Terminal Modification References

Terminal modifications are described in Manoharan, M. et al. Antisense and Nucleic *Acid Drug Development* 12, 103-128 (2002) and references therein.

Nucleobases References

N-2 substituted purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908. Additional references are disclosed in the above section on base modifications.

Placement of Modifications within an Oligonucleotide

As oligonucleotides are polymers of subunits or monomers, many of the modifications described herein can occur at a position which is repeated within an oligonucleotide, e.g., a modification of a nucleobase, a sugar, a phosphate moiety, or the non-bridging oxygen of a phosphate moiety. It is not necessary for all positions in a given oligonucleotide to be uniformly modified, and in fact more than one of the aforementioned modifications can be incorporated in a single oligonucleotide or even at a single nucleoside within an oligonucleotide.

In some cases the modification will occur at all of the subject positions in the oligonucleotide but in many, and in fact in most cases it will not. By way of example, a modification can only occur at a 3' or 5' terminal position, can only occur in the internal region, can only occur in 3', 5' or both terminal regions, e.g. at a position on a terminal nucleotide or in the last 2, 3, 4, 5, 6, 7, 8, 9, or 10 nucleotides of an oligonucleotide. A modification can occur in a double strand region, a single strand region, or in both. A modification can occur only in the double strand region of an oligonucleotide or can only occur in a single strand region of an oligonucleotide. In certain embodiments, a modification described herein does not occur in the region corresponding to the target cleavage site region. For example, a phosphorothioate modification at a non-bridging oxygen position can only occur at one or both termini, can only occur in a terminal regions, e.g., at a position on a terminal nucleotide or in the last 2, 3, 4, 5, 6, 7, 8, 9, or 10 nucleotides of a strand, or can occur in double strand and single strand regions, particularly at termini.

Some modifications can preferably be included on an oligonucleotide at a particular location, e.g., at an internal position of a strand, or on the 5' or 3' end of an oligonucleotide. A preferred location of a modification on an oligonucleotide, can confer preferred properties on the oligonucleotide. For example, preferred locations of particular modifications can confer optimum gene silencing properties, or increased resistance to endonuclease or exonuclease activity.

In certain embodiments, the oligonucleotide comprises at least one of 5'-5', 3'-3', 3'-2', 2'-5', 2'-3' or 2'-2' backbone linkage. In certain embodiments, the last nucleotide on the terminal end is linked via a 5'-5', 3'-3', 3'-2', 2'-5', 2'-3' or 2'-2' backbone linkage to the rest of the oligonucleotide. In some preferred embodiments, the last nucleotide on the terminal end is linked via a 5'-5', 3'-3', 3'-2', 2'-3' or 2'-2' backbone linkage to the rest of the oligonucleotide.

5'-Pyrimidine-Purine-3' and 5'-Pyrimidine-Pyrimidine-3' Dinucleotide Motif

An oligonucleotide can comprise at least 1, 2, 3, 4, 5, 6, 7, 8, 9 or 10, 5'-pyrimidine-purine-3' (5'-PyPu-3') and/or 5'-pyrimidine-pyrimidine-3' (5'-PyPy-3') dinucleotide sequence motif, wherein the 5'-most pyrimidine ribose sugar is modified at the 2'-position. Preferred 2'-modifications include, but are not limited to, 2'-H, 2'-O-Me (2'-O-methyl), 2'-O-MOE (2'-O-methoxyethyl), 2'-F, 2'-O-[2-(methylamino)-2-oxoethyl] (2'-O-NMA), 2'-O—$CH_2CH_2N$($CH_2CH_2NMe_2$)$_2$, 2'-S-methyl, 2'-O—$CH_2$-(4'-C) (LNA) and 2'-O—$CH_2CH_2$-(4'-C) (ENA). Double-stranded oligonucleotides including these modifications are particularly stabilized against endonuclease activity. In one embodiment, the 3' most nucleotide in the dinucleotide motif also comprises a ribose sugar which is modified at the 2'-position. When both nucleotides of the dinucleotide motif comprise ribose sugar with 2'-modification, the modification can be the same or different on the two nucleotides. In another embodiment, the 5' most pyrimidine in all occurrences of the dinucleotide motif in the oligonucleotide comprises a ribose sugar which is modified at the 2'-position. In yet another embodiment, both nucleotides in all occurrences of the dinucleotide motif comprise a ribose sugar comprising a 2'-modification. In yet another embodiment, the 5'-most pyrimidine in the dinucleotide motif is uridine. In yet still another embodiment, the 5'-most pyrimidine in the dinucleotide motif is cytidine.

In certain embodiments, the oligonucleotide comprises at least 1, 2, 3, 4, 5, 6, 7, 8, 9, or 10, 5'-PyPu-3' and/or 5'-PyPy-3' dinucleotide motif wherein the backbone linkage between the two nucleotides is not a phosphodiester. In certain embodiments, the backbone linkage is a non-phosphodiester linkage described herein. Preferred non-phosphodiester backbone linkages include, but are not limited to, phosphorothioate, phosphorodithioate, N-alkyl phosphoramidate, alkyl phosphonate (e.g., methyl phosphonate) and borano phosphonate. In one embodiment, the backbone linkage between the two nucleotides in all occurrences of the dinucleotide motif is a non-phosphodiester linkage. In another embodiment, the 5'-most pyrimidine in the dinucleotide motif is uridine. In yet another embodiment, the 5'-most pyrimidine in the dinucleotide motif is cytidine.

In certain embodiments, the oligonucleotide comprises at least 1, 2, 3, 4, 5, 6, 7, 8, 9, or 10, 5'-PyPu-3' and/or 5'-PyPy-3' dinucleotide motif wherein at least one of the nucleotides comprises a nucleobase modification, e.g. a modified nucleobase or a nucleobase with one or more conjugated moieties. In one embodiment, the 5' most pyrimidine in the dinucleotide sequence motif comprises the nucleobase modification. In another embodiment, the 3' most nucleotide in the dinucleotide motif also comprises the nucleobase modification. In yet another embodiment, both nucleotides in the dinucleotide motif comprise a nucleobase modification. In certain embodiments, at least one nucleotides in all occurrences of the dinucleotide motif comprises a nucleobase modification. In still another embodiment, the 5'-most pyrimidine in the dinucleotide motif is uridine. In yet still another embodiment, the 5'-most pyrimidine in the dinucleotide motif is cytidine.

In certain embodiments, the oligonucleotide comprises at least 1, 2, 3, 4, 5, 6, 7, 8, 9, or 10, 5'-PyPu-3' and/or 5'-PyPy-3' dinucleotide motif wherein the 5'-most pyrimidine ribose sugar is modified at the 2'-position and the oligonucleotide further comprises at least one of a non-phosphodiester backbone linkage, a nucleobase modification or a 2' modification. In one embodiment, the 5'-most pyrimidines in all occurrences of the dinucleotide motif comprise a ribose sugar modified at the 2'-position, and the oligonucleotide further comprises at least one of a non-phosphodiester backbone linkage, a nucleobase modification or a 2' modification. In further embodiments, the non-phosphodiester backbone linkage, the nucleobase modification and/or the 2'-modification is comprised within the dinucleotide motif, e.g. the internucleotide linkage between the two nucleotides of the dinucleotide motif is a non-phosphodiester backbone linkage, one or both nucleotides comprise a nucleobase modification and/or the 3'-nucleotide of the motif comprises a 2'-modification. In one embodiment, the 5'-most pyrimidine in the dinucleotide motif is uridine. In another embodiment, the 5'-most pyrimidine in the dinucleotide motif is cytidine.

In certain embodiments, the oligonucleotide comprises at least 1, 2, 3, 4, 5, 6, 7, 8, 9, 0r 10, 5'-PyPu-3' and/or 5'-PyPy-3' dinucleotide motif, wherein the ribose sugar of the 5'-most pyrimidine is replaced by a non ribose moiety, e.g., a six membered ring. In one embodiment, the 5'-most pyrimidines all occurrences of the dinucleotide motif comprise a non ribose sugar, e.g. a six membered ring. In one embodiment, the 5'-most pyrimidine in the dinucleotide motif is uridine. In another embodiment, the 5'-most pyrimidine in the dinucleotide motif is cytidine.

In certain embodiments, the oligonucleotide comprises at least 1, 2, 3, 4, 5, 6, 7, 8, 9, or 10, 5'-PyPu-3' and/or 5'-PyPy-3' dinucleotide motif wherein the $C^5$ position of the 5'-most pyrimidine is conjugated with a ligand, e.g. a cationic group, e.g. a cationic amino group. In one embodiment, the 5'-most pyrimidines all occurrences of dinucleotide motif are conjugated with a ligand, at the $C^5$ position, wherein each ligand is selected independently of other ligands. In another embodiment, the 5'-most pyrimidine in the dinucleotide motif is uridine. In yet another embodiment, the 5'-most pyrimidine in the dinucleotide motif is cytidine.

In some embodiments, the oligonucleotide comprises at least 1, 2, 3, 4, 5, 6, 7, 8, 9, or 10, 5'-PyPu-3' dinucleotide wherein the $N^2$, $N^6$, and/or $C^8$ position of the purine is conjugated with a ligand, e.g. a cationic group, e.g. a cationic amino group. In one embodiment, the 3'-most purines in all occurrences of the dinucleotide motif are conjugated with a ligand at the $N^2$, $N^6$, and/or $C^8$ positions, wherein each ligand is selected independently of other ligands. In another embodiment, the 5'-most pyrimidine in the dinucleotide motif is uridine. In yet another embodiment, the 5'-most pyrimidine in the dinucleotide motif is cytidine.

In certain embodiments, the oligonucleotide comprises at least 1, 2, 3, 4, 5, 6, 7, 8, 9, or 10, 5'-PyPu-3' and/or 5'-PyPy-3' dinucleotide motif wherein both nucleotides comprise nucleobase modifications, e.g., the $C^5$ position of the pyrimidine and the $N^2$, $N^6$, and/or $C^8$ position of the purine is conjugated with a ligand, e.g. a cationic group, wherein each ligand is selected independently. In one embodiment, both nucleotides in all occurrences of the dinucleotide motif are conjugated with a ligand, wherein each ligand is selected independently of other ligands. In another embodiment, the 5'-most pyrimidine in the dinucleotide motif is uridine. In yet another embodiment, the 5'-most pyrimidine in the dinucleotide motif is cytidine.

In certain embodiments, the oligonucleotide comprises at least 1, 2, 3, 4, 5, 6, 7, 8, 9, or 10, 5'-PyPu-3' and/or 5'-PyPy-3' dinucleotide motif wherein at least one of the nucleotides comprises a nucleobase modification and neither nucleotide comprises a modification at the 2' position of the ribose sugar. In another embodiment, at least one nucleotide in all occurrences of the dinucleotide motif comprise a nucleobase modification and neither nucleotide comprises a modification at the 2' position of the ribose sugar. In yet another embodiment, both nucleotides in the dinucleotide motif comprise a nucleobase modification and neither nucleotide comprises a modification at the 2' position of the ribose sugar.

In certain embodiments, the oligonucleotide comprises at least 1, 2, 3, 4, 5, 6, 7, 8, 9, or 10, 5'-PyPu-3' and/or 5'-PyPy-3' dinucleotide motif wherein the backbone linkage between the two nucleotides is not a phosphodiester and neither nucleotide comprises a modification at the 2' position of the ribose sugar. In certain embodiments, the backbone linkage is a non-phosphodiester linkage described herein. In one embodiment, the backbone linkage between the two nucleotides in all occurrences of the dinucleotide motif is a non-phosphodiester linkage and neither nucleotide comprises a modification at the 2' position of the ribose sugar.

In certain embodiments, the oligonucleotide comprises at least 1, 2, 3, 4, 5, 6, 7, 8, 9, or 10, 5'-PyPu-3' and/or 5'-PyPy-3' dinucleotide motif wherein the 5'-most pyrimidine comprises a modification at the 2'-position, backbone linkage between the two nucleotides is a non-phosphodiester linkage and 'at least one of the nucleotides comprises a nucleobase modification. In one embodiment, the 5' most pyrimidine in the dinucleotide motif comprises the nucleobase modification. In another embodiment, the 3'most nucleotide in the dinucleotide motif comprises the nucleobase modification. In yet another embodiment, both the nucleotides in the dinucleotide motif comprise the nucleobase modification. In yet still another embodiment, the 5'most pyrimidine in all occurrences of the dinucleotide motif comprises a 2'-modified ribose sugar, backbone linkage between the two nucleotides is a non-phosphodiester linkage and at least one of the nucleotides comprises a nucleobase modification.

In certain embodiments, the oligonucleotide comprises at least 1, 2, 3, 4, 5, 6, 7, 8, 9, or 10, 5'-PyPu-3' and/or 5'-PyPy-3'dinucleotide motif wherein the 3' most nucleotide comprises a modification at the 2'-position, backbone linkage between the two nucleotides is a non-phosphodiester linkage and at least one of the nucleotides comprises a nucleobase modification. In one embodiment, the 5'-most nucleotide in the dinucleotide motif comprises the nucleobase modification. In another embodiment, the 3'-most nucleotide in the dinucleotide motif comprises the nucleobase modification. In yet another embodiment, both nucleotides in the dinucleotide comprise the nucleobase modification. In yet still another embodiment, the 3'most nucleotide in all occurrences of the dinucleotide motif comprises a 2'-modified ribose sugar, backbone linkage between the two nucleotides is a non-phosphodiester linkage and at least one of the nucleotides comprises a nucleobase modification.

In one embodiment, oligonucleotide comprises a motif selected from the group consisting of: 2'-modified uridines in all occurrences of the sequence motif 5'-uridine-adenosine-3' (5'-UA-3'), 2'-modified uridines in all occurrences of the sequence motif 5'-uridine-guanosine-3' (5'-UG-3'), 2'-modified cytidines in all occurrences of the sequence motif 5'-cytidine-adenosine-3' (5'-CA-3'), 2'-modified cytidines in all occurrences of the sequence motif 5'-cytidine-Guanosine-3' (5'-CA-3'), 2'-modified 5'-most uridines in all occurrences of the sequence motif 5'-uridine-uridine-3' (5'-UU-3'), 2'-modified 5'-most cytidines in all occurrences of the sequence motif 5'-cytidine-cytidine-3' (5'-CC-3'), 2'-modified cytidines in all occurrences of the sequence motif 5'-cytidine-uridine-3' (5'-CU-3'), 2'-modified uridines in all occurrences of the sequence motif 5'-uridine-cytidine-3' (5'-UC-3'), and combinations thereof; and wherein the oligonucleotide further comprises at least one non-phosphodiester backbone linkage, nucleobase modification and/or sugar modification, e.g. a 2' sugar modification. Preferably, the non-phosphodiester backbone linkage, nucleobase modification and/or sugar modification is within the dinucleotide motif In certain embodiments, the oligonucleotide comprises a 5'-purine-purine-3' (5'-PuPu-3') dinucleotide motif at the 5' and/or 3' terminal end, wherein both nucleotide sugars are modified, e.g., 2'-modified. In one embodiment, at least one of the purines is modified at the 2, 6, 7, 8, $N^2$ exocyclic, and/or $N^6$ exocyclic positions, or combinations thereof. In another embodiment, the backbone linkage between the purines is a non-phosphodiester linkage.

In certain embodiments, the 5' terminal nucleotide of the oligonucleotide comprises sugar modification, e.g., a 2' modification, a 4' modification or an O4' modification, e.g., replacement of O4' with S, substituted N or $CH_2$. In one embodiment, the 5' terminal nucleotide further comprises a modified nucleobase or nucleobase modification.

Overhangs

Double-stranded oligonucleotides having at least one single-stranded nucleotide overhang have unexpectedly superior inhibitory properties than their blunt-ended counterparts. As used herein, the term "overhang" refers to a double-stranded structure where at least one end of one strand is longer than the corresponding end of the other strand forming the double-stranded structure. Generally, the single-stranded overhang is located at the 3'-terminal end of the antisense strand or, alternatively, at the 3'-terminal end of the sense strand. The double-stranded oligonucleotide can also have a blunt end, generally located at the 5'-end of the antisense strand. Generally, the antisense strand of the double-stranded oligonucleotide has a single-stranded overhang at the 3'-end, and the 5'-end is blunt.

In one embodiment, at least one end of the double-stranded region has a single-stranded nucleotide overhang of 1 to 4, generally 1 or 2 nucleotides. In certain other embodiment, both ends of the double-stranded region have a single-stranded nucleotide overhang of 1 to 4, generally 1 or 2 nucleotides.

In some embodiments it is particularly preferred, e.g., to enhance stability, to include particular nucleobases in the single-stranded overhangs, or to include modified nucleotides or nucleotide surrogates, in single-strand overhangs. For example, it can be desirable to include purine nucleotides in overhangs. In some embodiments all or some of the bases in the single strand overhang will be modified, e.g., with a modification described herein. Modifications in the single-stranded overhangs can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence. In certain embodiments, the single strand overhangs are asymmetrically modified with a modification described herein, e.g. a first single stand overhang comprises a modification that is not present in a second single strand overhang.

In certain embodiments, the unpaired nucleotide adjacent to the terminal nucleotide base pair on the end of the double-stranded region is a purine. In one embodiment, the single-stranded overhang has the sequence 5'-GCNN-3', wherein N is independently for each occurrence, A, G, C, U, dT, dU or absent. In certain embodiment, the single-stranded overhang has the sequence 5'-NN-3', wherein N is a modified or unmodified nucleotide described herein. In one preferred embodiment, the single-stranded overhang has the sequence 5'-dTdT-3' (dT=deoxythymidine). In another preferred embodiment, the single-stranded overhang has the sequence 5'-dTdT-3' (dT=deoxy thymidine) and the internucleotide linkage between the dTs is a non-phosphodiester backbone linkage.

In one embodiment, the antisense strand of the double-stranded oligonucleotide has 1-10 single-stranded nucleotide overhangs each at the 3' end and the 5' end over the sense strand. In another embodiment, the sense strand of the double-stranded oligonucleotide has 1-10 single-stranded nucleotide overhangs each at the 3' end and the 5' end over the antisense strand.

Mismatches

The antisense strand of the double-stranded oligonucleotide can contain one or more mismatches to the target sequence. In a preferred embodiment, the antisense strand contains no more than 3 mismatches. If the antisense strand contains mismatches to a target sequence, it is preferable that the area of mismatch not be located in the center of the region of complementarity between the antisense strand and the target sequence. If the antisense strand contains mismatches to the target sequence, it is preferable that the mismatch be restricted to 5 nucleotides from either end, for example 5, 4, 3, 2, or 1 nucleotide from either the 5' or 3' end of the region of complementarity between the antisense strand and the target sequence. The methods known in the art can be used to determine whether a double-stranded oligonucleotide containing a mismatch to a target sequence is effective in inhibiting the expression of the target gene.

In certain embodiments, the sense-strand comprises a mismatch to the antisense strand. In one embodiment, the sense strand comprises no more than 1, 2, 3, 4 or 5 mismatches to the antisense strand. In preferred embodiments, the sense strand comprises no more than 3 mismatches to the antisense strand.

In some embodiments, the sense-strand comprises a mismatch to the antisense strand and the mismatch is within the 5 nucleotides from the 3'-end of the sense strand, for example 5, 4, 3, 2, or 1 nucleotides from the end of the region of complementarity between the sense and the antisense strands.

In certain embodiments, the sense-strand comprises a mismatch to the antisense strand and the mismatch is located in the target cleavage site region. In certain embodiments, the sense strand comprises a nucleobase modification, e.g. an optionally substituted natural or non-natural nucleobase, a universal nucleobase, in the target cleavage site region.

The "target cleavage site" herein means the backbone linkage in the target gene, e.g. target mRNA, or the sense strand that is cleaved by the RISC mechanism by utilizing the RNAi agent. And the "target cleavage site region" comprises at least one or at least two nucleotides on 3', 5' or both sides of the cleavage site. Preferably, the target cleavage site region comprises two nucleotides on both sides of the cleavage site. For the sense strand, the target cleavage site is the backbone linkage in the sense strand that would get cleaved if the sense strand itself was the target to be cleaved by the RNAi mechanism. The target cleavage site can be determined using methods known in the art, for example the 5'-RACE assay as detailed in Soutschek et al., Nature (2004) 432, 173-178. Without wishing to be bound by theory, the cleavage site region for a conical double stranded RNAi agent comprising two 21-nucleotides long strands (wherein the strands form a double stranded region of 19 consecutive nucleotide base pairs having 2-nucleotide single stranded overhangs at the 3'-ends), the cleavage site region corresponds to positions 9-12 from the 5'-end of the sense strand.

Consideration of the efficacy of RNAi agents with mismatches in inhibiting expression of the target gene is important, especially if the particular region of complementarity in the target gene is known to have polymorphic sequence variation within the population.

Multi-Targeting

Sequences that are different from each other at 1, 2, 3, 4 or 5 positions can be targeted by a single RNAi agent, e.g., double-stranded or single-stranded RNAi agent. As used in this context, the phrase "different from each other" refers to the target sequences having different nucleotides at that position. In these cases the RNAi agent strand that is complementary to the target sequences comprises universal nucleobases at positions complementary to where the target sequences are different from each other. For example, the antisense strand of the double-stranded RNAi agent comprises universal nucleobases at positions complementary to where the sequences to be targeted do not match each other.

These multi targeting RNAi agents can be used to alter the expression of different transcripts/alleles of a single gene, different isoforms of a single gene, different splice variants of a single gene, different transcripts of more than one gene, wild-type and mutated form of a gene or homolog of a gene in different species.

The double-stranded RNAi agents described herein can also target more than one RNA region by having each strand targeting a sequence or part thereof independently. For example, a double-stranded RNAi agent can include a first and second sequence that are sufficiently complementary to each other to hybridize. The first sequence can be complementary to a first target sequence and the second sequence can be complementary to a second target sequence. The first and second sequences of the RNAi agent can be on different RNA strands, and the mismatch between the first and second sequences can be less than 50%, 40%, 30%, 20%, 10%, 5%, or 1%. The first and second sequences of the RNAi agent can be on the same RNA strand, and in a related embodiment more than 50%, 60%, 70%, 80%, 90%, 95%, or 1% of the RNAi agent can be in bimolecular form. The first and second sequences of the RNAi agent can be fully complementary to each other.

The first target sequence can be a first target gene and the second target sequence can be a second target gene, or the first and second target sequences can be different regions of a single target gene. The first and second sequences can differ by at least 1 nucleotide.

The first and second target sequences can be transcripts encoded by first and second sequence variants, e.g., first and second alleles, of a gene. The sequence variants can be mutations, or polymorphisms, for example. The first target sequence can include a nucleotide substitution, insertion, or deletion relative to the second target sequence, or the second target sequence can be a mutant or variant of the first target sequence. The first and second target sequences can comprise viral or human genes. The first and second target sequences can also be on variant transcripts of an oncogene or include different mutations of a tumor suppressor gene transcript. In addition, the first and second target sequences can correspond to hot-spots for genetic variation.

Terminal End Thermal Stability

The double stranded oligonucleotides can be optimized for RNA interference by increasing the propensity of the duplex to disassociate or melt (decreasing the free energy of duplex association), in the region of the 5' end of the antisense strand This can be accomplished, e.g., by the inclusion of modifications or modified nucleosides which increase the propensity of the duplex to disassociate or melt in the region of the 5' end of the antisense strand. It can also be accomplished by inclusion of modifications or modified nucleosides or attachment of a ligand that increases the propensity of the duplex to disassociate of melt in the region of the 5'end of the antisense strand. While not wishing to be bound by theory, the effect can be due to promoting the effect of an enzyme such as helicase, for example, promoting the effect of the enzyme in the proximity of the 5' end of the antisense strand.

Modifications which increase the tendency of the 5' end of the antisense strand in the duplex to dissociate can be used alone or in combination with other modifications described herein, e.g., with modifications which decrease the tendency of the 3' end of the antisense in the duplex to dissociate. Likewise, modifications which decrease the tendency of the 3' end of the antisense in the duplex to dissociate can be used alone or in combination with other modifications described herein, e.g., with modifications which increase the tendency of the 5' end of the antisense in the duplex to dissociate.

Nucleic acid base pairs can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; I:C is preferred over G:C (I=inosine); mismatches, e.g., non-canonical or other than canonical pairings are preferred over canonical (A:T, A:U, G:C) pairings; pairings which include a universal base are preferred over canonical pairings.

It is preferred that pairings which decrease the propensity to form a duplex are used at 1 or more of the positions in the duplex at the 5' end of the antisense strand. The terminal pair (the most 5' pair in terms of the antisense strand), and the subsequent 4 base pairing positions (going in the 3' direction in terms of the antisense strand) in the duplex are preferred for placement of modifications to decrease the propensity to form a duplex. More preferred are placements in the terminal most pair and the subsequent 3, 2, or 1 base pairings. It is preferred that at least 1, and more preferably 2, 3, 4, or 5 of the base pairs from the 5'-end of antisense strand in the duplex be chosen independently from the group of: A:U, G:U, I:C, mismatched pairs, e.g., non-canonical or other than canonical pairings or pairings which include a universal base. In a preferred embodiment at least one, at least 2, or at least 3 base-pairs include a universal base.

Modifications or changes which promote dissociation are preferably made in the sense strand, though in some embodiments, such modifications/changes will be made in the antisense strand.

Nucleic acid base pairs can also be ranked on the basis of their propensity to promote stability and inhibit dissociation or melting (e.g., on the free energy of association or dissociation of a particular pairing, the simplest approach is to examine the pairs on an individual pair basis, though next neighbor or similar analysis can also be used). In terms of promoting duplex stability: G:C is preferred over A:U, Watson-Crick matches (A:T, A:U, G:C) are preferred over non-canonical or other than canonical pairings, analogs that increase stability are preferred over Watson-Crick matches (A:T, A:U, G:C), e.g. 2-amino-A:U is preferred over A:U, 2-thio U or 5 Me-thio-U:A, are preferred over U:A, G-clamp (an analog of C having 4 hydrogen bonds):G is preferred over C:G, guanadinium-G-clamp:G is preferred over C:G, pseudo uridine:A, is preferred over U:A, sugar modifications, e.g., 2' modifications, e.g., 2'F, ENA, or LNA, which enhance binding are preferred over non-modified moieties and can be present on one or both strands to enhance stability of the duplex.

It is preferred that pairings which increase the propensity to form a duplex are used at 1 or more of the positions in the duplex at the 3' end of the antisense strand. The terminal pair (the most 3' pair in terms of the antisense strand), and the subsequent 4 base pairing positions (going in the 5' direction in terms of the antisense strand) in the duplex are preferred for placement of modifications to increase the propensity to form a duplex. More preferred are placements in the terminal most pair and the subsequent 3, 2, or 1 base pairings. It is preferred that at least 1, and more preferably 2, 3, 4, or 5 of the pairs of the recited regions be chosen independently from the group of: G:C, a pair having an analog that increases stability over Watson-Crick matches (A:T, A:U, G:C), 2-amino-A:U, 2-thio U or 5 Me-thio-U:A, G-clamp (an analog of C having 4 hydrogen bonds):G, guanadinium-G-clamp:G, pseudo uridine:A, a base pair in which one or both subunits has a sugar modification, e.g., a 2' modification, e.g., 2'F, ENA, or LNA, which enhance binding. In some embodiments, at least one, at least, at least 2, or at least 3, of the base pairs promote duplex stability.

In a preferred embodiment, at least one, at least 2, or at least 3, of the base pairs are a pair in which one or both subunits has a sugar modification, e.g., a 2' modification, e.g., 2'-O-methyl, 2'-O-Me (2'-O-methyl), 2'-O-MOE (2'-O-methoxyethyl), 2'-F, 2'-O—CH$_2$-(4'-C) (LNA) and 2'-O—CH$_2$CH$_2$-(4'-C) (ENA), which enhance binding.

G-clamps and guanidinium G-clamps are discussed in the following references: Holmes and Gait, "The Synthesis of 2'-O-Methyl G-Clamp Containing Oligonucleotides and Their Inhibition of the HIV-1 Tat-TAR Interaction," Nucleosides, Nucleotides & Nucleic Acids, 22:1259-1262, 2003; Holmes et al., "Steric inhibition of human immunodeficiency virus type-1 Tat-dependent trans-activation in vitro and in cells by oligonucleotides containing 2'-O-methyl G-clamp ribonucleoside analogues," Nucleic Acids Research, 31:2759-2768, 2003; Wilds, et al., "Structural basis for recognition of guanosine by a synthetic tricyclic cytosine analogue: Guanidinium G-clamp," Helvetica Chimica Acta, 86:966-978, 2003; Rajeev, et al., "High-Affinity Peptide Nucleic Acid Oligomers Containing Tricyclic Cytosine Analogues," Organic Letters, 4:4395-4398, 2002; Ausin, et al., "Synthesis of Amino- and Guanidino-G-Clamp PNA Monomers," Organic Letters, 4:4073-4075, 2002; Maier et al., "Nuclease resistance of oligonucleotides containing the tricyclic cytosine analogues phenoxazine and 9-(2-aminoethoxy)-phenoxazine ("G-clamp") and origins of their nuclease resistance properties," Biochemistry, 41:1323-7, 2002; Flanagan, et al., "A cytosine analog that confers enhanced potency to antisense oligonucleotides," Proceedings Of The National Academy Of Sciences Of The United States Of America, 96:3513-8, 1999.

As is discussed above, an oligonucleotide can be modified to both decrease the stability of the antisense 5'end of the duplex and increase the stability of the antisense 3' end of the duplex. This can be effected by combining one or more of the stability decreasing modifications in the antisense 5' end of the duplex with one or more of the stability increasing modifications in the antisense 3' end of the duplex.

Nuclease Stability

In vivo applications of oligonucleotides is limited due to presence of nucleases in the serum and/or blood. Thus in certain instances it is preferable to modify the 3', 5' or both ends of an oligonucleotide to make the oligonucleotide resistant against exonucleases, e.g., 3' to 5' exonucleases.

In certain embodiments, a double-stranded oligonucleotide comprises, on at least one end of the duplex region, a G-C base pair at the terminal position of the duplex region (e.g., the last base pair of the duplex) or the four consecutive base from the duplex region end comprise at least two G-C base pairs. In one embodiment, both ends of duplex region comprise a terminal G-C base pair and/or the first four consecutive base pairs from the terminal end comprise at least two G-C base pairs.

Off-Target Effects

In the RNA interference pathway, both strands of the double-stranded RNAi agent have the potential to enter the RISC complex and reduce the gene expression of corresponding complementary sequences. Without wishing to be bound by theory, one way an unwanted off-target effect happens ins when the sense strand enters the RISC complex and reduces the gene expression of a complementary sequence which is not the desired target of the RNAi agent.

A number of strategies can be applied to reduce the off-target effects due to sense strand mediated RNA interference. The sense strand can be chemically modified so that it can no longer act in the RISC mediated cleavage of a target sequence. Without wishing to be bound by theory, such modifications minimize off-target RNAi effects due to sense strand.

In one embodiment, the sense strand does not have a free terminal 5'-OH group. In another embodiment, the sense strand does not have a 5'-phosphate group. In certain embodiments, the 5'-OH of sense strand is modified so that it can not be phosphorylated, e.g. with a cap moiety. In certain embodiments, the cap moiety comprises L-sugar nucleotide, an alpha nucleotide, a hydroxy protecting group, an alkyl, a cycloalkyl or a heterocycle. In certain embodiments, the linkage between the 5' end of sense strand and a conjugate is a non-phosphodiester backbone linkage. In a preferred embodiment, the linkage between the 5' end of sense strand and a conjugate does not have a phosphate group.

In certain embodiments, the sense strand comprises at least one modified nucleotide in the target cleavage site region. Preferably, the modification include modification at 2' position of ribose sugar or more preferably a nucleobase modification.

In certain embodiments, ends of double-stranded oligonucleotide can be modified so that the end corresponding to 5'end of sense strand has a higher thermal stability as compared to the end corresponding 3' end of sense strand, as described above in the Terminal end thermal stability section above. Without wishing to be bound by theory, this allows preferential incorporation of the antisense strand into the RISC complex and reduces off-target effects of sense strand.

Specificity of the oligonucleotides of the invention can also be increased by selecting target sequences that are different at at least 1, 2, 3, 4, 5, 6, 7, 8, 9, 10 or more position from other sequences. Other sequences can be related genes, similar genes in closely related species, and variations and combinations thereof.

Asymmetric Modifications

Modifications described herein can be used to asymmetrically modified a double-stranded oligonucleotide. An asymmetrically modified double-stranded oligonucleotide is one in which one strand has a modification which is not present on the other strand. As such, an asymmetrical modification is a modification found on one strand but not on the other strand. Any modification, e.g., any modification described herein, can be present as an asymmetrical modification. An asymmetrical modification can confer any of the desired properties associated with a modification, e.g., those properties discussed herein. For example, an asymmetrical modification can confer resistance to degradation, an alteration in half life; target the oligonucleotide to a particular target, e.g., to a particular tissue; modulate, e.g., increase or decrease, the affinity of a strand for its complement or target sequence; or hinder or promote modification of a terminal moiety, e.g., modification by a kinase or other enzymes involved in the RISC mechanism pathway. The designation of a modification as having one property does not mean that it has no other property, e.g., a modification referred to as one which promotes stabilization might also enhance targeting. Asymmetrical modifications can include those in which only one strand is modified as well as those in which both are modified.

When the two strands of double-stranded oligonucleotide are linked together, e.g. a hairpin or a dumbbell, the two strands of the double stranded region can also be asymmetrically modified. For example, first strand of the double-stranded region comprises at least one asymmetric modification that is not present in the second strand of the double stranded region or vice versa.

While not wishing to be bound by theory or any particular mechanistic model, it is believed that asymmetrical modification allows a double-stranded RNAi agent to be optimized in view of the different or "asymmetrical" functions of the sense and antisense strands. For example, both strands can be modified to increase nuclease resistance, however, since some changes can inhibit RISC activity, these changes can be chosen for the sense stand. In addition, since some modifications, e.g., a ligand, can add large bulky groups that, e.g., can interfere with the cleavage activity of the RISC complex, such modifications are preferably placed on the sense strand. Thus, ligands, especially bulky ones (e.g. cholesterol), are preferentially added to the sense strand. The ligand can be present at either (or both) the 5' or 3' end of the sense strand of a RNAi agent.

Each strand can include one or more asymmetrical modifications. By way of example: one strand can include a first asymmetrical modification which confers a first property on the oligonucleotide and the other strand can have a second asymmetrical modification which confers a second property on the oligonucleotide. For example, one strand, e.g., the sense strand can have a modification which targets the oligonucleotide to a tissue, and the other strand, e.g., the antisense strand, has a modification which promotes hybridization with the target gene sequence.

In some embodiments both strands can be modified to optimize the same property, e.g., to increase resistance to nucleolytic degradation, but different modifications are chosen for the sense and the antisense strands, because the modifications affect other properties as well.

Multiple asymmetric modifications can be introduced into either or both of the sense and antisense strand. A strand can have at least 1, 2, 3, 4, 5, 6, 7, 8, or more modifications and all or substantially all of the monomers, e.g., nucleotides of a strand can be asymmetrically modified.

In certain embodiments, the asymmetric modifications are chosen so that only one of the two strands of double-stranded RNAi agent is effective in inducing RNAi. Inhibiting the induction of RNAi by one strand can reduce the off target effects due to cleavage of a target sequence by that strand.

In preferred embodiments asymmetrical modifications which result in one or more of the following are used: modifications of the 5' end of the sense strand which inhibit kinase activation of the sense strand, including, e.g., attachments of ligands or the use modifications which protect against 5' exonucleolytic degradation; or modifications of either strand, but preferably the sense strand, which enhance binding between 5'-end of the sense and 3'-end of the antisense strand and thereby promote a "tight" structure at this end of the molecule.

The end region of the RNAi agent defined by the 3' end of the sense strand and the 5'end of the antisense strand is also important for function. This region can include the terminal 2, 3, or 4 paired nucleotides and any 3' overhang. Preferred embodiments include asymmetrical modifications of either strand, but preferably the sense strand, which decrease binding between 3'-end of the sense and 5'-end of the antisense strand and thereby promote an "open" structure at this end of the molecule. Such modifications include placing conjugates which target the molecule or modifications which promote nuclease resistance on the sense strand in this region. Modification of the antisense strand which inhibit kinase activation are avoided in preferred embodiments.

Particularly preferred asymmetric modification are modifications of 2'-OH of ribose sugar and modification of backbone phosphodiester linkage. Other preferred asymmetric modifications include conjugation of ligands. Each strand can be conjugated with ligands that are different between the two strands.

In certain embodiments, one strand has an asymmetrical 2'-modification, e.g., a 2'-O-alkyl modification, and the other strand has an asymmetrical modification of the backbone phosphodiester linkage. In certain embodiments, one strand has an asymmetrical 2'-modification, e.g., a 2'-O-alkyl modification, and the other strand also has an asymmetrical 2'-modification that is different from the first strand's asymmetrical 2'-modification, e.g., 2'-fluoro modification.

In certain embodiments, one strand is asymmetrically modified with 2'-O-alkyl, e.g. 2'-OMe modification and the second strand is asymmetrically modified with 2'-fluoro modification.

In certain embodiments, one strand is asymmetrically modified with 2'-O-alkyl, e.g. 2'-OMe modification and the second strand is asymmetrically modified with backbone phosphodiester linkage modification, e.g. a phosphorothioate modification.

In certain embodiments, one strand is asymmetrically modified with 2'-fluoro modification and the second strand is asymmetrically modified with backbone phosphodiester linkage modification, e.g. a phosphorothioate modification.

It is preferable to have RNAi agents wherein there are multiple 2'-O-alkyl, e.g., 2% OMe modifications on the sense strand and multiple 2'-fluoro and/or multiple modified backbone phosphodiester linkages on the antisense strand.

Modifications, e.g., those described herein, which modulate, e.g., increase or decrease, the affinity of a strand for its compliment or target, can be provided as asymmetrical modifications.

Chimeric Oligonucleotides

The present invention also includes oligonucleotides which are chimeric oligonucleotides. "Chimeric" oligonucleotides or "chimeras," in the context of this invention, are oligonucleotide which contain two or more chemically distinct regions, each made up of at least one monomer unit, i.e., a modified or unmodified nucleotide in the case of an oligonucleotide. Chimeric oligonucleotides can be described as having a particular motif. In certain embodiments, the motifs include, but are not limited to, an alternating motif, a gapped motif, a hemimer motif, a uniformly fully modified motif and a positionally modified motif. As used herein, the phrase "chemically distinct region" refers to an oligonucleotide region which is different from other regions by having a modification that is not present elsewhere in the oligonucleotide or by not having a modification that is present elsewhere in the oligonucleotide. An oligonucleotide can comprise two or more chemically distinct regions. As used herein, a region that comprises no modifications is also considered chemically distinct.

A chemically distinct region can be repeated within an oligonucleotide. Thus, a pattern of chemically distinct regions in an oligonucleotide can be realized such that a first chemically distinct region is followed by one or more second chemically distinct regions. This sequence of chemically distinct regions can be repeated one or more times. Preferably, the sequence is repeated more than one time. Both strands of a double-stranded oligonucleotides can comprise these sequences. Each chemically distinct region can actually comprise as little as a single nucleotide. In certain embodiments, each chemically distinct region independently comprises 1, 2, 3, 4, 5, 6, 7, 8, 9, 10, 11, 12, 13, 14, 15, 16, 17 or 18 nucleotides.

In certain embodiments, alternating nucleotides comprise the same modification, e.g. all the odd number nucleotides in a strand have the same modification and/or all the even number nucleotides in a strand have the similar modification to the first strand. In certain other embodiments, all the odd number nucleotides in an oligonucleotide have the same modification and all the even numbered nucleotides have a modification that is not present in the odd number nucleotides and vice versa.

When both strands of a double-stranded oligonucleotide comprise the alternating modification patterns, nucleotides of one strand can be complementary in position to nucleotides of the second strand which are similarly modified. In an alternative embodiment, there is a phase shift between the patterns of modifications of the first strand, respectively, relative to the pattern of similar modifications of the second strand. Preferably, the shift is such that the similarly modified nucleotides of the first strand and second strand are not in complementary position to each other.

In certain embodiments, the first strand has an alternating modification pattern wherein alternating nucleotides comprise a 2'-modification, e.g., 2'-O-Methyl modification. In certain embodiments, the first strand comprises an alternating 2'-O-Methyl modification and the second strand comprises an alternating 2'-fluoro modification. In other embodiments, both strands of a double-stranded oligonucleotide comprise alternating 2'-O-methyl modifications.

When both strands of a double-stranded oligonucleotide comprise alternating 2'-O-methyl modifications, such 2'-modified nucleotides can be in complementary position in the duplex region. Alternatively, such 2'-modified nucleotides can not be in complementary positions in the duplex region.

In certain embodiments, the oligonucleotide comprises two chemically distinct regions, wherein each region is 1-10 nucleotides in length.

In other embodiments, the oligonucleotide comprises three chemically distinct regions. The middle region is about 5-15 nucleotide in length and each flanking or wing region is 1-5 nucleotides in length. All three regions can have different modifications or the wing regions can be similarly modified to each other.

As used herein the term "alternating motif" refers to an oligonucleotide comprising at least two different chemically distinct regions that that alternate for essentially the entire sequence of the oligonucleotide. In an alternating motif length of each region is independent of the length of other regions.

As used herein, the term "uniformly fully modified motif" refers to an oligonucleotide wherein all nucleotides in the oligonucleotide have at least one modification that is the same.

As used herein, the term "hemimer motif" refers to an oligonucleotide having two chemically distinct regions, wherein one region is at the 5' end of the oligonucleotide and the other region is at the 3 end of the oligonucleotide. In one embodiment, length of each chemically distinct region is independently 1 nucleotide to 1 nucleotide less than the length of the oligonucleotide.

As used herein the term "gapped motif" refers to an oligonucleotide having three chemically distinct regions. In one embodiment, the gapped motif is a symmetric gapped motif, wherein the two outer chemically distinct regions (wing regions) are identically modified. In another embodiment, the gapped motif is an asymmetric gaped motif in that the three regions are chemically distinct from each other.

As used herein the term "positionally modified motif" refers to an oligonucleotide having three or more chemically distinct regions. Positionally modified oligonucleotides are distinguished from gapped motifs, hemimer motifs, blockmer motifs and alternating motifs because the pattern of regional substitution defined by any positional motif does not fit into the definition provided herein for one of these other motifs. The term positionally modified oligomeric compound includes many different specific substitution patterns.

It is to be understood that when an oligonucleotide comprises two or more different modifications, modification pattern for each modification is independent of the pattern for the other modification. In certain embodiments, the modification pattern of two or more modifications do not overlap, partially overlap or fully overlap with each other.

In certain embodiments, oligonucleotide comprises two or more chemically distinct regions and has a structure as described in International Application No. PCT/US09/038433, filed Mar. 26, 2009, contents of which are herein incorporated in their entirety.

Ligands

A wide variety of entities, e.g., ligands, can be coupled to the oligonucleotides described herein. Ligands can include naturally occurring molecules, or recombinant or synthetic molecules. Exemplary ligands include, but are not limited to, polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG, e.g., PEG-2K, PEG-5K, PEG-10K, PEG-12K, PEG-15K, PEG-20K, PEG-40K), MPEG, [MPEG]$_2$, polyvinyl alcohol (PVA), polyurethane, poly(2-ethylacryllic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, an aptamer, asialofetuin, hyaluronan, procollagen, insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g., steroids, bile acids, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, natural or recombinant low density lipoprotein (LDL), natural or recombinant high-density lipoprotein (HDL), and a cell-permeation agent, preferably a helical cell-permeation agent.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides. A peptidomimetic (also referred to herein as an oligopeptidomimetic) is a molecule capable of folding into a defined three-dimensional structure similar to a natural peptide. The peptide or peptidomimetic ligand can be about 5-50 amino acids long, e.g., about 5, 10, 15, 20, 25, 30, 35, 40, 45, or 50 amino acids long.

Exemplary amphipathic peptides include, but are not limited to, cecropins, lycotoxins, paradaxins, buforin, CPF, bombinin-like peptide (BLP), cathelicidins, ceratotoxins, *S. clava* peptides, hagfish intestinal antimicrobial peptides (HFIAPs), magainines, brevinins-2, dermaseptins, melittins, pleurocidin, H$_2$A peptides, *Xenopus* peptides, esculentinis-1, and caerins.

As used herein, the term "endosomolytic ligand" refers to molecules having endosomolytic properties. Endosomolytic ligands promote the lysis of and/or transport of the composition of the invention, or its components, from the cellular compartments such as the endosome, lysosome, endoplasmic reticulum (ER), golgi apparatus, microtubule, peroxisome, or other vesicular bodies within the cell, to the cytoplasm of the cell. Some exemplary endosomolytic ligands include, but are not limited to, imidazoles, poly or oligoimidazoles, linear or branched polyethyleneimines (PEIs), linear and branched polyamines, e.g. spermine, cationic linear and branched polyamines, polycarboxylates, polycations, masked oligo or poly cations or anions, acetals, polyacetals, ketals/polyketals, orthoesters, linear or branched polymers with masked or unmasked cationic or anionic charges, dendrimers with masked or unmasked cationic or anionic charges, polyanionic peptides, polyanionic peptidomimetics, pH-sensitive peptides, natural and synthetic fusogenic lipids, natural and synthetic cationic lipids.

Exemplary endosomolytic/fusogenic peptide include, but are not limited to, AALEALAEALEALAEALEALAE-AAAAGGC (GALA), AALAEALAEALAEALAEA-LAEALAAAAGGC (EALA), ALEALAEALEALAEA, GLFEAIEGFIENGWEGMIWDYG (INF-7), GLFGAIAG-FIENGWEGMIDGWYG (Inf HA-2), GLF EAI EGFI ENGW EGMI DGWYGC GLF EAI EGFI ENGW EGMI DGWYGC (diINF-7), GLF EAI EGFI ENGW EGMI DGGC GLF EAI EGFI ENGW EGMI DGGC (diINF-3), GLFGALAEALAEALAEHLAEALAEALEALAAGGSC (GLF), GLFEAIEGFIENGWEGLAEALAEALEA-LAAGGSC (GALA-INF3), GLF EAI EGFI ENGW EGnI DG K GLF EAI EGFI ENGW EGnI DG (INF-5, n is norleucine), GLFEALLELLESLWELLLEA (JTS-1), GLFKALLKLLKSLWKLLLKA (ppTG1), GLFRALL-RLLRSLWRLLLRA (ppTG20), WEAKLAKALAKA-LAKHLAKALAKALKACEA (KALA), GLFFEAI-AEFIEGGWEGLIEGC (HA), GIGAVLKVLTTGLPALISWIKRKRQQ (Melittin), and histidine rich peptides H$_5$WYG and CHK$_6$HC.

Without wishing to be bound by theory, fusogenic lipids fuse with and consequently destabilize a membrane. Fusogenic lipids usually have small head groups and unsaturated acyl chains. Exemplary fusogenic lipids include, but are not limited to, 1,2-dileoyl-sn-3-phosphoethanolamine (DOPE), phosphatidylethanolamine (POPE), palmitoyloleoylphosphatidylcholine (POPC), (6Z,9Z,28Z,31Z)-heptatriaconta-6, 9,28,31-tetraen-19-ol (Di-Lin), N-methyl(2,2-di((9Z,12Z)-octadeca-9,12-dienyl)-1,3-dioxolan-4-yl)methanamine (DLin-k-DMA) and N-methyl-2-(2,2-di((9Z,12Z)-octadeca-9,12-dienyl)-1,3-dioxolan-4-yl)ethanamine (XTC).

Synthetic polymers with endosomolytic activity amenable to the present invention are described in United States Patent Application Publications Nos. 2009/0048410; 2009/0023890; 2008/0287630; 2008/0287628; 2008/0281044; 2008/0281041; 2008/0269450; 2007/0105804; 20070036865; and 2004/0198687, contents of which are hereby incorporated by reference in their entirety.

Exemplary cell permeation peptides include, but are not limited to, RQIKIWFQNRRMKWKK (penetratin), GRKKRRQRRRPPQC (Tat fragment 48-60), GALFLGWLGAAGSTMGAWSQPKKKRKV (signal sequence based peptide), LLIILRRRIRKQAHAHSK (PVEC), GWTLNSAGYLLKINLKALAALAKKIL (transportan), KLALKLALKALKAALKLA (amphiphilic model peptide), RRRRRRRRR (Arg9), KFFKFFKFFK (Bacterial cell wall permeating peptide), LLGDFFRKSKEKIGKEFKRIVQRIKDFLRNLVPRTES (LL-37), SWLSKTAKKLENSAKKRISEGIAIAIQGGPR (cecropin P1), ACYCRIPACIAGERRYGTCIYQGRLWAFCC (α-defensin), DHYNCVSSGGQCLYSACPIFTKIQGTCYRGKAKCCK (β-defensin), RRRPRPPYLPRPRPPPFFPPRLPPRIPPGFPPRFPPRFPGKR-NH2 (PR-39), ILPWKWPWWPWRR-NH2 (indolicidin), AAVALLPAVLLALLAP (RFGF), AALLPVLLAAP (RFGF analogue) and RKCRIVVIRVCR (bactenecin).

Exemplary cationic groups include, but are not limited to, protonated amino groups, derived from e.g., O-AMINE (AMINE=NH$_2$; alkylamino, dialkylamino, heterocyclyl, arylamino, diaryl amino, heteroaryl amino, or diheteroaryl amino, ethylene diamine, polyamino); aminoalkoxy, e.g., O(CH$_2$)$_n$AMINE, (e.g., AMINE=NH$_2$; alkylamino, dialkylamino, heterocyclyl, arylamino, diaryl amino, heteroaryl amino, or diheteroaryl amino, ethylene diamine, polyamino); amino (e.g. NH$_2$; alkylamino, dialkylamino, heterocyclyl, arylamino, diaryl amino, heteroaryl amino, diheteroaryl amino, or amino acid); and NH(CH$_2$CH$_2$NH)$_n$CH$_2$CH$_2$-AMINE (AMINE=NH$_2$; alkylamino, dialkylamino, heterocyclyl, arylamino, diaryl amino, heteroaryl amino, or diheteroaryl amino).

As used herein the term "targeting ligand" refers to any molecule that provides an enhanced affinity for a selected target, e.g., a cell, cell type, tissue, organ, region of the body, or a compartment, e.g., a cellular, tissue or organ compartment. Some exemplary targeting ligands include, but are not limited to, antibodies, antigens, folates, receptor ligands, carbohydrates, aptamers, integrin receptor ligands, chemokine receptor ligands, transferrin, biotin, serotonin receptor ligands, PSMA, endothelin, GCPII, somatostatin, LDL and HDL ligands.

Carbohydrate based targeting ligands include, but are not limited to, D-galactose, multivalent galactose, N-acetyl-D-galactose (GalNAc), multivalent GalNAc, e.g. GalNAC2 and GalNAc3; D-mannose, multivalent mannose, multivalent lactose, N-acetyl-galactosamine, N-acetyl-glucosamine, multivalent fucose, glycosylated polyaminoacids and lectins. The term multivalent indicates that more than one monosaccharide unit is present. Such monosaccharide subunits can be linked to each other through glycosidic linkages or linked to a scaffold molecule.

A number of folate and folate analogs amenable to the present invention as ligands are described in U.S. Pat. Nos. 2,816,110; 5,410,104; 5,552,545; 6,335,434 and 7,128,893, contents which are herein incorporated in their entireties by reference.

As used herein, the terms "PK modulating ligand" and "PK modulator" refers to molecules which can modulate the pharmacokinetics of the composition of the invention. Some exemplary PK modulator include, but are not limited to, lipophilic molecules, bile acids, sterols, phospholipid analogues, peptides, protein binding agents, vitamins, fatty acids, phenoxazine, aspirin, naproxen, ibuprofen, PEGs, and biotin. Oligonucleotides that comprise a number of phosphorothioate linkages are also known to bind to serum protein, thus short oligonucleotides, e.g. oligonucleotides of about 5 bases, 10 bases, 15 bases or 20 bases, comprising plurality of phosphorothioate linkages in the backbone are also amenable to the present invention as ligands (e.g. as PK modulating ligands). In addition, aptamers that bind serum components (e.g. serum proteins) are also amenable to the present invention as PK modulating ligands.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

In some embodiments, ligand on one strand of double-stranded oligonucleotide has affinity for a ligand on the second strand. In certain other embodiments, a ligand is covalently linked to both strands of a double-stranded oligonucleotide. As used herein, when a ligand is linked to more than oligonucleotide strand, point of attachment for an oligonucleotide can be an atom of the ligand self or an atom on a carrier molecule to which the ligand itself is attached.

Ligands can be coupled to the oligonucleotides at various places, for example, 3'-end, 5'-end, and/or at an internal position. When two or more ligands are present, the ligand can be on opposite ends of an oligonucleotide. In preferred embodiments, the ligand is attached to the oligonucleotides via an intervening tether/linker. The ligand or tethered ligand can be present on a monomer when said monomer is incorporated into the growing strand: In some embodiments, the ligand can be incorporated via coupling to a "precursor" monomer after said "precursor" monomer has been incorporated into the growing strand. For example, a monomer having, e.g., an amino-terminated tether (i.e., having no associated ligand), e.g., monomer-linker-NH$_2$ can be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction can be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligonucleotides, ligands can be attached to one or both strands. In some embodiments, a double-stranded RNAi agent comprises a ligand conjugated to the sense strand. In other embodiments, a double-stranded RNAi agent comprises a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. When a ligand is conjugated to a nucleobase, the preferred position is one that does not interfere with hybridization, i.e., does not interfere with the hydrogen bonding interactions needed for base pairing.

Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithioate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

There are numerous methods for preparing conjugates of oligomeric compounds. Generally, an oligomeric compound is attached to a conjugate moiety by contacting a reactive group (e.g., OH, SH, amine, carboxyl, aldehyde, and the like) on the oligomeric compound with a reactive group on the conjugate moiety. In some embodiments, one reactive group is electrophilic and the other is nucleophilic.

For example, an electrophilic group can be a carbonyl-containing functionality and a nucleophilic group can be an amine or thiol. Methods for conjugation of nucleic acids and related oligomeric compounds with and without linking groups are well described in the literature such as, for example, in Manoharan in Antisense Research and Applications, Crooke and LeBleu, eds., CRC Press, Boca Raton, Fla., 1993, Chapter 17, which is incorporated herein by reference in its entirety.

Representative United States patents that teach the preparation of oligonucleotide conjugates include, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,149,782; 5,214,136; 5,245,022; 5,254, 469; 5,258,506; 5,262,536; 5,272,250; 5,292,873; 5,317,098; 5,371,241, 5,391,723; 5,416,203, 5,451,463; 5,510, 475; 5,512,667; 5,514,785; 5,565,552; 5,567,810; 5,574, 142; 5,585,481; 5,587,371; 5,595,726; 5,597,696; 5,599, 923; 5,599,928; 5,672,662; 5,688,941; 5,714,166; 6,153, 737; 6,172,208; 6,300,319; 6,335,434; 6,335,437; 6,395, 437; 6,444,806; 6,486,308; 6,525,031; 6,528,631; 6,559, 279; contents which are herein incorporated in their entireties by reference.

Ligand Carriers

In some embodiments, the ligands, e.g. endosomolytic ligands, targeting ligands or other ligands, are linked to a monomer which is then incorporated into the growing oligonucleotide strand during chemical synthesis. Such monomers are also referred to as carrier monomers herein. The carrier monomer is a cyclic group or acyclic group; preferably, the cyclic group is selected from the group consisting of pyrrolidinyl, pyrazolinyl, pyrazolidinyl, imidazolinyl, imidazolidinyl, piperidinyl, piperazinyl, [1,3]-dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone. In certain embodiments, the cyclic carrier monomer is based on pyrrolidinyl such as 4-hydroxyproline or a derivative thereof.

Linkers

In certain embodiments, the covalent linkages between the oligonucleotide and other components, e.g. a ligand or a ligand carrying monomer can be mediated by a linker. This linker can be cleavable or non-cleavable, depending on the application. In certain embodiments, a cleavable linker can be used to release the nucleic acid after transport to the desired target. The intended nature of the conjugation or coupling interaction, or the desired biological effect, will determine the choice of linker group.

As used herein, the term "linker" means an organic moiety that connects two parts of a compound. Linkers typically comprise a direct bond or an atom such as oxygen or sulfur, a unit such as $NR^1$, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In one embodiment, the linker is $-[(P-Q-R)_q-X-(P'-Q'-R')_{q'}]_{q''}-T-$, wherein:

P, R, T, P' and R' are each independently for each occurrence absent, CO, NH, O, S, OC(O), NHC(O), $CH_2$, $CH_2NH$, $CH_2O$; $NHCH(R^a)C(O)$, $-C(O)-CH(R^a)-NH-$, C(O)-(optionally substituted alkyl)-NH—, CH=N—O

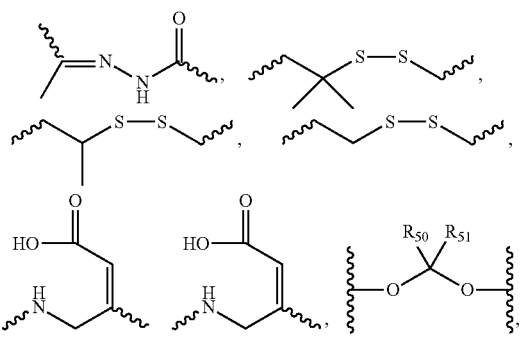

cyclyl, heterocycyclyl, aryl or heteroaryl; $R_{50}$ and $R_{51}$ are independently alkyl, substituted alkyl, or $R_{50}$ and $R_{51}$ taken together to form a cyclic ring;

Q and Q' are each independently for each occurrence absent, $-(CH_2)_n-$, $-C(R^{100})(R^{200})(CH_2)_n-$, $-(CH_2)_nC(R^{100})(R^{200})-$, $(CH_2CH_2O)_mCH_2CH_2-$, or $-(CH_2CH_2O)_mCH_2CH_2NH-$;

X is absent or a cleavable linking group;

$R^a$ is H or an amino acid side chain;

$R^{100}$ and $R^{200}$ are each independently for each occurrence H, $CH_3$, OH, SH or $N(R^X)_2$;

$R^X$ is independently for each occurrence H, methyl, ethyl, propyl, isopropyl, butyl or benzyl;

q, q' and q" are each independently for each occurrence 0-20 and wherein the repeating unit can be the same or different;

n is independently for each occurrence 1-20; and m is independently for each occurrence 0-50.

In one embodiment, the linker comprises at least one cleavable linking group.

In certain embodiments, the linker is a branched linker. The branchpoint of the branched linker may be at least trivalent, but can be a tetravalent, pentavalent or hexavalent atom, or a group presenting such multiple valencies. In certain embodiments, the branchpoint is, $-N$, $-N(Q)-C$, $-O-C$, $-S-C$, $-SS-C$, $-C(O)N(Q)-C$, $-OC(O)N(Q)-C$, $-N(Q)C(O)-C$, or $-N(Q)C(O)O-C$; wherein Q is independently for each occurrence H or optionally substituted alkyl. In one embodiment, the branchpoint is glycerol or derivative thereof.

In some embodiments, the carrier monomer can be based on the pyrroline ring system as shown in formula (I)

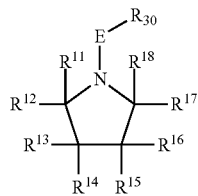

Formula (I)

wherein E is absent or C(O), C(O)O, C(O)NH, C(S), C(S)NH, SO, $SO_2$, or $SO_2NH$;

$R^{11}$, $R^{12}$, $R^{13}$, $R^{14}$, $R^{15}$, $R^{16}$, $R^{17}$, and $R^{18}$ are each independently for each occurrence H, $-CH_2OR^a$, or $OR^b$;

$R^a$ and $R^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, or a solid support;

$R^{30}$ is independently for each occurrence -linker-$R^L$;

$R^L$ is hydrogen or a ligand, e.g. an endosomolytic agent, a targeting ligand or other ligand described herein; and provided that $R^L$ is a ligand at least once.

For the pyrroline-based monomers, $R^{11}$ is $-CH_2OR^a$ and $R1^3$ is $OR^b$; or $R^{11}$ is $-CH_2OR^a$ and $R^9$ is $OR^b$; or $R^{11}$ is $-CH_2OR^a$ and $R^{17}$ is $OR^b$; or $R^{13}$ is $-CH_2OR^a$ and $R^{11}$ is $OR^b$; or $R^{13}$ is $-CH_2OR^a$ and $R^{15}$ is $OR^b$; or $R^{13}$ is $-CH_2OR^a$ and $R^{17}$ is $OR^b$. In certain embodiments, $CH_2OR^a$ and $OR^b$ can be geminally substituted. For the 4-hydroxyproline-based monomers, $R^{11}$ is $-CH_2OR^a$ and $R^{17}$ is $OR^b$. The pyrroline- and 4-hydroxyproline-based compounds can therefore contain linkages (e.g., carbon-carbon bonds) wherein bond rotation is restricted about that particular linkage, e.g. restriction resulting from the presence of a ring. Thus, $CH_2OR^a$ and $OR^b$ can be cis or trans with respect to one another in any of the pairings delineated above Accordingly, all cis/trans isomers are expressly included. The compounds can also contain one or more asymmetric centers and thus occur as racemates and racemic mixtures, single enantiomers, individual diastereomers and diastereomeric mixtures. All such isomeric forms of the compounds are expressly included (e.g., the centers bearing $CH_2OR^a$ and $OR^b$ can both have the R configuration; or both have the S configuration; or one center can have the R configuration and the other center can have the S configuration and vice versa).

In one preferred embodiment, $R^{11}$ is $CH_2OR^a$ and $R^{15}$ is $OR^b$.

In one embodiment, $R^b$ is a solid support.

In another embodiment, carrier of formula (I) is a phosphoramidite, i.e., one of $R^a$ or $R^b$ is $-P(O\text{-alkyl})N(\text{alkyl})_2$, e.g., $-P(OCH_2CH_2CN)N(i\text{-propyl})_2$. In one embodiment, $R^b$ is $-P(O\text{-alkyl})N(\text{alkyl})_2$.

In some embodiments, the carrier can be based on the ribose ring system as shown in formula (II).

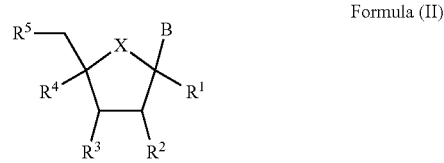

Formula (II)

wherein:

X is O, S, $NR^N$ or $CR^P_2$;

B is independently for each occurrence hydrogen, optionally substituted natural or non-natural nucleobase, optionally substituted natural nucleobase conjugated with -linker-$R^L$ or optionally substituted non-natural nucleobase conjugated with -linker-$R^L$;

$R^1$, $R^2$, $R^3$, $R^4$ and $R^5$ are each independently for each occurrence H, $OR^6$, F, $N(R^N)_2$, or -J-linker-$R^L$;

J is absent, O, S, $NR^N$, OC(O)NH, NHC(O)O, C(O)NH, NHC(O), NHSO, $NHSO_2$, $NHSO_2NH$, OC(O), C(O)O, OC(O)O, NHC(O)NH, NHC(S)NH, OC(S)NH, $OP(N(R^P)_2)O$, or $OP(N(R^P)_2)$;

$R^6$ is independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiblothionate, a phosphodiester, a phosphotriester, an activated phosphate group, an activated phosphite group, a phosphoramidite or a solid support;

$R^N$ is independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

$R^P$ is independently for each occurrence H, optionally substituted alkyl, optionally substituted alkenyl, optionally substituted alkynyl, optionally substituted aryl, optionally substituted cycloalkyl or optionally substituted heteroaryl;

$R^L$ is hydrogen or a ligand, e.g. an endosomolytic agent, a targeting ligand or other ligand described herein; and provided that $R^L$ is present at least once and further provided that $R^L$ is a ligand at least once.

In some embodiments, the carrier monomer is based on an acyclic group and is termed an "acyclic carrier". Preferred acyclic carriers can have the structure shown in formula (III) or formula (IV) below.

In some embodiments, the acyclic carrier has the structure shown in formula (III).

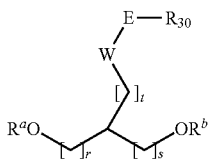

Formula (III)

wherein:

W is absent, O, S and N($R^N$), where $R^N$ is independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

E is absent or C(O), C(O)O, C(O)NH, C(S), C(S)NH, SO, SO$_2$, or SO$_2$NH;

$R^a$ and $R^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite or a solid support;

$R^{30}$ is independently for each occurrence -linker-$R^L$;

$R^L$ is hydrogen or a ligand, e.g. an endosomolytic agent, a targeting ligand or other ligand described herein; and r, s and t are each independently for each occurrence 0, 1, 2 or 3;

provided that $R^L$ is a ligand at least once.

When r and s are different, then the tertiary carbon can be either the R or S configuration. In preferred embodiments, x and y are one and z is zero (e.g. carrier is based on serinol). The acyclic carriers can optionally be substituted, e.g. with hydroxy, alkoxy, perhaloalky.

In some embodiments, the acyclic carrier has the structure shown in formula (IV)

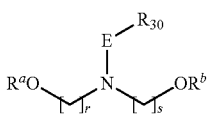

Formula (IV)

wherein E is absent or C(O), C(O)O, C(O)NH, C(S), C(S)NH, SO, SO$_2$, or SO$_2$NH;

$R^a$ and $R^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite or a solid support;

$R^{30}$ is independently for each occurrence -linker-$R^L$;

$R^L$ is hydrogen or a ligand; and r and s are each independently for each occurrence 0, 1, 2 or 3;

provided that $R^L$ is a ligand at least once.

Other ligands and ligand conjugated monomers amenable to the invention are described in U.S. patent application Ser. No. 10/916,185, filed Aug. 10, 2004; Ser. No. 10/946,873, filed Sep. 21, 2004; Ser. No. 10/985,426, filed Nov. 9, 2004; Ser. No. 10/833,934, filed Aug. 3, 2007; Ser. No. 11/115,989 filed Apr. 27, 2005, Ser. No. 11/119,533, filed Apr. 29, 2005; Ser. No. 11/197,753, filed Aug. 4, 2005; Ser. No. 11/944,227, filed Nov. 21, 2007; Ser. No. 12/328,528, filed Dec. 4, 2008; and Ser. No. 12/328,537, filed Dec. 4, 2008, contents which are herein incorporated in their entireties by reference for all purposes. Ligands and ligand conjugated monomers amenable to the invention are also described in International Application Nos. PCT/US04/001461, filed Jan. 21, 2004; PCT/US04/010586, filed Apr. 5, 2004; PCT/US04/011255, filed Apr. 9, 2005; PCT/US05/014472, filed Apr. 27, 2005; PCT/US05/015305, filed Apr. 29, 2005; PCT/US05/027722, filed Aug. 4, 2005; PCT/US08/061289, filed Apr. 23, 2008; PCT/US08/071576, filed Jul. 30, 2008; PCT/US08/085574, filed Dec. 4, 2008 and PCT/US09/40274, filed Apr. 10, 2009, contents which are herein incorporated in their entireties by reference for all purposes.

Cleavable Linking Groups

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis. Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). One preferred embodiment is —C(R)$_2$—S—S—, wherein R is H or C$_1$-C$_6$ alkyl and at least one R is C$_1$-C$_6$ alkyl such as CH$_3$ or CH$_2$CH$_3$.

Phosphate-Based Cleavable Linking Groups

Phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—, wherein R is optionally substituted linear or branched C$_1$-C$_{10}$ alkyl A preferred embodiment is —O—P(O)(OH)—O—.

Acid Cleavable Linking Groups

Acid cleavable linking groups are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN— or —OC(O)—.

Ester-Based Cleavable Linking Groups

Ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—.

Peptide-Based Cleavable Linking Groups

Peptide-based cleavable linking groups are cleaved by enzymes such as peptidases and proteases in cells. A peptide based cleavable linking group comprises two or more amino acids. Peptide-based cleavable linking groups have the general formula —NHCHR$^A$C(O)NHCHR$^B$C(O)—, where R$^A$ and R$^B$ are the R groups of the two adjacent amino acids. In certain embodiments, the peptide-based cleavage linkage comprises the amino acid sequence that is the substrate for a peptidase or a protease found in cells.

Oligonucleotide Production

The oligonucleotide compounds of the invention can be prepared using solution-phase or solid-phase organic synthesis, or enzymatically by methods known in the art. Organic synthesis offers the advantage that the oligonucleotide strands comprising non-natural or modified nucleotides can be easily prepared. Any other means for such synthesis known in the art can additionally or alternatively be employed. It is also known to use similar techniques to prepare other oligonucleotides, such as the phosphorothioates, phosphorodithioates and alkylated derivatives. The double-stranded oligonucleotide compounds of the invention can be prepared using a two-step procedure. First, the individual strands of the double-stranded molecule are prepared separately. Then, the component strands are annealed.

Regardless of the method of synthesis, the oligonucleotide can be prepared in a solution (e.g., an aqueous and/or organic solution) that is appropriate for formulation. For example, the oligonucleotide preparation can be precipitated and redissolved in pure double-distilled water, and lyophilized. The dried oligonucleotide can then be resuspended in a solution appropriate for the intended formulation process.

Teachings regarding the synthesis of particular modified oligonucleotides can be found in the following U.S. patents or pending patent applications: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having .beta.-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups can be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262,241, and 5,459,255, drawn to, inter alia, methods of synthesizing 2'-fluoro-oligonucleotides.

Gene Expression Modulation

As used herein the term "modulate gene expression" means that expression of the gene, or level of RNA molecule or equivalent RNA molecules encoding one or more proteins or protein subunits is up regulated of down regulated, such that expression, level, or activity is greater than or less than that observed in the absence of the modulator. For example, the term "modulate" can mean "inhibit," but the use of the word "modulate" is not limited to this definition.

As used herein, gene expression modulation happens when the expression of the gene, or level of RNA molecule or equivalent RNA molecules encoding one or more proteins or protein subunits is different by at least 5%, 10%, 20%, 30%, 40%, 50%, 60%, 70%, 80%, 90%, 100%, 2-fold, 3-fold, 4-fold, 5-fold or more from that observed in the absence of modulator, e.g., oligonucleotide. The % and(/or) fold difference can be calculated relative to the control or the non-control.

As used herein, the term "inhibit", "down-regulate", or "reduce", means that the expression of the gene, or level of RNA molecules or equivalent RNA molecules encoding one or more proteins or protein subunits, or activity of one or more proteins or protein subunits, is reduced below that observed in the absence of modulator. The gene expression is down-regulated when expression of the gene, or level of RNA molecules or equivalent RNA molecules encoding one or more proteins or protein subunits, or activity of one or more proteins or protein subunits, is reduced at least 10% lower relative to a corresponding non-modulated control, and preferably at least 20%, 30%, 40%, 50%, 60%, 70%, 80%, 90%, 95%, 98%, 99% or most preferably, 100% (i.e., no gene expression).

As used herein, the term "increase" or "up-regulate", means that the expression of the gene, or level of RNA molecules or equivalent RNA molecules encoding one or more proteins or protein subunits, or activity of one or more proteins or protein subunits, is increased above that observed in the absence of modulator. The gene expression is up-regulated when expression of the gene, or level of RNA molecules or equivalent RNA molecules encoding one or more proteins or protein subunits, or activity of one or more proteins or protein subunits, is increased at least 10% relative to a corresponding non-modulated control, and preferably at least 20%, 30%, 40%, 50%, 60%, 70%, 80%, 90%, 95%, 98%, 99% 100%, 2-fold, 5-fold, 10-fold, 100-fold or 1000-fold higher than in the absence of a modulator.

By "gene" or "target gene" is meant, a nucleic acid that encodes an RNA, for example, nucleic acid sequences including, but not limited to, structural genes encoding a polypeptide. The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus.

Formulations/Delivery Agents

For ease of exposition the formulations, compositions, delivery agents and methods in this section are discussed largely with regard to RNAi agents. It may be understood, however, that these formulations, compositions and methods can be practiced with other oligonucleotides described herein, e.g., antisense, antagomir, aptamer, microRNA, antimir and ribozyme, and such practice is within the invention.

A formulated RNAi composition can assume a variety of states. In some examples, the composition is at least partially crystalline, uniformly crystalline, and/or anhydrous (e.g., less than 80, 50, 30, 20, or 10% water). In another example, the RNAi is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a micro particle as can be appropriate for a crystalline composition). Generally, the RNAi composition is formulated in a manner that is compatible with the intended method of administration.

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

An RNAi preparation can be formulated in combination with another agent, e.g., another therapeutic agent or an agent that stabilizes the RNAi agent, e.g., a protein that complex with RNAi agent to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the RNAi preparation includes another RNAi agent, e.g., a second RNAi that can mediated RNAi with respect to a second gene, or with respect to the same gene. Still other preparation can include at least 3, 5, ten, twenty, fifty, or a hundred or more different RNAi species. Such RNAi agents can mediate RNAi with respect to a similar number of different genes.

In one embodiment, the RNAi preparation includes at least a second therapeutic agent (e.g., an agent other than RNA or DNA). For example, an RNAi composition for the treatment of a viral disease, e.g., HIV, might include a known antiviral agent (e.g., a protease inhibitor or reverse transcriptase inhibitor). In another example, an RNAi agent composition for the treatment of a cancer might further comprise a chemotherapeutic agent.

Exemplary formulations and/or delivery agents are discussed below:

Liposomes

The oligonucleotides of the invention, e.g. antisense, antagomir, aptamer, ribozyme and RNAi agent can be formulated in liposomes. As used herein, a liposome is a structure having lipid-containing membranes enclosing an aqueous interior. Liposomes can have one or more lipid membranes. Liposomes can be characterized by membrane type and by size. Small unilamellar vesicles (SUVs) have a single membrane and typically range between 0.02 and 0.05 µm in diameter; large unilamellar vesicles (LUVS) are typically larger than 0.05 µm. Oligolamellar large vesicles and multilamellar vesicles have multiple, usually concentric, membrane layers and are typically larger than 0.1 µm. Liposomes with several non-concentric membranes, i.e., several smaller vesicles contained within a larger vesicle, are termed multivesicular vesicles.

Liposomes can further include one or more additional lipids and/or other components such as cholesterol. Other lipids can be included in the liposome compositions for a variety of purposes, such as to prevent lipid oxidation, to stabilize the bilayer, to reduce aggregation during formation or to attach ligands onto the liposome surface. Any of a number of lipids can be present, including amphipathic, neutral, cationic, and anionic lipids. Such lipids can be used alone or in combination.

Additional components that can be present in a liposomes include bilayer stabilizing components such as polyamide oligomers (see, e.g., U.S. Pat. No. 6,320,017), peptides, proteins, detergents, lipid-derivatives, such as PEG conjugated to phosphatidylethanolamine, PEG conjugated to phosphatidic acid, PEG conjugated to ceramides (see, U.S. Pat. No. 5,885,613), PEG conjugated dialkylamines and PEG conjugated 1,2-diacyloxypropan-3-amines.

Liposome can include components selected to reduce aggregation of lipid particles during formation, which can result from steric stabilization of particles which prevents charge-induced aggregation during formation. Suitable components that reduce aggregation include, but are not limited to, polyethylene glycol (PEG)-modified lipids, monosialoganglioside Gm1, and polyamide oligomers ("PAO") such as (described in U.S. Pat. No. 6,320,017). Exemplary suitable PEG-modified lipids include, but are not limited to, PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Particularly preferred are PEG-modified diacylglycerols and dialkylglycerols. Other compounds with uncharged, hydrophilic, steric-barrier moieties, which prevent aggregation during formation, like PEG, Gm1, or ATTA, can also be coupled to lipids to reduce aggregation during formation. ATTA-lipids are described, e.g., in U.S. Pat. No. 6,320,017, and PEG-lipid conjugates are described, e.g., in U.S. Pat. Nos. 5,820,873, 5,534,499 and 5,885,613. Typically, the concentration of the lipid component selected to reduce aggregation is about 1 to 15% (by mole percent of lipids). It should be noted that aggregation preventing compounds do not necessarily require lipid conjugation to function properly. Free PEG or free ATTA in solution can be sufficient to prevent aggregation. If the liposomes are stable after formulation, the PEG or ATTA can be dialyzed away before administration to a subject.

Neutral lipids, when present in the liposome composition, can be any of a number of lipid species which exist either in an uncharged or neutral zwitterionic form at physiological pH. Such lipids include, for example diacylphosphatidylcholine, diacylphosphatidylethanolamine, ceramide, sphingomyelin, dihydrosphingomyelin, cephalin, and cerebrosides. The selection of neutral lipids for use in liposomes described herein is generally guided by consideration of, e.g., liposome size and stability of the liposomes in the bloodstream. Preferably, the neutral lipid component is a lipid having two acyl groups, (i.e., diacylphosphatidylcholine and diacylphosphatidylethanolamine). Lipids having a variety of acyl chain groups of varying chain length and degree of saturation are available or can be isolated or synthesized by well-known techniques. In one group of embodiments, lipids containing saturated fatty acids with carbon chain lengths in the range of $C_{14}$ to $C_{22}$ are preferred. In another group of embodiments, lipids with mono or diunsaturated fatty acids with carbon chain lengths in the range of $C_{14}$ to $C_{22}$ are used. Additionally, lipids having mixtures of saturated and unsaturated fatty acid chains can be used. Preferably, the neutral lipids used in the present invention are DOPE, DSPC, POPC, DMPC, DPPC or any related phosphatidylcholine. The neutral lipids useful in the present invention can also be composed of sphingomyelin, dihydrosphingomyeline, or phospholipids with other head groups, such as serine and inositol.

The sterol component of the lipid mixture, when present, can be any of those sterols conventionally used in the field of liposome, lipid vesicle or lipid particle preparation. A preferred sterol is cholesterol.

Cationic lipids, when present in the liposome composition, can be any of a number of lipid species which carry a net positive charge at about physiological pH. Such lipids include, but are not limited to, N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.Cl"); 3β-(N—(N', N-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoracetate ("DOSPA"), dioctadecylamidoglycyl carboxyspermine ("DOGS"), 1,2-dioleoyl-sn-3-phosphoethanolamine ("DOPE"), 1,2-dioleoyl-3-dimethylammonium propane ("DODAP"), N, N-dimethyl-2,3-dioleyloxy)propylamine ("DODMA"), N-(1,2-dimyristyloxyprop-3-yl)-N, N-dimethyl-N-hydroxyethyl ammonium bromide ("DMRIE"), 5-carboxyspermylglycine diocaoleyamide ("DOGS"), and dipalmitoylphosphatidylethanolamine 5-carboxyspermyl-amide ("DPPES"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL). Other cationic lipids suitable for lipid particle formation are described in WO98/39359, WO96/

37194. Other cationic lipids suitable for liposome formation are described in U.S. Provisional applications No. 61/018,616 (filed Jan. 2, 2008), No. 61/039,748 (filed Mar. 26, 2008), No. 61/047,087 (filed Apr. 22, 2008) and No. 61/051,528 (filed May 21-2008), all of which are incorporated by reference in their entireties for all purposes.

Anionic lipids, when present in the liposome composition, can be any of a number of lipid species which carry a net negative charge at about physiological pH. Such lipids include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

"Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and β-acyloxyacids, can also be used. Additionally, such amphipathic lipids can be readily mixed with other lipids, such as triglycerides and sterols.

Also suitable for inclusion in the liposome compositions of the present invention are programmable fusion lipids. Liposomes containing programmable fusion lipids have little tendency to fuse with cell membranes and deliver their payload until a given signal event occurs. This allows the liposome to distribute more evenly after injection into an organism or disease site before it starts fusing with cells. The signal event can be, for example, a change in pH, temperature, ionic environment, or time. In the latter case, a fusion delaying or "cloaking" component, such as an ATTA-lipid conjugate or a PEG-lipid conjugate, can simply exchange out of the liposome membrane over time. By the time the liposome is suitably distributed in the body, it has lost sufficient cloaking agent so as to be fusogenic. With other signal events, it is desirable to choose a signal that is associated with the disease site or target cell, such as increased temperature at a site of inflammation.

A liposome can also include a targeting moiety, e.g., a targeting moiety that is specific to a cell type or tissue. Targeting of liposomes with a surface coating of hydrophilic polymer chains, such as polyethylene glycol (PEG) chains, for targeting has been proposed (Allen, et al., *Biochimica et Biophysica Acta* 1237: 99-108 (1995); DeFrees, et al., *Journal of the American Chemistry Society* 118: 6101-6104 (1996); Blume, et al., *Biochimica et Biophysica Acta* 1149: 180-184 (1993); Klibanov, et al., *Journal of Liposome Research* 2: 321-334 (1992); U.S. Pat. No. 5,013,556; Zalipsky, *Bioconjugate Chemistry* 4: 296-299 (1993); Zalipsky, *FEBS Letters* 353: 71-74 (1994); Zalipsky, in Stealth Liposomes Chapter 9 (Lasic and Martin, Eds) CRC Press, Boca Raton Fla. (1995). Other targeting moieties, such as ligands, cell surface receptors, glycoproteins, vitamins (e.g., riboflavin), aptamers and monoclonal antibodies, can also be used. The targeting moieties can include the entire protein or fragments thereof. Targeting mechanisms generally require that the targeting agents be positioned on the surface of the liposome in such a manner that the targeting moiety is available for interaction with the target, for example, a cell surface receptor.

In one approach, a targeting moiety, such as receptor binding ligand, for targeting the liposome is linked to the lipids forming the liposome. In another approach, the targeting moiety is attached to the distal ends of the PEG chains forming the hydrophilic polymer coating (Klibanov, et al., *Journal of Liposome Research* 2: 321-334 (1992); Kirpotin et al., *FEBS Letters* 388: 115-118 (1996)). A variety of different targeting agents and methods are known and available in the art, including those described, e.g., in Sapra, P. and Allen, T M, *Prog. Lipid Res.* 42(5):439-62 (2003); and Abra, R M et al., *J Liposome Res.* 12:1-3, (2002). Other lipids conjugated with targeting moieties are described in U.S. provisional application No. 61/127,751 (filed May 14, 2008) and PCT application #PCT/US2007/080331 (filed Oct. 3, 2007), all of which are incorporated by reference in their entireties for all purposes.

A liposome composition of the invention can be prepared by a variety of methods that are known in the art. See e.g., U.S. Pat. No. 4,235,871, U.S. Pat. No. 4,897,355 and U.S. Pat. No. 5,171,678; published PCT applications WO 96/14057 and WO 96/37194; Feigner, P. L. et al., *Proc. Natl. Acad. Sci.*, USA (1987) 8:7413-7417, Bangham, et al. *M. Mol. Biol.* (1965) 23:238, Olson, et al. *Biochim. Biophys. Acta* (1979) 557:9, Szoka, et al. *Proc. Natl. Acad. Sci.* (1978) 75: 4194, Mayhew, et al. *Biochim. Biophys. Acta* (1984) 775:169, Kim, et al. *Biochim. Biophys. Acta* (1983) 728:339, and Fukunaga, et al. *Endocrinol.* (1984) 115:757.

For example, a liposome composition of the invention can be prepared by first dissolving the lipid components of a liposome in a detergent so that micelles are formed with the lipid component. The detergent can have a high critical micelle concentration and can be nonionic. Exemplary detergents include, but are not limited to, cholate, CHAPS, octylglucoside, deoxycholate and lauroyl sarcosine. The RNAi agent preparation e.g., an emulsion, is then added to the micelles that include the lipid components. After condensation, the detergent is removed, e.g., by dialysis, to yield a liposome containing the RNAi agent. If necessary a carrier compound that assists in condensation can be added during the condensation reaction, e.g., by controlled addition. For example, the carrier compound can be a polymer other than a nucleic acid (e.g., spermine or spermidine). To favor condensation, pH of the mixture can also be adjusted.

In another example, liposomes of the present invention can be prepared by diffusing a lipid derivatized with a hydrophilic polymer into preformed liposome, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the RNAi agent is first dispersed by sonication in a lysophosphatidylcholine or other low CMC surfactant (including polymer grafted lipids). The resulting micellar suspension of RNAi agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323.

Other suitable formulations for RNAi agents are described in PCT application No. PCT/US2007/080331 (filed Oct. 3, 2007) and U.S. Provisional application No. 61/018,616 (filed Jan. 2, 2008), No. 61/039,748 (filed Mar. 26, 2008), No. 61/047,087 (filed Apr. 22, 2008) and No. 61/051,528 (filed May 21-2008), No. 61/113,179 (filed Nov. 10, 2008) all of which are incorporated by reference in their entireties for all purposes.

Micelles and Other Membranous Formulations

Recently, the pharmaceutical industry introduced microemulsification technology to improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

As defined herein, "micelles" are a particular type of molecular assembly in which amphipathic molecules are arranged in a spherical structure such that all hydrophobic portions on the molecules are directed inward, leaving the hydrophilic portions in contact with the surrounding aqueous phase. The converse arrangement exists if the environment is hydrophobic.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Exemplary amphiphilic carriers include, but are not limited to, lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof.

Particularly preferred amphiphilic carriers are saturated and monounsaturated polyethyleneglycolyzed fatty acid glycerides, such as those obtained from fully or partially hydrogenated various vegetable oils. Such oils can advantageously consist of tri-. di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-monolaurate and di-laurate, Lecithin, Polysorbate 80, etc (produced and distributed by a number of companies in USA and worldwide).

Mixed micelle formulation suitable for delivery through transdermal membranes can be prepared by mixing an aqueous solution of the RNAi composition, an alkali metal $C_8$ to $C_{22}$ alkyl sulphate, and an amphiphilic carrier. The amphiphilic carrier can be added at the same time or after addition of the alkali metal alkyl sulphate. Mixed micelles will form with substantially any kind of mixing of the ingredients but vigorous mixing in order to provide smaller size micelles.

In one method a first micelle composition is prepared which contains the RNAi composition and at least the alkali metal alkyl sulphate. The first micelle composition is then mixed with at least three amphiphilic carriers to form a mixed micelle composition. In another method, the micelle composition is prepared by mixing the RNAi composition, the alkali metal alkyl sulphate and at least one of the amphiphilic carriers, followed by addition of the remaining micelle amphiphilic carriers, with vigorous mixing.

Phenol and/or m-cresol can be added to the mixed micelle composition to stabilize the formulation and protect against bacterial growth. Alternatively, phenol and/or m-cresol can be added with the amphiphilic carriers. An isotonic agent such as glycerin can also be added after formation of the mixed micelle composition.

For delivery of the micelle formulation as a spray, the formulation can be put into an aerosol dispenser and the dispenser is charged with a propellant, such as hydrogen-containing chlorofluorocarbons, hydrogen-containing fluorocarbons, dimethyl ether, diethyl ether and HFA 134a (1,1,1,2 tetrafluoroethane).

Emulsions

The oligonucleotides of the present invention can be prepared and formulated as emulsions. Emulsions are typically heterogeneous systems of one liquid dispersed in another in the form of droplets (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials is also included in emulsion formulations and contributes to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions are formulated as microemulsions. A microemulsion can be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions can form spontaneously when their components are brought together at ambient temperature. This can be particularly advantageous when formulating thermolabile drugs, peptides or dsRNAs. Microemulsions have also been effective in the transdermal delivery of active components in both cosmetic and pharmaceutical applications. It is expected that the microemulsion compositions and formulations of the present invention will facilitate the increased absorption of oligonucleotides as well as improve the local cellular uptake of oligonucleotides.

Microemulsions of the present invention can also contain additional components and additives such as sorbitan monostearate (Grill 3), Labrasol, and penetration enhancers to improve the properties of the formulation and to enhance the absorption of the oligonucleotides of the present invention. Penetration enhancers used in the microemulsions of the present invention can be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Lipid Particles

It has been shown that lipid-conjugated oligonucleotides, e.g., cholesterol-conjugated oligonucleotides, bind to HDL and LDL lipoprotein particles which mediate cellular uptake upon binding to their respective receptors. Thus in one aspect the invention provides formulated lipid particles (FLiPs) comprising (a) an oligonucleotide of the invention, where said oligonucleotide has been conjugated to a lipophile and (b) at least one lipid component, for example an emulsion, liposome, isolated lipoprotein, reconstituted lipoprotein or phospholipid, to which the conjugated oligonucleotide has been aggregated, admixed or associated. The stoichiometry of oligonucleotide to the lipid component can be 1:1. Alternatively the stoichiometry can be 1:many, many:1 or many:many, where many is two or more.

The FLiP can comprise triacylglycerol, phospholipids, glycerol and one or several lipid-binding proteins aggregated, admixed or associated via a lipophilic linker molecule with a single- or double-stranded oligonucleotide. Surprisingly, it has been found that due to said one or several lipid-binding proteins in combination with the above mentioned lipids, the FLiPs show affinity to heart, lung and/or muscle tissue. These FLiPs can therefore serve as carrier for oligonucleotides to these tissues.

One or more complementary surface active agents can be added to the reconstituted lipoproteins, for example as complements to the characteristics of amphiphilic agent or to improve its lipid particle stabilizing capacity or enable an improved solubilization of the protein. Such complementary agents can be pharmaceutically acceptable non-ionic surfactants which preferably are alkylene oxide derivatives of an organic compound which contains one or more hydroxylic groups. For example ethoxylated and/or propoxylated alcohol or ester compounds or mixtures thereof are commonly available and are well known as such complements to those skilled in the art. Other pharmacologically acceptable components can also be added to the FLiPs when desired, such as antioxidants (e.g., alpha-tocopherol) and solubilization adjuvants (e.g., benzylalcohol).

One suitable lipid component for FLiP is Intralipid. Intralipid® is a brand name for the first safe fat emulsion for human use. Intralipid® 20% (a 20% intravenous fat emulsion) is a sterile, non-pyrogenic fat emulsion prepared for intravenous administration as a source of calories and essential fatty acids. It is made up of 20% soybean oil, 1.2% egg yolk phospholipids, 2.25% glycerin, and water for injection. It is further within the present invention that other suitable oils, such as safflower oil, can serve to produce the lipid component of the FLiP. Suitable lipid particle formulations are also described in U.S. patent application Ser. No. 12/412,206, filed Mar. 26, 2009, contents of which are herein incorporated in their entirety.

In one embodiment of the invention is a FLiP comprising a lipid particle comprising 15-25% triacylglycerol, about 0.5-2% phospholipids and 1-3% glycerol, and one or several lipid-binding proteins. In another embodiment, a FLiP includes a liposome having about 15-25% triacylglycerol, about 1-2% phospholipids, about 2-3% glycerol, and one or several lipid-binding proteins. In yet another embodiment of the invention the lipid particle comprises about 20% triacylglycerol, about 1.2% phospholipids and about 2.25% glycerol, which corresponds to the total composition of Intralipid, and one or several lipid-binding proteins.

In one embodiment, the FLiP has a particle size of about 20-50 nm or about 30-50 nm, e.g., about 35 nm or about 40 nm.

In another embodiment, the FLiP has a particle size of at least about 100 nm. FLiPs can alternatively be between about 100-150 nm, e.g., about 110 nm, about 120 nm, about 130 nm, or about 140 nm, whether characterized as liposome- or emulsion-based.

In another embodiment, multiple FLiPs are aggregated together. In this embodiment, it is envisioned that multiple FLiPs are delivered, and hence the size can be larger than 100 nm.

Another suitable lipid component for FLiPs is lipoproteins, for example isolated lipoproteins or more preferably reconstituted lipoproteins. Lipoproteins are particles that contain both proteins and lipids. The lipids or their derivatives can be covalently or non-covalently bound to the proteins. Exemplary lipoproteins include chylomicrons, VLDL (Very Low Density Lipoproteins), IDL (Intermediate Density Lipoproteins), LDL (Low Density Lipoproteins) and HDL (High Density Lipoproteins).

Methods of producing reconstituted lipoproteins are known in the art, for example see A. Jones, Experimental Lung Res. 6, 255-270 (1984), U.S. Pat. No. 4,643,988 and U.S. Pat. No. 5,128,318, PCT publication WO87/02062, Canadian patent #2,138,925. Other methods of producing reconstituted lipoproteins, especially for apolipoproteins A-I, A-II, A-IV, apoC and apoE have been described in A. Jonas, Methods in Enzymology 128, 553-582 (1986) and G. Franceschini et al. J. Biol. Chem., 260(30), 16321-25 (1985).

In the final FLiP, the oligonucleotide component is aggregated, associated or admixed with the lipid components via a lipophilic moiety. This aggregation, association or admixture can be at the surface of the final FLiP formulation. Alternatively, some integration of any of a portion or all of the lipophilic moiety can occur, extending into the lipid particle. Any lipophilic linker molecule that is able to bind oligonucleotides to lipids can be chosen. Examples include pyrrolidine and hydroxyprolinol.

In addition to the components described above for the various formulations, these formulations can also include a targeting moiety, e.g., a targeting moiety that is specific to a cell type or tissue. Such targeting moieties can be conjugated with the formulated oligonucleotide and/or conjugated with a component of the formulation. Formulations can further comprise one or more of release modifiers, and penetration enhancers.

The most frequently used lipid for reconstitution is phosphatidyl choline, extracted either from eggs or soybeans. Other phospholipids are also used, also lipids such as triglycerides or cholesterol. For reconstitution, the lipids are first dissolved in an organic solvent, which is subsequently evaporated under nitrogen. In this method the lipid is bound in a thin film to a glass wall. Afterwards the apolipoproteins and a detergent, normally sodium cholate, are added and mixed. The added sodium cholate causes a dispersion of the lipid. After a suitable incubation period, the mixture is dialyzed against large quantities of buffer for a longer period of time; the sodium cholate is thereby removed for the most part, and at the same time lipids and apolipoproteins spontaneously form themselves into lipoproteins or so-called reconstituted lipoproteins. As alternatives to dialysis, hydrophobic adsorbents are available which can adsorb detergents (Bio-Beads SM-2, Bio Rad; Amberlite XAD-2, Rohm & Haas) (E. A. Bonomo, J. B. Swaney, J. Lipid Res., 29, 380-384 (1988)), or the detergent can be removed by means of gel chromatography (Sephadex G-25, Pharmacia). Lipoproteins can also be produced without detergents, for example through incubation of an aqueous suspension of a suitable lipid with apolipoproteins, the addition of lipid which was dissolved in an organic solvent, to apolipoproteins, with or without additional heating of this mixture, or through treatment of an apoA-I-lipid-mixture with ultrasound. With these methods, starting; for example, with apoA-I and phosphatidyl choline, disk-shaped particles can be obtained which correspond to lipoproteins in their nascent state. Normally, following the incubation, unbound apolipoproteins and free lipid are separated by means of centrifugation or gel chromatography in order to isolate the homogeneous, reconstituted lipoproteins particles.

Phospholipids used for reconstituted lipoproteins can be of natural origin, such as egg yolk or soybean phospholipids, or synthetic or semisynthetic origin. The phospholipids can be partially purified or fractionated to comprise pure fractions or mixtures of phosphatidyl cholines, phosphatidyl ethanolamines, phosphatidyl inositols, phosphatidic acids, phosphatidyl serines, sphingomyelin or phosphatidyl glycerols. According to specific embodiments of the present invention it is preferred to select phospholipids with defined fatty acid radicals, such as dimyristoyl phosphatidyl choline (DMPC), dioleoylphosphatidylethanolamine (DOPE), palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), -phosphatidylethanolamine (POPE), dioleoyl-phosphatidylethanolamine 4-(N-maleimidomethyl)-cyclohexane-1-carboxylate (DOPE-mal), and combinations thereof, and the like phosphatidyl cholines with defined acyl groups selected from naturally occurring fatty acids, generally having 8 to 22 carbon atoms. According to a specific embodiment of the present invention phosphatidyl cholines having only saturated fatty acid residues between 14 and 18 carbon atoms are preferred, and of those dipalmitoyl phosphatidyl choline is especially preferred.

Other phospholipids suitable for reconstitution with lipoproteins include, e.g., phosphatidylcholine, phosphatidylglycerol, lecithin, b, g-dipalmitoyl-a-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, and the like. Non-phosphorus containing lipids can also be used in the liposomes of the compositions of the present invention. These include, e.g., stearylamine, docecylamine, acetyl palmitate, fatty acid amides, and the like.

Besides the phospholipids, the lipoprotein can comprise, in various amounts at least one nonpolar component which can be selected among pharmaceutical acceptable oils (triglycerides) exemplified by the commonly employed vegetabilic oils such as soybean oil, safflower oil, olive oil, sesame oil, borage oil, castor oil and cottonseed oil or oils from other sources like mineral oils or marine oils including hydrogenated and/or fractionated triglycerides from such sources. Also medium chain triglycerides (MCT-oils, e.g. Miglyol®), and various synthetic or semisynthetic mono-, di- or triglycerides, such as the defined nonpolar lipids disclosed in WO 92/05571 can be used in the present invention as well as acetylated monoglycerides, or alkyl esters of fatty acids, such isopropyl myristate, ethyl oleate (see EP 0 353 267) or fatty acid alcohols, such as oleyl alcohol, cetyl alcohol or various nonpolar derivatives of cholesterol, such as cholesterol esters.

One or more complementary surface active agents can be added to the reconstituted lipoproteins, for example as complements to the characteristics of amphiphilic agent or to improve its lipid particle stabilizing capacity or enable an improved solubilization of the protein. Such complementary agents can be pharmaceutically acceptable non-ionic surfactants which preferably are alkylene oxide derivatives of an organic compound which contains one or more hydroxylic groups. For example, ethoxylated and/or propoxylated alcohol or ester compounds or mixtures thereof are commonly available and are well known as such complements to those skilled in the art. Examples of such compounds are esters of sorbitol and fatty acids, such as sorbitan monopalmitate or sorbitan monopalmitate, oily sucrose esters, polyoxyethylene sorbitane fatty acid esters, polyoxyethylene sorbitol fatty acid esters, polyoxyethylene fatty acid esters, polyoxyethylene alkyl ethers, polyoxyethylene sterol ethers, polyoxyethylene-polypropoxy alkyl ethers, block polymers and cethyl ether, as well as polyoxyethylene castor oil or hydrogenated castor oil derivatives and polyglycerine fatty acid esters. Suitable non-ionic surfactants, include, but are not limited to various grades of Pluronic®, Poloxamer®, Span®, Tween®, Polysorbate®, Tyloxapol®, Emulphor® or Cremophor® and the like. The complementary surface active agents can also be of an ionic nature, such as bile duct agents, cholic acid or deoxycholic their salts and derivatives or free fatty acids, such as oleic acid, linoleic acid and others. Other ionic surface active agents are found among cationic lipids like C10-C24: alkylamines or alkanolamine and cationic cholesterol esters.

The process for making the lipid particles comprises the steps of:
a) mixing a lipid components with one or several lipophile (e.g. cholesterol) conjugated oligonucleotides that can be chemically modified;
b) fractionating this mixture;
c) selecting the fraction with particles of 30-50 nm, preferably of about 40 nm in size.

Release Modifiers

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Polymers

Hydrophilic polymers suitable for use in the formulations of the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG (750)). Polymers can also be defined by the number of monomers therein; a preferred embodiment of the present invention utilizes polymers of at least about three monomers, such PEG polymers consisting of three monomers (approximately 150 daltons).

Other hydrophilic polymers which can be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In one embodiment, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Surfactants

The above discussed formulation can also include one or more surfactants. Surfactants find wide application in formulations such as emulsions (including microemulsions) and liposomes. The use of surfactants in drug products, formulations and in emulsions has been reviewed (Rieger, in "Pharmaceutical Dosage Forms," Marcel Dekker, Inc., New York, N.Y., 1988, p. 285). Surfactants can be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Nonionic surfactants include, but are not limited to, nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

Anionic surfactants include, but are not limited to, carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

Cationic surfactants include, but are not limited to, quaternary ammonium salts and ethoxylated amines. The quaternary ammonium salts are the most used members of this class.

Amphoteric surfactants include, but are not limited to, acrylic acid derivatives, substituted alkylamides, N-alkyl betaines and phosphatides.

A surfactant can also be selected from any suitable aliphatic, cycloaliphatic or aromatic surfactant, including but not limited to biocompatible lysophosphatidylcholines (LPCs) of varying chain lengths (for example, from about C14 to about C20). Polymer-derivatized lipids such as PEG-lipids can also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants can be utilized to prepare micelles entrapped within liposomes of the present invention, however, micelle surfactant monomers could affect liposome bilayer stability and would be a factor in designing a liposome of a desired stability.

Penetration Enhancers

In one embodiment, the formulations of the present invention employ various penetration enhancers to affect the efficient delivery of RNAi agents to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Some exemplary formulations for oligonucleotides are described in International Application Nos. PCT/US07/079203, filed Sep. 21, 2007; PCT/US07/080331, filed Oct. 3, 2007; U.S. patent application Ser. No. 12/123,922, filed May 28, 2008; U.S. Patent Application Publication Nos. 20060240093 and 20070135372 and US Provisional Application Nos. 61/018,616, filed Jan. 2, 2008; 61/039,748, filed Mar. 26, 2008; 61/045,228, filed Apr. 15, 2008; 61/047,087, filed Apr. 22, 2008; and 61/051,528, filed May 21, 2008, contents of which are herein incorporated by reference in their entireties for all purposes.

In some embodiments, the oligonucleotide is formulated as yeast cell particles. Without wishing to be bound by theory, yeast cell particles comprise an extracted yeast cell wall comprising beta-glucan and payload trapping molecule. Methods of preparing yeast cell particle for drug delivery are described in U.S. Patent Publication No. 2008/0044438 and 2005/0281781, contents of which are herein incorporated in their entireties. In certain embodiments, the yeast cell particle comprises a recombinant vector, e.g., a plasmid, that encodes for the oligonucleotide of the invention.

Agricultural Formulations and Applications

Methods of agricultural formulation are well known to one skilled in the art and are also found in Knowles, D A (1998) Chemistry and technology of agricultural formulations. Kluwer Academic, London, which is hereby incorporated by reference in its entirety. One skilled in the art will, of course, recognize that the formulation and mode of application can affect the activity of the active ingredient in a given application. Thus, for agricultural and/or horticultural use the active ingredient, e.g., oligonucleotide, can be formulated as a granular of relatively large particle size (for example, 8/16 or 4/8 US Mesh), as water-soluble or water-dispersible granules, as powdery dusts, as wettable powders, as emulsifiable concentrates, as aqueous emulsions, as solutions, as suspension concentrate, as capsule suspensions, as soluble (liquid) concentrates, as soluble powders, or as any of other known types of agriculturally-useful formulations, depending on the desired mode of application. It is to be understood that the amounts specified in this specification are intended to be approximate only, as if the word "about" were placed in front of the amounts specified.

These formulations can be applied either as water-diluted sprays, or dusts, or granules in the areas of interest. These formulations can contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 90 parts, 80 parts, 70 parts, 60 parts, 50 parts, 40 parts, 30 parts, 20 parts, preferably 10 parts, or less of the active ingredient, e.g. oligonucleotide. In one embodiment, the dust formulation comprises 1 part or less of the active ingredient and 99 parts or more of talc. As used herein, the terms "active ingredient" and "active agent" refer to a compound that modulate gene expression activity of an insect or a pathogen of insect.

Wettable powders, useful as formulations, are in the form of finely divided particles that disperse readily in water or other dispersant. The wettable powder is ultimately applied either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.0 parts of the active ingredient, 17.9 parts of Palmetto clay, and 1.0 part of sodium lignosulfonate and 0.3 part of sulfonated aliphatic polyester as wetting agents. Additional wetting agent and/or oil will frequently be added to a tank mix for to facilitate dispersion on the foliage of the plant.

Other useful formulations are emulsifiable concentrates (ECs) which are homogeneous liquid compositions dispersible in water or other dispersant, and can consist entirely of the active ingredient, and a liquid or solid emulsifying agent, or can also contain a liquid carrier, such as xylene, heavy aromatic naphthas, isophorone, or other non-volatile organic solvents. For insecticidal application these concentrates are dispersed in water or other liquid carrier and normally applied as a spray to the area to be treated. The percentage by weight of the essential active ingredient can vary according to the manner in which the composition is to be applied, but in general comprises 0.5 to 95% of active ingredient by weight of the insecticidal composition.

Flowable formulations are similar to ECs, except that the active ingredient is suspended in a liquid carrier, generally water. Flowables, like ECs, can include a small amount of a surfactant, and will typically contain active ingredients in the range of 0.5 to 95%, frequently from 10 to 50%, by weight of the composition. For application, flowables can be diluted in water or other liquid vehicle, and are normally applied as a spray to the area to be treated.

Typical wetting, dispersing or emulsifying agents used in agricultural and/or horticultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for agricultural applications include simple solutions of the active ingredient in a solvent in which it is completely soluble at the desired concentration, such as acetone, alkylated naphthalenes, xylene, or other organic solvents. Granular formulations, wherein the active ingredient is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier can also be used. Water-soluble or water-dispersible granules are free flowing, non-dusty, and readily water-soluble or water-miscible. In use by the farmer on the field, the granular formulations, emulsifiable concentrates, flowable concentrates, aqueous emulsions, solutions, etc., can be diluted with water to give a concentration of active ingredient in the range of say 0.1% or 0.2% to 1.5% or 2%.

By far the most frequently used are water-miscible formulations for mixing with water then applying as sprays. Water miscible, older formulations include: emulsifiable concentrate, wettable powder, soluble (liquid) concentrate, and soluble powder. Newer, non-powdery formulations with reduced or no hazardous solvents and improved stability include: suspension concentrate, capsule suspensions, water dispersible granules. Such formulations are preferably solutions and suspension, e.g., aqueous suspension and solutions, ethanolic suspension and solutions, aqueous/ethanolic suspension and solutions, saline solutions, and colloidal suspensions.

Alternatively, a sprayable wax emulsion formulation can be used. The formulation contains the active ingredient, in an amount from about 0.01% to 75% by weight. The aqueous wax emulsions are broadly described in U.S. Pat. No. 6,001,346, which is hereby incorporated by reference in is entirety. Formulations of the methods described herein can have a viscosity appropriate for use in aerial or backpack spray applications.

The biodegradable wax carrier comprises at least about 10% by weight of the formulation. The biodegradable wax carrier is selected from the group consisting of paraffin, beeswax, vegetable based waxes such as soywax (soybean based), and hydrocarbon based waxes such as Gulf Wax Household Paraffin Wax; paraffin wax, avg. m.p. 53C (hexacosane), high molecular weight hydrocarbons). carnauba wax, lanolin, shellac wax, bayberry wax, sugar cane wax, microcrystalline, ozocerite, ceresin, montan, candelilla wax, and combinations thereof.

Formulations can contain an emulsifier in an amount from about 1% to about 10% by weight. Suitable emulsifiers include lecithin and modified lecithins, mono- and diglycerides, sorbitan monopalmitate, sorbitan monooleate, sorbitan monolaurate, polyoxyethylene-sorbitan monooleate, fatty acids, lipids, etc. The emulsifiers provide or improve emulsification properties of the composition. The emulsifier can be selected from many products which are well known in the art, including, but not limited to, sorbitan monolaurate (anhydrosorbitol stearate, molecular formula $C_{24}H_{46}O_6$), ARLACEL 60, ARMOTAN MS, CRILL 3, CRILL K3, DREWSORB 60, DURTAN 60, EMSORB 2505, GLYCOMUL S, HODAG SMS, IONET S 60, LIPOSORB S, LIPOSORB S-20, MONTANE 60, MS 33, MS33F, NEWCOL 60, NIKKOL SS 30, NISSAN NONION SP 60, NONION SP 60, NONION SP 60R, RIKEMAL S 250, sorbitan c, sorbitan stearate, SORBON 60, SORGEN 50, SPAN 55, AND SPAN 60; other sorbitan fatty acid ester that can be used include sorbitan monopalmitate, sorbitan monostearate, sorbitan tristearate, sorbitan monooleate, sorbitan sesquioleate, sorbitan trioleate, sorbitan monooleate, sorbitan trioleate. In certain embodiments, SPAN 60 is preferred.

In certain embodiments, formulations can includes a phagostimulant, such as corn oil, molasses, glycerol, or corn syrup, proteinaceous material (protein or hydrolyzed protein), sugars like sucrose, or food-based ingredients such as trimethylamine, putrescine, bacterial or yeast volatiles or metabolites, ammonium acetate, ammonium carbonate or other ammonia-emitting compounds. Acetic acid vapor can be provided by compounds that produce volatilized acetic acid, for example, aqueous acetic acid, glacial acetic acid, glacial (concentrated) acetic acid, or ammonium producing compounds such as but not restricted to ammonium hydroxide, ammonium carbonate, ammonium bicarbonate, ammonium acetate, etc. Ammonium acetate is most preferred for providing acetic acid and ammonia vapors.

The active ingredient can be formulated and/or applied with one or more second compounds. Various combinations active ingredients can be used to obtain greater advantage. Without wishing to be bound by theory, such combinations provide certain advantages, such as, without limitation, exhibiting synergistic effects, reducing rates of application thereby minimizing any impact to the environment and to worker safety, controlling a broader spectrum of insects and non-insect pests, and improving tolerance by non-pest species, such as mammals, and fish. Other second compounds include, without limitation, attractant, insecticides, pesticides, plant growth regulators, fertilizers, soil conditioners, or other agricultural and horticultural chemicals. The formulation can include such second compounds in an amount from about 0.002% to about 25%.

Attractants include, but are not limited to, visual attractants (e.g., food coloring), pheromones, light, mimicking flowers or plants etc.

Insecticides include, but are not limited to, organophosphate insecticides, such as chlorpyrifos, diazinon, dimethoate, malathion, parathion-methyl, naled, and terbufos; nicotinic insecticides such as imidacloprid and thiacloprid; pyrethroid insecticides, such as fenvalerate, delta-methrin, fenpropathrin, cyfluthrin, flucythrinate, alpha-cypermethrin, biphenthrin, resolved cyhalothrin, etofenprox, esfenvalerate, tralomethrin, tefluthrin, cycloprothrin, betacyfluthrin, and acrinathrin; carbamate insecticides, such as aldecarb, carbaryl, carbofuran, and methomyl; organochlorine insecticides, such as endosulfan, endrin, heptachlor, and lindane; benzoylurea insecticides, such as diflubenuron, triflumuron, teflubenzuron, chlorfluazuron, flucycloxuron, hexaflumuron, flufenoxuron, dimlin, novaluron, and lufenuron; diacylhydrazines such as methoxyfenozide; phenylpyrazoles such as fipronil or ethiprole, chlorfenapyr, diafenthiuron, indoxacarb, metaflumazone, emamectin benzoate, abamectin, pyridalyl, flubendiamide, rynaxypyr; and other insecticides, such as amitraz, clofentezine, fenpyroximate, hexythiazox, spinosad, and imidacloprid.

Pesiticides include, but are not limited to, benzimidazine fungicides, such as benomyl, carbendazim, thia-bendazine, and thiophanate-methyl; 1,2,4-triazine fungicides, such as epoxyconazine, cyproconazine, flusilazine, flutriafol, propiconazine, tebuconazine, triadimefon, and tri-adimenol; substituted anilide fungicides, such as metalaxyl, oxadixyl, procymidone, and vinclozolin; organophosphorus fungicides, such as fosetyl, iprobenfos, pyrazophos, edifen-phos, and tolclofos-methyl; morpholine fungicides, such as fenpropimorph, tridemorph, and dodemorph; other systemic fungicides, such as fenarimol, imazalil, prochloraz, tricyclazine, and triforine; dithiocarbamate fungicides, such as mancozeb, maneb, propineb, zineb, and ziram; non-systemic fungicides, such as chlorothalonil, dichlorofluanid, dithianon, and iprodione, captan, dinocap, dodine, fluazinam, gluazatine, PCNB, pencycuron, quintozene, tricylamide, and validamycin; inorganic fungicides, such as copper and sulphur products, and other fungicides; nematicides such as carbofuran, carbosulfan, turbufos, aldecarb, ethoprop, fenamphos, oxamyl, isazofos, cadusafos, and other nematicides.

A variety of additives can be incorporated into the formulation. These additives typically change and/or enhance the physical characteristics of the carrier material and are, therefore, suitable for designing compositions having specific requirements as to the release rate and amount of the active ingredient, protection of the wax composition from weather conditions, etc. These additives are, among others, plasticizers, volatility suppressants, antioxidants, lipids, various ultraviolet blockers and absorbers, or antimicrobials, typically added in amounts from about 0.001% to about 10%, more typically between 1-6%, by weight.

Plasticizers, such as glycerin or soy oil affect physical properties of the composition and can extend its resistance to environmental destruction.

Antioxidants, such as vitamin E, BHA (butylated hydroxyanisole), BHT (butylated hydroxytoluene), and other antioxidants which protect the bioactive agent from degradation, can be added in amounts from about 0.1% to about 3%, by weight.

Ultraviolet blockers, such as beta-carotene, lignin or p-aminobenzoic acid protect the bioactive agents from light degradation can be added in amounts from about 1% to about 3%, by weight.

Antimicrobials, such as potassium sorbate, nitrates, nitrites, and propylene oxide, protect the bioactive agents from microbial destruction can be added in amounts from 0.1% to about 2% by weight.

Adjuvants can also be added to the formulation. An adjuvant is broadly defined as any substance added to the spray tank, separate from the pesticide formulation, that will improve the performance of the pesticide. These includes but are not limited to wetter-spreaders, stickers, penetrants, compatibility agents, buffers, and so on.

Other compounds and materials can be added provided they do not substantially interfere with the activity of active ingredient. Whether or not an additive substantially interferes with the active ingredient's activity can be determined by standard test formats, involving direct comparisons of efficacy of the composition of the active ingredient without an added compound and the composition of the active ingredient with an added compound.

Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols.

Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 18th ed., Mack Publishing Co. (1990). The pH and exact concentration of the various components of the pharmaceutical composition are adjusted according to routine skills in the art. See Goodman and Gilman's The Pharmacological Basis for Therapeutics, 10th ed., McGraw-Hill Professional (2001).

In one embodiment, the active agent can be applied to a breeding locus of insects. As used herein, the term "breeding locus" refers to an area where the insects breed, i.e. mate and/or lay eggs.

In another embodiment, the active agent is applied to a feeding locus of insects. As used here in, the term "feeding locus" refers to an area where an insect feeds. In many instances, a breeding locus and a feeding locus will be the same area.

In one embodiment, the active ingredient is preferably applied topically on plants on which an insect feeds.

In yet another embodiment, the active agent is applied to both a breeding and a feeding locus of insects.

In one embodiment, the active agent is applied as a spray to locus of insects, e.g., breeding locus, feeding locus.

In one embodiment, the active agent is applied to insect traps. For example, the trap can be coated with the active agent or trap can be loaded with insect food comprising an active agent.

Recombinant Vectors

In another aspect, oligonucleotides useful for the methods and/or compositions of the invention can be expressed from transcription units inserted into DNA or RNA vectors. For example, see, e.g., Couture, A, et al., *TIG*. (1996), 12:5-10; Skillern, A., et al., International PCT Publication No. WO 00/22113, Conrad, International PCT Publication No. WO 00/22114, and Conrad, U.S. Pat. No. 6,054,299. The vector can be either prokaryotic or eukaryotic, and typically is a virus or a plasmid. Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

One type of recombinant vector comprises a polynucleotide encoding a double-stranded oligonucleotide cooperatively linked to an expression vector. Alternatively, the two strands of the double-stranded oligonucleotide are encoded by separate open reading frames. In one embodiment, a dsRNA is expressed as an inverted repeat joined by a linker polynucleotide sequence that the dsRNA has a stem and loop structure. The phrase operatively linked refers to insertion of a polynucleotide molecule into an expression vector in a manner such that the molecule is able to be expressed when transformed into a host cell. As used herein, an expression vector is a DNA or RNA vector that is capable of transforming a host cell and of effecting expression of a specified polynucleotide molecule(s). Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, arthropod, other animal, and plant cells. Preferred expression vectors of the present invention can direct gene expression in insect cells.

In particular, expression vectors of the present invention contain regulatory sequences such as transcription control sequences, origins of replication, and other regulatory sequences that are compatible with the recombinant cell and that control the expression of the polynucleotide encoding a dsRNA or a strand thereof. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in arthropod cells. Additional suitable transcription control sequences include tissue-specific promoters and enhancers. Some exemplary compositions and methods for preparing expression vectors are described in U.S. patent application Ser. Nos. 10/522,962 and 10/531,349 and International Patent Application No. PCT/US2005/029976, contents of which are herein incorporated in their entireties.

In certain embodiments, the expression vector is a insect-infecting virus. The virus can optionally be disarmed. As used herein, the term "disarmed" means that pathogenicity of the virus is reduced and/or abolished in comparison to the wildtype virus. One of skill in the art knows of methods for producing viruses with lower and/or abolished pathogenicity. Without wishing to be bound by theory, a disarmed virus can allow the infection to spread to other insects in the hive and/or locus before the first infected virus dies.

A particularly preferred expression vector is a baculovirus. By "baculovirus" it is meant any virus of the family Baculoviridae, such as a nuclear polyhedrosis virus (NPV). Baculoviruses are a large group of evolutionarily related viruses, which infect only arthropods; indeed, some baculoviruses only infect insects that are pests of commercially important agricultural and forestry crops, while others are known that specifically infect other insect pests. Because baculoviruses infect only arthropods, they pose little or no risk to humans, plants, or the environment.

Of the suitable viruses, in addition to the Baculoviridae are the entomopox viruses (EPV), such as *Melolontha melonotha* EPV, *Amsacta moorei* EPV, *Locusta migratoria* EPV, *Melanoplus sanguinipes* EPV, *Schistocerca gregaria* EPV, *Aedes aogypti* EPV, and *Chironomus luridus* EPV. Other suitable viruses are granulosis viruses (GV). Suitable RNA viruses include togaviruses, flavivi-ruses, picornaviruses, cytoplasmic polyhedrosis viruses (CPV), and the like. The subfamily of double stranded DNA viruses Eubaculovirinae includes two genera, NPVs and GVs, which are particularly useful for biological control because they produce occlusion bodies in their life cycle. Examples of GVs include *Cydia pomonella* GV (coddling moth GV), *Pieris brassicae* GV, *Trichoplusia ni* GV, *Artogeia rapae* GV, and *Plodia interpunctella* GV (Indian meal moth).

Suitable baculoviruses for practicing this invention can be occluded or non-occluded. The nuclear polyhedrosis viruses ("NPV") are one baculovirus subgroup, which are "occluded." That is, a characteristic feature of the NPV group is that many virions are embedded in a crystalline protein matrix referred to as an "occlusion body." Examples of NPVs include *Lymantria dispar* NPV (gypsy moth NPV), *Autographa californica* MNPV, *Anagrapha falcifera* NPV (celery looper NPV), *Spodoptera litturalis* NPV, *Spodoptera frugiperda* NPV, *Heliothis armigera* NPV, *Mamestra brassicae* NPV, *Choristoneura fumiferana* NPV, *Trichoplusia ni* NPV, *Helicoverpa zea* NPV, and *Rachiplusia ou* NPV. For field use occluded viruses often are preferable due to their greater stability since the viral polyhedrin coat provides protection for the enclosed infectious nucleocapsids.

Among illustrative, useful baculoviruses in practicing this invention are those isolated from *Anagrapha falcifera*, *Anticarsia gemmatalis*, *Buzura suppressuria*, *Cydia pomonella*, *Helicoverpa zea*, *Heliothis armigera*, *Manestia brassicae*, *Plutella xylostella*, *Spodoptera exigua*, *Spodoptera littoralis*, and *Spodoptera litura*. A particularly useful "NPV" baculovirus for practicing this invention is AcNPV, which is a nuclear polyhedrosis virus from *Autographa californica*. *Autographa californica* is of particular interest because various major pest species within the genera *Spodoptera*, *Trichoplusia*, and *Heliothis* are susceptible to this virus.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes; see, e.g., Rabinowitz J E et al. (2002), J Virol 76:791-801, the entire disclosure of which is herein incorporated by reference.

The present invention may be as defined in any one of the following numbered paragraphs.

1. A method for treating or preventing disease in an insect, the method comprising administering to the insect a composition comprising an RNA effector molecule or a vector encoding an RNA effector molecule, and a delivery agent, wherein the RNA effector molecule modulates gene expression of an insect or an insect pathogen.
2. The method of paragraph 1, wherein the disease is caused by an insect pathogen selected from the group consisting of a virus, mite, nematode, bacteria, fungus, or parasite.
3. The method of paragraph 1, wherein the disease is caused by pollution, exposure to electromagnetic radiation, exposure to pesticides, environment, or stress.
4. The method of paragraph 1, wherein the RNA effector molecule inhibits or activates gene expression.
5. The method of paragraph 2, wherein modulating gene expression inhibits pathogen infectivity, virulence, reproduction, viability, growth, translation, protein production, viral uptake or transmission.
6. The method of paragraph 2, wherein modulating gene expression decreases insect susceptibility to a pathogen.
7. The method of paragraph 1, wherein the administering comprises providing a food source for the insect, wherein the food source comprises the composition.
8. The method of paragraph 7, wherein the food source is provided as a liquid, solid, gel, semi-solid composition, sugar composition, or lipid composition.
9. The method of paragraph 7, wherein the food source comprises a virus, a bacterium, a fungus, a plant, or a yeast cell expressing the RNA effector molecule.
10. The method of paragraph 1, wherein the administering comprises contacting the insect with a solution comprising the composition.
11 The method of paragraph 10, wherein the composition is administered topically.
12. The method of paragraph 10, wherein the insect is sprayed or soaked with the solution.
13. The method of paragraph 1, wherein the RNA effector molecule comprises an oligonucleotide.
14. The method of paragraph 13, wherein the oligonucleotide is a single stranded or double stranded oligonucleotide.
15. The method of paragraph 13, wherein the oligonucleotide is modified.
16. The method of paragraph 15, wherein the modification is selected from the group consisting of: 2'-O-methyl modified nucleotide, a nucleotide having a 5'-phosphorothioate group, a terminal nucleotide linked to a cholesteryl derivative, a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.
17. The method of paragraph 15, wherein the oligonucleotide comprises an siRNA, an miRNA, an shRNA, a ribozyme, an antisense RNA, a decoy oligonucleotide, an antimir, a supermir, or an RNA activator.
18. The method of paragraph 1, wherein the vector is a viral vector, an expression vector, or a plasmid.
19. The method of paragraph 1, wherein the delivery agent is a lipid, a liposome, a food source, a solution, an emulsion, a micelle or other membranous formulation, a lipid particle, a bacteria, a fungus, a plant, a yeast cell, or a yeast cell particle.
20. The method of paragraph 18, wherein the viral vector comprises a baculoviral vector.
21. The method of paragraph 19, wherein the lipid particle comprises about 15-25% triacylglycerol, about 0.5-2% phospholipids, about 1-3% glycerol, and at least one lipid-binding protein.
22. The method of paragraph 1, wherein the composition is provided in a spray, solution, gel, bait, a food source, or powder form.
23. The method of paragraph 1, wherein the composition further comprises an attractant.
24. The method of paragraph 23, wherein the attractant comprises an insect pheromone or hormone.
25. The method of paragraph 1, wherein the composition is administered in combination with an antibiotic, antiviral or anthelmintic agent.
26. The method of paragraph 1, wherein the insect is a bee, wasp, butterfly, ant or ladybug.
27. The method of paragraph 15, wherein the oligonucleotide comprises 9-36 base pairs.
28. The method of paragraph 1, wherein the composition is administered to adult insects.
29. The method of paragraph 1, wherein the composition is administered to a breeding or feeding locus.
30. The method of paragraph 1, wherein the composition further comprises an additional agent.
31. The method of paragraph 1, wherein the composition further comprises sucrose.
32. The method of any of the preceding paragraphs, wherein the insect is a hive bee or a forager bee, and the pathogen is selected from the group consisting of IAPV, Acute Bee Paralysis Virus and Kashmir Bee Paralysis Virus.
33. A method for modulating gene expression in an insect, the method comprising: administering to the insect a composition comprising an RNA effector molecule or a vector encoding an RNA effector molecule and a delivery agent, wherein the RNA effector molecule modulates gene expression in the insect.
34. The method of paragraph 33, wherein the insect is a pest.
35. The method of paragraph 33, wherein the RNA effector molecule inhibits or activates gene expression.
36. The method of paragraph 33, wherein modulation of gene expression inhibits viability, survival, growth, development, and/or reproduction of the insect.
37. The method of paragraph 33, wherein modulation of gene expression increases insect susceptibility to a pathogen.

38. The method of paragraph 33, wherein the administering comprises providing a food source for the insect, wherein the food source comprises the composition.
39. The method of paragraph 38, wherein the food source is provided as a liquid, solid, gel, semi-solid composition, sugar composition, or lipid composition.
40. The method of paragraph 38, wherein the food source comprises a virus, a bacterium, a fungus, a plant or a yeast cell expressing the oligonucleotide.
41. The method of paragraph 33, wherein the insect is a hive-dwelling insect and modulation of gene expression in the insect is delayed until the insect returns to the hive.
42. The method of paragraph 41, wherein the hive-dwelling insect spreads the composition to other insects in the hive.
43. The method of paragraph 33, wherein the administering comprises contacting the insect with a solution comprising the composition.
44. The method of paragraph 43, wherein the composition is administered topically.
45. The method of paragraph 43, wherein the insect is sprayed or soaked with the solution.
46. The method of paragraph 33, wherein the RNA effector molecule comprises an oligonucleotide.
47. The method of paragraph 46, wherein the oligonucleotide is a single stranded or double stranded oligonucleotide.
48. The method of paragraph 46, wherein the oligonucleotide is modified.
49. The method of paragraph 48, wherein the modification is selected from the group consisting of: 2'-O-methyl modified nucleotide, a nucleotide having a 5'-phosphorothioate group, a terminal nucleotide linked to a cholesteryl derivative, a T-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.
50. The method of paragraph 46, wherein the oligonucleotide comprises an siRNA, an miRNA, an shRNA, a ribozyme, an antisense RNA, a decoy oligonucleotide, an antimir, a supermir, or an RNA activator.
51. The method of paragraph 33, wherein the vector is a viral vector, an expression vector, or a plasmid.
52. The method of paragraph 33, wherein the delivery agent is a lipid, a liposome, a food source, a solution, an emulsion, a micelle or other membranous formulation, a lipid particle, a bacteria, a fungus, a plant, a yeast cell, or a yeast cell particle.
53. The method of paragraph 52, wherein the viral vector comprises a baculoviral vector.
54. The method of paragraph 52, wherein the lipid particle comprises about 15-25% triacylglycerol, about 0.5-2% phospholipids, about 1-3% glycerol, and at least one lipid-binding protein.
55. The method of paragraph 33, wherein the composition is provided in a spray, solution, gel, bait, a food source, or powder form.
56. The method of paragraph 33, wherein the composition further comprises an attractant.
57. The method of paragraph 56, wherein the attractant comprises an insect pheromone or hormone.
58. The method of paragraph 34, wherein the composition is specific to the pest and does not affect other insects.
59. The method of paragraph 46, wherein the oligonucleotide comprises 9-36 base pairs.
60. The method of paragraph 33, wherein the composition is administered to adult insects.
61. The method of paragraph 33, wherein the composition is administered to a breeding or feeding locus.
62. The method of paragraph 33, wherein the composition further comprises an additional agent.
63. The method of paragraph 33, wherein the composition further comprises sucrose.
64. A composition comprising an RNA effector molecule or a vector encoding an RNA effector molecule, and a delivery agent, wherein the RNA effector molecule modulates gene expression of an insect or an insect pathogen.
65. The composition of paragraph 64, wherein the RNA effector molecule comprises an oligonucleotide.
66. The composition of paragraph 65, wherein the oligonucleotide comprises an siRNA', an miRNA, an shRNA, a ribozyme, an antisense RNA, a decoy oligonucleotide, an antimir, a supermir, or an RNA activator.
67. The composition of paragraph 65, wherein the oligonucleotide is a single stranded or double stranded oligonucleotide.
68. The method of paragraph 64, wherein the vector is a viral vector, an expression vector, or a plasmid.
69. The method of paragraph 64, wherein the delivery agent is a lipid, a liposome, a food source, a solution, an emulsion, a micelle or other membranous formulation, a lipid particle, a bacteria, a fungus, a plant, a yeast cell, or a yeast cell particle.
70. The composition of paragraph 64, wherein the lipid particle comprises about 15-25% triacylglycerol, about 0.5-2% phospholipids, about 1-3% glycerol, and at least one lipid-binding protein.
71. The composition of paragraph 64, wherein the composition is provided as a food source for the insect.
72. The composition of paragraph 71, wherein the food source is provided as a liquid, solid, gel, semi-solid composition, sugar composition, or lipid composition.
73. The composition of paragraph 71, wherein the food source is a virus, a bacterium, a fungus, a plant, or a yeast cell expressing the oligonucleotide.
74. The composition of paragraph 64, wherein the composition inhibits viability, survival, growth, development, and/or reproduction of the insect.
75. The composition of paragraph 64, wherein the composition inhibits pathogen infectivity, virulence, reproduction, viability, growth, translation, protein production, viral uptake or transmission of the insect pathogen.
76. The composition of paragraph 64, wherein the composition is provided in a spray, solution, gel, topical formulation, or powder form.
77. The composition of paragraph 65, wherein the oligonucleotide comprises 9-36 base pairs.
78. The composition of paragraph 64, wherein the composition further comprises an antibiotic, antiviral or anthelmintic agent.
79. The composition of paragraph 64, further comprising an insect attractant.
80. The composition of paragraph 79, wherein the attractant comprises an insect pheromone or hormone.
81. The composition of paragraph 65, wherein the oligonucleotide is modified.
82. The composition of paragraph 81, wherein the modification is selected from the group consisting of: 2'-O-methyl modified nucleotide, a nucleotide having a 5'-phosphorothioate group, a terminal nucleotide linked to a cholesteryl derivative, a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.
83. The composition of paragraph 64, further comprising an additional agent.
84. The composition of paragraph 64, further comprising sucrose.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified in the specification and examples are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

The invention claimed is:

1. A method for treating disease in an insect, the method comprising administering to the insect a composition comprising a double stranded RNA (dsRNA) molecule or a vector encoding a dsRNA molecule, and a delivery agent, wherein the dsRNA molecule is 19-24 nucleotides long, comprises a sense strand and an antisense strand, and modulates gene expression of an insect, wherein the double-stranded region of the dsRNA is about 19 nucleotides in length, and wherein the dsRNA further comprises (i) at least one mismatch, (ii) a 5'-terminal dinucleotide overhang, or a 3'-terminal dinucleotide overhang, or both a 5'- and 3'-dinucleotide overhang, and (iii) at least one asymmetrical modification, and wherein the dsRNA molecule comprises at least one nucleotide modification to increase stabilization of the dsRNA, the modification selected from the group consisting of:

(i) a 5'-phosphorothioate or 5'-phosphorodithioate modifications within the double stranded region, (ii) a phosphorothioate modification within the nucleotides at the terminal overhang region, (iii) a cationic modification of nucleotides 1 and 2 on the 5' terminus, wherein the cationic modification is at the C5 position of pyrimidines and C2, C6 and C8, exocyclic N2 or exocyclic N6 of purines,
(iv) at least one 2'-fluoro modified nucleotide comprising a nucleobase modification
(v) at least one 2'-O-methyl/2'-fluoro modified nucleotide comprising a nucleobase modification,
(vi) a 5'-PuPu-3' dinucleotide at the 3' terminal of at least one of the strands in the dsRNA molecule wherein both nucleotides comprise a modified methoxyethyl (MOE) at 2'-position, and
(vii) a 5'-PuPu-3' dinucleotide at the 5' terminal of at least one of the strands in the dsRNA molecule wherein both nucleotides comprise a modified MOE at 2'-position; and wherein modulation of the gene treats the disease.

2. The method of claim 1, wherein the disease is caused by an insect pathogen selected from the group consisting of a virus, mite, nematode, bacteria, fungus, or parasite.

3. The method of claim 1, wherein the disease is caused by pollution, exposure to electromagnetic radiation, exposure to pesticides, environment, or stress.

4. The method of claim 1, wherein the dsRNA molecule inhibits or activates gene expression.

5. The method of claim 1, wherein said administering comprises providing a food source for the insect, wherein the food source comprises the composition.

6. The method of claim 5, wherein the food source comprises a virus, a bacterium, a fungus, a plant, or a yeast cell expressing the RNA effector molecule.

7. The method of claim 1, wherein said administering comprises contacting the insect with a solution comprising the composition.

8. The method of claim 7, wherein the composition is administered topically.

9. The method of claim 1, wherein the vector is a viral vector, an expression vector, or a plasmid.

10. The method of claim 9, wherein the viral vector comprises a baculoviral vector.

11. The method of claim 1, wherein the insect is a bee, wasp, butterfly, ant or ladybug.

12. The method of claim 1, wherein the composition is administered to adult insects.

13. The method of claim 1, wherein the composition is administered to a breeding or feeding locus.

14. The method of claim 1, wherein the insect is a hive bee or a forager bee, and the pathogen is selected from the group consisting of IAPV, Acute Bee Paralysis Virus and Kashmir Bee Paralysis Virus.

15. A method for modulating gene expression in an insect, the method comprising: administering to the insect a composition comprising a dsRNA molecule or a vector encoding a dsRNA molecule and a delivery agent, wherein the dsRNA molecule is 19-24 nucleotides long, comprises a sense strand and an antisense strand, and modulates gene expression in the insect,
wherein the double-stranded region of the dsRNA is about 19 nucleotides in length, and
wherein the dsRNA further comprises (i) at least one mismatch, (ii) a 5'-terminal dinucleotide overhang, or a 3'-terminal dinucleotide overhang, or both a 5'- and 3'-dinucleotide overhang, and (iii) at least one asymmetrical modification, and
wherein the dsRNA molecule comprises at least one nucleotide modification to increase stabilization of the dsRNA, the modification selected from the group consisting of:
(i) a 5'-phosphorothioate or 5'-phosphorodithioate modifications within the double stranded region,
(ii) a phosphorothioate modification within the nucleotides at the terminal overhang region,
(iii) a cationic modification of nucleotides 1 and 2 on the 5' terminus, wherein the cationic modification is at the C5 position of pyrimidines and C2, C6 and C8, exocyclic N2 or exocyclic N6 of purines,
(iv) at least one 2'-fluoro modified nucleotide comprising a nucleobase modification
(v) at least one 2'-O-methyl/2'-fluoro modified nucleotide comprising a nucleobase modification,
(vi) a 5'-PuPu-3' dinucleotide at the 3' terminal of at least one of the strands in the dsRNA molecule wherein both nucleotides comprise a modified methoxyethyl (MOE) at 2'-position, and
(vii) a 5'-PuPu-3' dinucleotide at the 5' terminal of at least one of the strands in the dsRNA molecule wherein both nucleotides comprise a modified MOE at 2'-position; and wherein modulation of the gene treats a disease.

16. The method of claim 15, wherein the insect is a hive-dwelling insect and modulation of gene expression in the insect is delayed until the insect returns to the hive.

* * * * *